(12) United States Patent
Park et al.

(10) Patent No.: US 9,175,335 B2
(45) Date of Patent: *Nov. 3, 2015

(54) BIOMOLECULE INTERACTION USING ATOMIC FORCE MICROSCOPE

(71) Applicants: POSCO, Pohang-si, Kyungsanbuk-do (KR); POSTECH FOUNDATION, Pohang, Kyungsangbuk-Do (KR)

(72) Inventors: Joon Won Park, Pohang (KR); Yu Jin Jung, Daejeon (KR); Bong Jin Hong, Busan (KR); Saul Tendler, Nottingham (GB); Stephanie Allen, Nottingham (GB)

(73) Assignees: POSCO, Pohang-shi, Kyungsangbuk-do (KR); POSTECH FOUNDATION, Pohang, Kyungsangbuk-do (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/215,367

(22) Filed: Mar. 17, 2014

(65) Prior Publication Data

US 2014/0315319 A1 Oct. 23, 2014

Related U.S. Application Data

(63) Continuation of application No. 11/673,732, filed on Feb. 12, 2007, now Pat. No. 8,673,621, which is a continuation-in-part of application No. 11/464,481, filed as application No. PCT/KR2005/002651 on Aug. 12, 2005, now abandoned.

(60) Provisional application No. 60/707,892, filed on Aug. 12, 2005, provisional application No. 60/817,608, filed on Jun. 28, 2006, provisional application No. 60/601,237, filed on Aug. 12, 2004.

(51) Int. Cl.
| | | |
|---|---|---|
| C12Q 1/68 | (2006.01) |
| C12M 1/00 | (2006.01) |
| C12M 1/34 | (2006.01) |
| C07H 21/02 | (2006.01) |
| G01C 19/00 | (2013.01) |
| G01Q 60/24 | (2010.01) |
| B82Y 35/00 | (2011.01) |
| G01Q 60/42 | (2010.01) |

(52) U.S. Cl.
CPC .............. *C12Q 1/6827* (2013.01); *B82Y 35/00* (2013.01); *C12Q 1/6834* (2013.01); *G01Q 60/42* (2013.01); *Y10T 436/143333* (2015.01)

(58) Field of Classification Search
CPC .......... C12Q 1/68; C07H 21/02; B82Y 35/00; G01Q 60/04
USPC ........... 435/6.1, 283.1, 287.2; 536/23.1, 24.3; 73/504.15; 850/21, 23

See application file for complete search history.

(56) References Cited

U.S. PATENT DOCUMENTS 5,372,930 A * 12/1994 Colton et al. ................ 435/6.19
5,874,668 A * 2/1999 Xu et al. ........................ 73/105

FOREIGN PATENT DOCUMENTS

KR WO2006/016787 * 2/2006
WO WO 02/20469 * 3/2002

OTHER PUBLICATIONS

Consolandi et al, Two Efficient Polymeric Chemical Platforms for Oligonucleotide Microarray Preparation, 2002, Nucleosides, Nucleotides and Nucleic Acids, 21, 561-580.*

* cited by examiner

*Primary Examiner* — Narayan Bhat
(74) *Attorney, Agent, or Firm* — Don D. Cha; Hamilton DeSanctis & Cha, LLP.

(57) ABSTRACT

The present patent application describes a cantilever for atomic force microscopy (AFM), which includes a cantilever body having a fixed end and a free end, the free end having a surface region being chemically modified by a dendron in which a plurality of termini of the branched region of the dendron are bound to the surface, and a terminus of the linear region of the dendron is functionalized.

11 Claims, 18 Drawing Sheets

(a)  (b)

FIG. 18
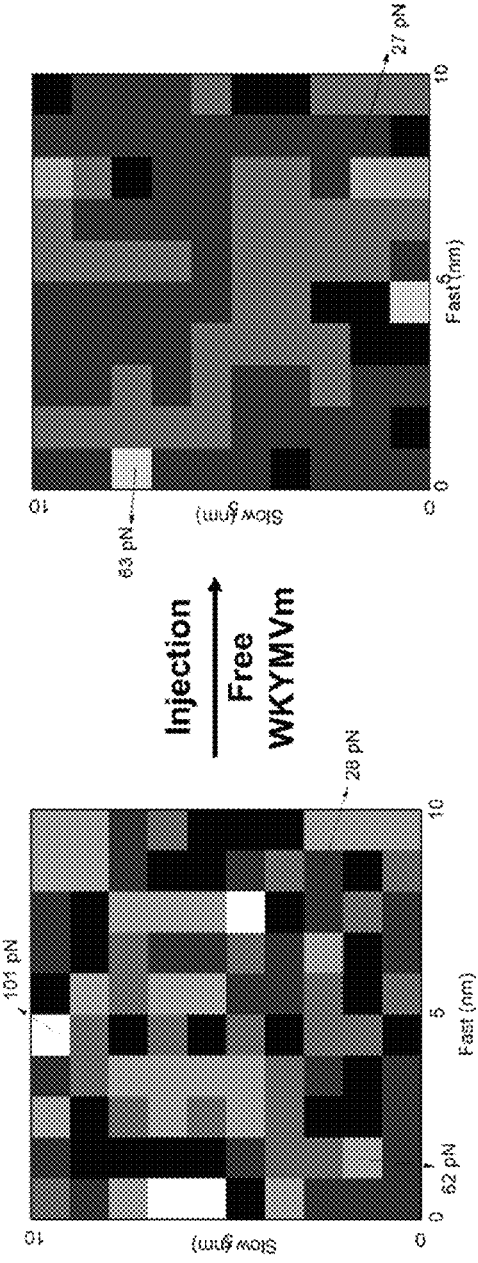
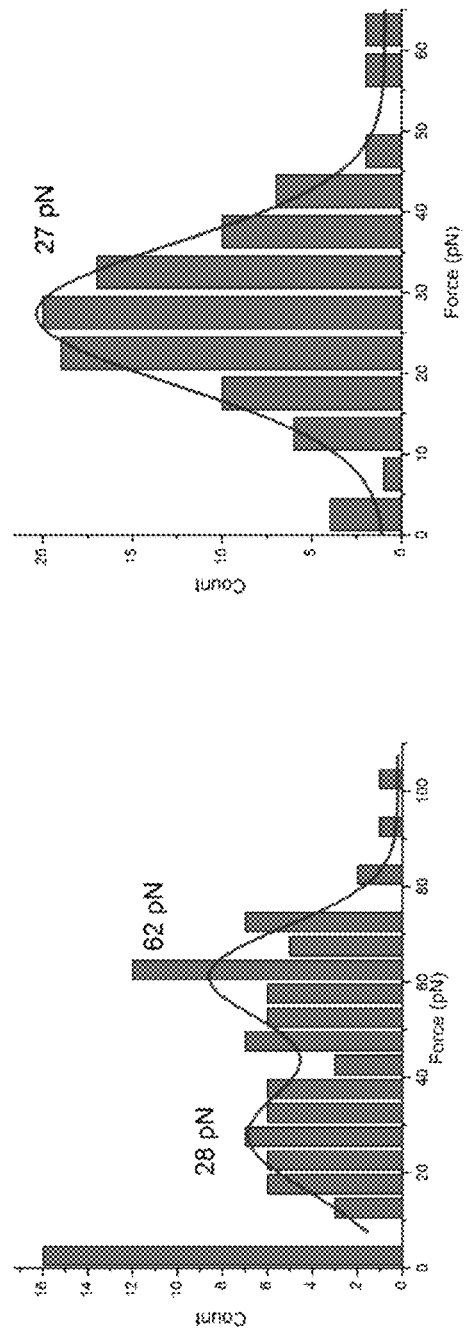

BIOMOLECULE INTERACTION USING ATOMIC FORCE MICROSCOPE

CONTINUING DATA

The present application is a Continuation of Ser. No. 11/673,732, filed Feb. 12, 2007, which is a continuation-in-part of U.S. patent application Ser. No. 11/464,481, filed Aug. 14, 2006, abandoned, which claims priority to U.S. Provisional Patent Application No. 60/707,892, filed Aug. 12, 2005, and U.S. Provisional Patent Application No. 60/817,608, filed Jun. 28, 2006, the contents of which are incorporated by reference herein in their entirety. U.S. patent application Ser. No. 11/673,732 also claims priority to PCT/KR2005/002651, filed Aug. 12, 2005, which claims priority to U.S. Provisional Patent Application No. 60/601,237, filed Aug. 12, 2004, the contents of which are also incorporated by reference herein in their entirety.

BACKGROUND OF THE INVENTION (a) Field of the Invention

The present invention relates generally to atomic force microscopy (AFM), a cantilever for AFM, and an apparatus and a measuring method of intermolecular interaction between the biomolecules using the same. The present invention regards the usage of dendron coated Bio-AFM tips in measuring the interaction force between biomolecules. The present invention also provides details on Bio-AFM Force Mapping of cell receptors by using surfaces with controlled meso spaces.

(b) Description of the Related Art

In the post-genomic era, quantitative and comprehensive studies on genome for drug discovery, as well as disease diagnosis and prevention, are fast-growing research and development areas. Growth in these sectors has already produced a strong demand for advanced biomolecular recognition probes with high sensitivity and excellent specificity (K. Wang et al., *Anal. Chem.* 76, 5721 2004).

Out of many biomolecular recognition studies, understanding the mechanical stability (or recognition property) of complementary DNA strands is crucial for a profound understanding of numerous important biological processes, such as DNA transcription, gene expression and regulation, and DNA replication. In this respect, stretching and force-induced melting of DNA have thus been investigated using several techniques, such as optical tweezers, micro-pipette suction, and AFM (H. Clausen-Schaumann, M. Seitz, R. Krautbauer, H. E. Gaub, *Curr. Opin. Chem. Biol.* 4, 524, 2000; R. Merkel, *Physics Reports* 346, 343, 2001; G. U. Lee, L. A. Chris, R. J. Colton, *Science* 266, 771, 1994).

As it is possible to measure specific interactions between individual molecules at small length scales and high sensitivity down to forces of a few piconewtons, AFM is becoming a rapidly developing technique for probing affinity and recognition properties at the molecular level (R. Krautbauer, M. Rief, H. E. Gaub, *Nano Lett.* 3, 493, 2003). Compared with other sensitive methods for force measurements, AFM has the advantages of high force resolution and high spatial resolution, and is operable under physiological conditions for investigation of specific interactions in biological processes, such as electrostatic interactions (J. Wang, A. J. Bard, *Anal. Chem.* 73, 2207, 2001), ligand-receptor binding (S. M. Rigby-Singleton et al., *J. Chem. Soc., Perkin Trans.* 2 1722, 2002), antigen-antibody interactions (F. Schwesinger et al., *Proc. Natl. Acad. Sci. U.S.A.* 97, 9972, 2000), aptamer-protein interactions (C. Bai et al., *Anal. Chem.* 75, 2112, 2003), protein folding/unfolding (P. M. Williams et al., *Nature* 422, 446, 2003; M. S. Z. Kellermayer, S. B. Smith, H. L. Granzier, C. Bustamante, *Science* 276, 1112, 1997), cell-cell adhesion (M. Benoit, D. Gabriel, G. Gerisch, H. E. Gaub, *Nature Cell Biol.* 2, 313, 2000) and DNA-DNA hybridization (C. W. Frank, *Biophys. J.* 76, 2922, 1999).

Although many investigations have been performed on unbinding force measurement between complementary DNA strands (H. Clausen-Schaumann, M. Seitz, R. Krautbauer, H. E. Gaub, *Curr. Opin. Chem. Biol.* 4, 524, 2000; R. Merkel, *Physics Reports* 346, 343, 2001; G. U. Lee, L. A. Chris, R. J. Colton, *Science* 266, 771. 1994; R. Krautbauer, M. Rief, H. E. Gaub, *Nano Lett.* 3, 493, 2003), the recognition between the DNA strands during the studies at the single molecular level is problematic. The typical immobilization approach suffered from multi-point interaction, and resolving out single molecular interactions has not been an easy task. In order to avoid the unwanted interaction, surface density was reduced by mixing with an inactive surfactant, but the approach resulted in low recognition efficiency leading to less reliable analysis. Therefore, commonly practiced surface chemistry for such immobilization such as oxide-silane and gold-thiol chemistry (T. Hugel, M. Seitz, *Macromol. Rapid. Commun.* 22, 989, 2001; W. K. Zhang, X. Zhang, *Prog. Polym. Sci.* 28, 1271, 2003) has yet to be optimized to retrieve invaluable fundamental information on single DNA-DNA interaction during the force measurement with AFM.

Atomic Force Microscopy has traditionally played an important role in understanding the various interaction mechanisms between biomolecules present inside organisms. Through its ability to analyze interaction forces, its importance within the fields of nano and biotechnology is expected to increase into the future as more studies are conducted on the molecular level.

Taking advantage of this technology, many efforts have been made to investigate interactive mechanisms between biomolecules on different surfaces. Unlike liquid, however, observation of biological material on surfaces produce unique problems such as involuntary adsorption and steric hindrance. Among the many measures taken to counter such problems, the most popular one involve measuring monomolecular interaction by applying complex self-assembling film onto surfaces. When observing the singular interaction force between two biomolecules with AFM, two issues come to the forefront. The first problem regards the difference in biomolecular activity on a surface as opposed to within the body. The second issue hinges around the fact that monomolecular interaction cannot be guaranteed in such a setting. Prior research has shown that both problems can be addressed by using self-assembling film technology and meso space manipulation technology (Langmuir 2005, 21, 4257, WO 2006/016787) The technology involves observing intermolecular interactions on the monomolecular level by controlling the spacing and number of biomolecules through limitation of the number of functional groups on which the molecules can be introduced. The most common problem of this method involves the unintended attraction between molecules of the same functional group, resulting in phase separation. In addition, there is no concrete evidence that the biomolecules are evenly spaced between each other.

The importance of biomolecular research using Bio-AFM technology is growing rapidly. Its ability to observe nonconductive material such as biomolecules on the nanometer level in a liquid environment that supports biological activity has made Bio-AFM an important tool in studying the structure and substructures of biological molecules. Additionally, Bio-AFM enables close observation of molecular interaction by its Bio-AFM tip, onto which a biomolecule can be loaded. Important applications include observation of interactions between complementary DNA molecules, mutual interactions between proteins, ligand-receptor interactions, the latter of which holds significance in studying immunological responses to drugs. In researching interaction forces between biomolecules on the monomolecular level, high sensitivity is of primary importance. Monomolecule observation can be accomplished through methods such as Bio-AFM, optical tweezing and magnetic tweezing. Each method comes with its own shortcomings, such as loss of accuracy under the magnetic tweezing method and potential damage that can be incurred upon molecules under the optical tweezing method.

In order to research ligand-receptor mechanisms using Bio-AFM, a ligand needs to be loaded on top of the tip. Generally this is accomplished by utilizing biotin-streptavidin interactions or by use of compound self-assembly films. However, such methods cannot directly control molecular distancing, and can cause ligands to concentrate in certain areas, posing difficulties in observing ligand-receptor interactions with accuracy.

SUMMARY OF THE INVENTION

An object of the invention is to provide a cantilever for atomic force microscopy (AFM) comprising a cantilever body having a fixed end and a free end, the free end having a surface region being chemically modified by a dendron in which a plurality of termini of the branched region of the dendron are bound to the surface, and a terminus of the linear region of the dendron is functionalized.

Another object of the present invention is to provide the cantilever for AFM where the dendrons are spaced at regular intervals between about 0.1 nm and about 100 nm between the linear functionalized groups. In particular, the dendrons may be spaced at regular intervals of about 10 nm.

A further object of the present invention is to provide a method for manufacturing the cantilever, comprising (i) functionalizing the surface region of the cantilever so that it will react with the termini of the dendrons; and (ii) contacting the dendrons to the surface region so that the termini and the surface form a bond.

An object of the present invention is to provide a method for manufacturing the cantilever, wherein a probe nucleotide, ligand for a receptor or a linker molecule linked to the probe nucleotide or ligand is fixed to the terminus of the linear region of dendrons, comprising the steps of i) removing protecting group from the terminus of the linear region of the dendrons on the surface region; and ii) contacting a probe nucleotide, ligand for a receptor or a linker molecule linked to the probe nucleotide or ligand to the terminus of the linear region of the dendrons on the substrate so that the probe nucleotide, ligand or the linker molecule and the terminus form a bond, wherein the linker molecule is a homo-bifunctional or hetero-bifunctional linker.

The present invention also provides an apparatus for measuring an interaction between one probe nucleotide or ligand and one target nucleotide or ligand binding partner such as its receptor by atomic force microscopy, the apparatus comprising:

a cantilever having a fixed end and a free end, the free end having a surface region being chemically modified by a dendron in which a plurality of termini of the branched region of the dendron is bound to the surface, and a terminus of the linear region of the dendron is attached to the probe nucleotide or ligand;

a substrate on which is immobilized a target nucleotide or ligand binding partner;

a controller for adjusting the relative position and orientation of the cantilever and target nucleotide or ligand binding partner on a substrate to cause an interaction between the probe nucleotide or ligand immobilized on the dendron-modified surface region of the cantilever and the target nucleotide or ligand binding partner immobilized on a substrate; and a detector for measuring a physical parameter associated with the interaction between the probe nucleotide or ligand and the sample nucleic acid or ligand binding partner.

In an embodiment, the substrate to be immobilized by the target nucleotide or ligand binding partner can be adopted by any kind of the surface modification method in the art. Preferably, the substrate has a dendron-modified surface.

A further object of the present invention is to provide a method of assaying a target nucleotide or ligand binding partner for interaction with a probe nucleotide or ligand, the method comprising the steps of:

(a) providing a cantilever having a fixed end and a free end, the free end having a surface region being chemically modified by dendrons in which a plurality of termini of the branched region of the dendrons are bound to the surface, and a substrate;

(b) chemically modifying the substrate to immobilize a target nucleotide or ligand binding partner thereon;

(c) chemically modifying the dendron-modified surface region of the cantilever to immobilize a probe nucleotide or ligand;

(d) coupling the substrate and the cantilever to an apparatus that includes a controller for adjusting the relative position and orientation of the substrate and the cantilever to cause an interaction between the probe nucleotide or ligand immobilized on the dendron-modified surface region of the cantilever and the target nucleotide or ligand binding partner immobilized on the substrate of the sample support member, (e) controlling the relative position and orientation of the cantilever and the substrate to cause an interaction between the probe nucleotide or ligand and the target nucleotide or ligand binding partner; and (f) measuring a physical parameter associated with the interaction between the probe nucleotide or ligand and the target nucleotide or ligand binding partner.

In the above, the terminus of the branched region may be functionalized with —COZ, —NHR, —OR', or —PR"3, wherein Z may be a leaving group, wherein R may be an alkyl, wherein R' may be alkyl, aryl, or ether, and R" may be H, alkyl, alkoxy, or O. In particular, COZ may be ester, activated ester, acid halide, activated amide, or CO-imidazoyl; R may be C1-C4 alkyl, and R' may be C1-C4 alkyl. Further, in the substrate described above, the polymer may be a dendron. Still further, the linear region of the polymer may include a spacer region. Also the spacer region may be connected to the branched region via a first functional group. Such first functional group may be without limitation —NH2, —OH, —PH3, —COOH, —CHO, or —SH. Still further, the spacer region may comprise a linker region covalently bound to the first functional group.

In the substrate and AFM cantilever, preferably AFM tip, the linker region may comprise a substituted or unsubstituted alkyl, alkenyl, alkynyl, cycloalkyl, aryl, ether, polyether, ester, or aminoalkyl group. Still further, the spacer region may comprise a second functional group. The second functional group may include without limitation, —NH2, —OH, —PH3, —COOH, —CHO, or —SH. The second functional group may be located at the terminus of the linear region.

Also, a protecting group may be bound to the terminus of the linear region. Such protecting group may be acid labile or base labile.

In another embodiment of the invention, in the AFM cantilever as described above, a probe ligand or nucleotide and/or a target ligand binding partner or nucleotide may be bound to the terminus of the linear region of the dendron. In particular, the target nucleotide and the probe nucleotide may be DNA, RNA, PNA, aptamer, nucleotide analog, or a combination thereof. The target-specific ligand may include nucleotides but may be more generally thought of as a chemical compound, polypeptide, carbohydrate, antibody, antigen, biomimetics, nucleotide analog, or a combination thereof.

Further, the distance between the ligands or nucleotides bound to the linear region of the dendron may be from about 0.1 to about 100 nm.

In yet another embodiment of the invention, the substrate described above may be made of semiconductor, synthetic organic metal, synthetic semiconductor, metal, alloy, plastic, silicon, silicate, glass, or ceramic. In particular, the substrate may be without limitation a slide, particle, bead, micro-well, or porous material.

These and other objects of the invention will be more fully understood from the following description of the invention, the referenced drawings attached hereto and the claims appended hereto.

BRIEF DESCRIPTION OF THE DRAWINGS

FIG. 18 shows the force map and histogram for the interaction between FPR1 and its biding peptide before and after blocking with a free WKYMVm (SEQ ID NO:17).

DETAILED DESCRIPTION

Figure 1A:
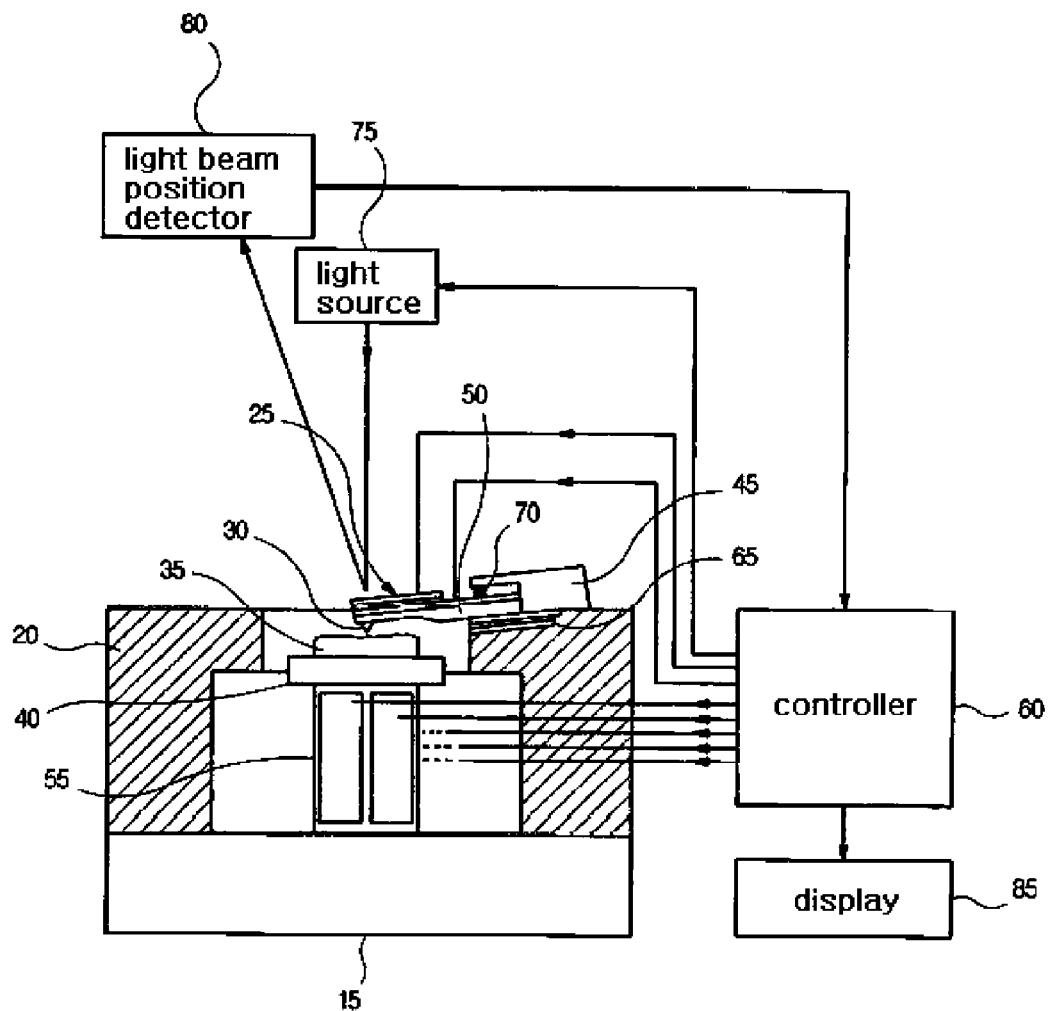
FIG. 1A a schematic view of a bio-AFM.

In the present application, "a" and "an" are used to refer to both single and a plurality of objects.

As used herein, "aptamer" means a single-stranded, partially single-stranded, partially double-stranded or double-stranded nucleotide sequence, advantageously replicatable nucleotide sequence, capable of specifically recognizing a selected nonoligonucleotide molecule or group of molecules by a mechanism other than Watson-Crick base pairing or triplex formation.

As used herein, "biomimetic" means a molecule, group, multimolecular structure or method that mimics a biological molecule, group of molecules, structure.

The term "dendrimer" is characterized by a core, at least one interior branched layer, and a surface branched layer (see Petar et al, Pages 641-645, In Chem. in Britain, August 1994). A "dendron" is a species of dendrimer having branches emanating from a focal point, which is or can be joined to a core, either directly or through a linking moiety to form a dendrimer. Many dendrimers include two or more dendrons joined to a common core. However, the term "dendrimer" may be used broadly to encompass a single dendron.

As used herein, "hyperbranched" or "branched" as it is used to describe a macromolecule or a dendron structure is meant to refer to a plurality of polymers having a plurality of termini which are able to bind covalently or ionically to a substrate. In one embodiment, the macromolecule containing the branched or hyperbranched structure is "pre-made" and is then attached to a substrate.

As used herein, "immobilized" means insolubilized or comprising, attached to or operatively associated with an insoluble, partially insoluble, colloidal, particulate, dispersed, suspended and/or dehydrated substance or a molecule or solid phase comprising or attached to a solid support.

As used herein, "library" refers to a random or nonrandom mixture, collection or assortment of molecules, materials, surfaces, structural shapes, surface features or, optionally and without limitation, various chemical entities, monomers, polymers, structures, precursors, products, modifications, derivatives, substances, conformations, shapes, or features.

As used herein, "ligand" means a selected molecule capable of specifically binding to another molecule by affinity-based attraction, which includes complementary base pairing. Ligands include, but are not limited to, nucleic acids, various synthetic chemicals, receptor agonists, partial agonists, mixed agonists, antagonists, response-inducing or stimulus molecules, drugs, hormones, pheromones, transmitters, autacoids, growth factors, cytokines, prosthetic groups, coenzymes, cofactors, substrates, precursors, vitamins, toxins, regulatory factors, antigens, haptens, carbohydrates, molecular mimics, structural molecules, effector molecules, selectable molecules, biotin, digoxigenin, crossreactants, analogs, competitors or derivatives of these molecules as well as library-selected nonoligonucleotide molecules capable of specifically binding to selected targets and conjugates formed by attaching any of these molecules to a second molecule.

As used herein, "ligand binding partner" refers to a molecule specifically binds to the ligand.

As used herein, "linker molecule" and "linker" when used in reference to a molecule that joins the branched portion of a size-controlled macromolecule such as a branched/linear polymer to a protecting group or a ligand. Linkers may include, for instance and without limitation, spacer molecules, for instance selected molecules capable of attaching a ligand to a dendron.

As used herein, "low density" refers to about 0.01 to about 0.5 probe/nm2, preferably about 0.05 to about 0.2, more preferably about 0.075 to about 0.15, and most preferably about 0.1 probe/nm2.

As used herein, "molecular mimics" and "mimetics" are natural or synthetic nucleotide or nonnucleotide molecules or groups of molecules designed, selected, manufactured, modified or engineered to have a structure or function equivalent or similar to the structure or function of another molecule or group of molecules, e.g., a naturally occurring, biological or selectable molecule. Molecular mimics include molecules and multimolecular structures capable of functioning as replacements, alternatives, upgrades, improvements, structural analogs or functional analogs to natural, synthetic, selectable or biological molecules.

As used herein, "probe nucleotide" or "target nucleotide" includes a sequence of nucleotides, such as an oligonucleotide, and is not limited to one nucleotide.

As used herein, "nucleotide analog" refers to molecules that can be used in place of naturally occurring bases in nucleic acid synthesis and processing, preferably enzymatic as well as chemical synthesis and processing, particularly modified nucleotides capable of base pairing and optionally synthetic bases that do not comprise adenine, guanine, cytosine, thymidine, uracil or minor bases. This term includes, but is not limited to, modified purines and pyrimidines, minor bases, convertible nucleosides, structural analogs of purines and pyrimidines, labeled, derivatized and modified nucleosides and nucleotides, conjugated nucleosides and nucleotides, sequence modifiers, terminus modifiers, spacer modifiers, and nucleotides with backbone modifications, including, but not limited to, ribose-modified nucleotides, phosphoramidates, phosphorothioates, phosphonamidites, methyl phosphonates, methyl phosphoramidites, methyl phosphonamidites, 5'-β-cyano ethyl phosphoramidites, methylenephosphonates, phosphorodithioates, peptide nucleic acids, achiral and neutral internucleotidic linkages and nonnucleotide bridges such as polyethylene glycol, aromatic polyamides and lipids.

As used herein, "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The term may also include variants on the traditional peptide linkage joining the amino acids making up the polypeptide.

As used herein, "protecting group" refers to a group that is joined to a reactive group (e.g., a hydroxyl or an amine) on a molecule. The protecting group is chosen to prevent reaction of the particular radical during one or more steps of a chemical reaction. Generally the particular protecting group is chosen so as to permit removal at a later time to restore the reactive group without altering other reactive groups present in the molecule. The choice of a protecting group is a function of the particular radical to be protected and the compounds to which it will be exposed. The selection of protecting groups is well known to those of skill in the art. See, for example Greene et al., Protective Groups in Organic Synthesis, 2nd ed., John Wiley & Sons, Inc. Somerset, N.J. (1991), which is incorporated by reference herein in its entirety.

As used herein, "protected amine" refers to an amine that has been reacted with an amino protecting group. An amino protecting group prevents reaction of the amide function during attachment of the branched termini to a solid support in the situation where the linear tip functional group is an amino group. The amino protecting group can be removed at a later time to restore the amino group without altering other reactive groups present in the molecule. For example, the exocyclic amine may be reacted with dimethylformamide diethylacetal to form the dimethylaminomethylenamino function. Amino protecting groups generally include carbamates, benzyl radicals, imidates, and others known to those of skill in the art. Preferred amino protecting groups include, but are not limited to, p-nitrophenylethoxycarbonyl or dimethyaminomethylenamino.

As used herein, "regular intervals" refers to the spacing between the tips of the size-controlled macromolecules, which is a distance from about 1 nm to about 100 nm so as to allow room for interaction between the target-specific ligand and the target substantially///without steric hindrance. Thus, the layer of macromolecules on a substrate is not too dense for specific molecular interactions to occur.

As used herein, "solid support" refers to a composition comprising an immobilization matrix such as, but not limited to, insolubilized substance, solid phase, surface, substrate, layer, coating, woven or nonwoven fiber, matrix, crystal, membrane, insoluble polymer, plastic, glass, biological or biocompatible or bioerodible or biodegradable polymer or matrix, microparticle or nanoparticle. Solid supports include, for example and without limitation, monolayers, layers, commercial membranes, resins, matrices, fibers, separation media, chromatography supports, polymers, plastics, glass, mica, gold, beads, microspheres, nanospheres, silicon, gallium arsenide, organic and inorganic metals, semiconductors, insulators, microstructures and nanostructures. Microstructures and nanostructures may include, without limitation, microminiaturized, nanometer-scale and supramolecular probes, tips, bars, pegs, plugs, rods, sleeves, wires, filaments, and tubes.

As used herein, "spacer molecule" refers to one or more nucleotide and/or nonnucleotide molecules, groups or spacer arms selected or designed to join two nucleotide or non-nucleotide molecules and preferably to alter or adjust the distance between the two nucleotide or non-nucleotide molecules.

As used herein, "specific binding" refers to a measurable and reproducible degree of attraction between a ligand and its specific binding partner or between a defined sequence segment and a selected molecule or selected nucleic acid sequence. The degree of attraction need not be maximized to be optimal. Weak, moderate or strong attractions may be appropriate for different applications. The specific binding which occurs in these interactions is well known to those skilled in the art. When used in reference to synthetic defined sequence segments, synthetic aptamers, synthetic heteropolymers, nucleotide ligands, nucleotide receptors, shape recognition elements, and specifically attractive surfaces. The term "specific binding" may include specific recognition of structural shapes and surface features. Otherwise, specific binding refers explicitly to the specific, saturable, noncovalent interaction between two molecules (i.e., specific binding partners) that can be competitively inhibited by a third molecule (i.e., competitor) sharing a chemical identity (i.e., one or more identical chemical groups) or molecular recognition property (i.e., molecular binding specificity) with either specific binding partner. The competitor may be, e.g., a crossreactant, or analog of an antibody or its antigen, a ligand or its receptor, or an aptamer or its target. Specific binding between an antibody and its antigen, for example, can be competitively inhibited either by a crossreacting antibody or by a crossreacting antigen. The term "specific binding" may be used for convenience to approximate or abbreviate a subset of specific recognition that includes both specific binding and structural shape recognition.

As used herein, "substrate," when used in reference to a substance, structure, surface or material, means a composition comprising a nonbiological, synthetic, nonliving, planar, spherical or flat surface that is not heretofore known to comprise a specific binding, hybridization or catalytic recognition site or a plurality of different recognition sites or a number of different recognition sites which exceeds the number of different molecular species comprising the surface, structure or material. The substrate may include, for example and without limitation, semiconductors, synthetic (organic) metals, synthetic semiconductors, insulators and dopants; metals, alloys, elements, compounds and minerals; synthetic, cleaved, etched, lithographed, printed, machined and microfabricated slides, devices, structures and surfaces; industrial polymers, plastics, membranes; silicon, silicates, glass, metals and ceramics; wood, paper, cardboard, cotton, wool, cloth, woven and nonwoven fibers, materials and fabrics; nanostructures and microstructures unmodified by immobilization probe molecules through a branched/linear polymer.

As used herein, "target-probe binding" means two or more molecules, at least one being a selected molecule, attached to one another in a specific manner. Typically, a first selected molecule may bind to a second molecule that either indirectly, e.g., through an intervening spacer arm, group, molecule, bridge, carrier, or specific recognition partner, or directly, i.e., without an intervening spacer arm, group, molecule, bridge, carrier or specific recognition partner, advantageously by direct binding. A selected molecule may specifically bind to a nucleotide via hybridization. Other noncovalent means for conjugation of nucleotide and nonnucleotide molecules include, e.g., ionic bonding, hydrophobic interactions, ligand-nucleotide binding, chelating agent/metal ion pairs or specific binding pairs such as avidin/biotin, streptavidin/biotin, anti-fluorescein/fluorescein, anti-2,4-dinitrophenol (DNP)/DNP, anti-peroxidase/peroxidase, anti-digoxigenin/digoxigenin or, more generally, receptor/ligand. For example, a reporter molecule such as alkaline phosphatase, horseradish peroxidase, β-galactosidase, urease, luciferase, rhodamine, fluorescein, phycoerythrin, luminol, isoluminol, an acridinium ester or a fluorescent microsphere which is attached, e.g., for labeling purposes, to a selected molecule or selected nucleic acid sequence using avidin/biotin, streptavidin/biotin, anti-fluorescein/fluorescein, anti-peroxidase/peroxidase, anti-DNP/DNP, anti-digoxigenin/digoxigenin or receptor/ligand (i.e., rather than being directly and covalently attached) may be conjugated to the selected molecule or selected nucleic acid sequence by means of a specific binding pair.

By controlling the spacing between immobilized DNA strands on the surfaces of both an AFM tip and a substrate, unbinding and binding forces of a single oligonucleotide were measured. It was observed that the recognition efficiency could be improved, and multiple and/or secondary interaction was eliminated with appropriate choice of the spacing. In particular, histograms of unbinding force of DNA duplexes with 20, 30, 40, and 50 base pairs became sharp and represented the force of single duplex. Surprisingly, binding events were also observed, and the corresponding force coincided with the unbinding force. Also, linear increases of both forces were observed with the increase of DNA strand length, and the force measurement was sensitive enough to discriminate a single point mutation.

The present invention provides a cantilever for atomic force microscopy (AFM) comprising a cantilever body having a fixed end and a free end, the free end having a surface region being chemically modified by a dendron in which a plurality of termini of the branched region of the dendron are bound to the surface, and a terminus of the linear region of the dendron is functionalized.

Figure 1B:
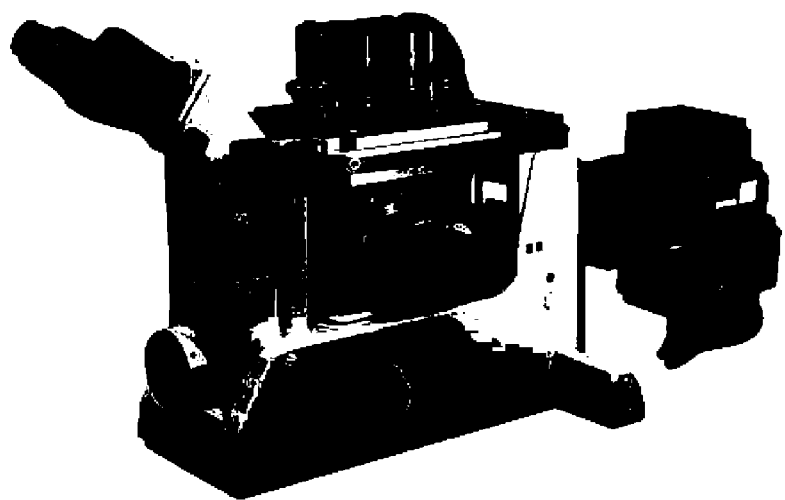
FIGS. 1B and 1C are photographs of the bio-AFM.
Figure 1C:
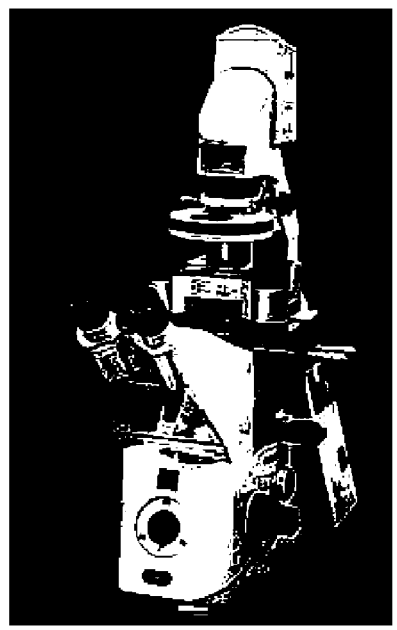
Figure 2A:
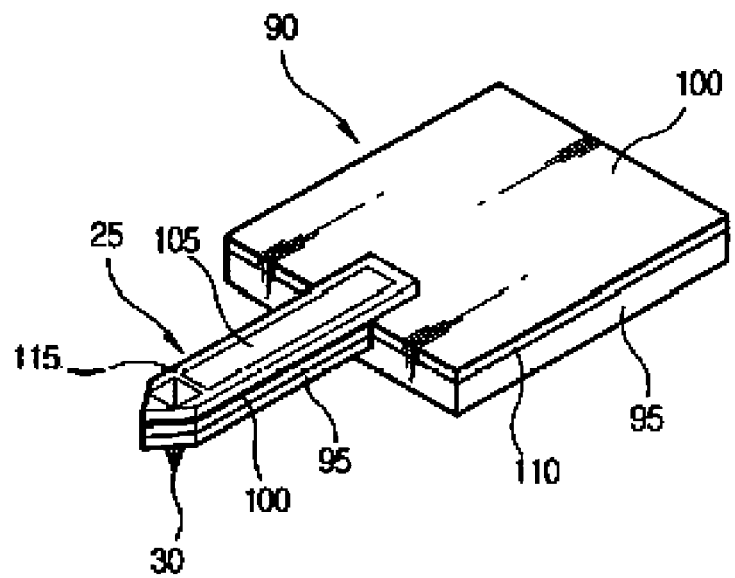
FIG. 2A is a schematic drawing of a cantilever for AFM.

In an embodiment of the present invention, at least a tapered protrusion is provided in the vicinity of the free end of the cantilever, and the protrusion is pyramidal or conical. Numerous analogous structures of the probe tip are shown in FIG. 2C. Thus, the surface region of the free end of the cantilever is brought into contact with or into proximity with a particular protrusion so that interactions between a molecule of the reference compound and a can be measured. All types of cantilevers for AFM can be used in the present invention, and they are not specifically limited. The cantilever of the present invention can be used for all type of AFM such as apparatus shown in FIGS. 1B and 1C. FIG. 1A shows an example of a general atomic force microscope, and FIG. 2A is a cantilever for AFM. The AFM of the present invention can be illustrated in reference to FIG. 1A. The AFM system 10 includes a base 15, frame 20 having an opening on its central position fixed to the base 15, and tube-like piezoelectric actuator 55 fixed to the base 15. The tube-like piezoelectric actuator 55 is deflectable in the vertical direction indicated by an arrow V2, i.e., in the direction of thickness of the cantilever by applying a voltage to the piezoelectric actuator from a controller CO through wiring lines.

In reference to FIG. 2A, the cantilever 50 has a structure such that a piezoelectric actuator 25 is formed on one side of a substrate 95. An exemplary embodiment of the cantilever, the cantilever 50 includes a cantilever base 90 which has an electrode 10 formed on a insulating layer 110 laminated on rectangular substrate 95.

The cantilever may be constructed of any material known in the art for use in AFM cantilevers, including Si, $SiO_2$, $Si_3N_4$, $Si_3N_4Ox$, Al, or piezoelectric materials. The chemical composition of the cantilever is not critical and is preferably a material that can be easily microfabricated and that has the requisite mechanical properties for use in AFM measurements. Likewise, the cantilever may be in any size and shape known in the art for AFM cantilevers. The size of the cantilever preferably ranges from about 5 microns to about 1000 microns in length, from about 1 micron to about 100 microns in width, and from about 0.04 microns to about 5 microns in thickness. Typical AFM cantilevers are about 100 microns in length, about 20 microns in width and about 0.3 microns in thickness. The fixed end of the cantilever may be adapted so that the cantilever fits or interfaces with a cantilever-holding portion of a conventional AFM.

The surface region of the free end of the cantilever may be modified for treatment with dendron for example, with silane agents such as GPDES or TPU.

The apparatus and methods of the present invention are not limited to use with cantilever-based AFM instruments.

Polymers such as that in Chemical Formula 1 may be referred to in describing the inventive polymer.

Chemical Formula 1

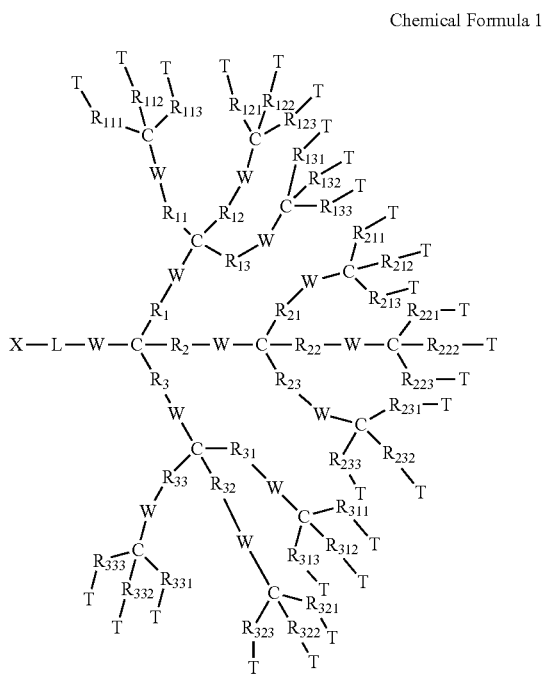

Various R, T, W, L, and X group variables are noted in chemical formula 1. The polymer may comprise any branched or hyperbranched, symmetrical or asymmetrical polymer. The branched termini of the polymer bind to the substrate preferably by a plurality of termini. The linear end of the polymer may end with a functional group to which a protecting group or a target nucleotide may be attached. The distance between the probes among the plurality of polymers on a substrate may be from about 0.1 nm to about 100 nm, preferably about 1 nm to about 100 nm, more preferably about 2 nm to about 70 nm, even more preferably about 2 nm to about 60 nm, and most preferably about 2 nm to about 50 nm.

R-Groups

In Formula I, the polymer generally includes a branched section, wherein the termini of the ends are functionalized to bind to a substrate. Within this branched section, the first generation group of branches Rx (R1, R2, R3) is connected to a second generation group of branches $R_{XX}$ (R11, R12, R13, R21, R22, R23, R31, R32, R33) by a functional group, W. The second gene ration group of branches is connected to a third generation group of branches Rxxx (R111, R112, R113, R121, R122, R123, R131, R132, R133, R211, R212, R213, R221, R222, R223, R231, R232, R233, R311, R312, R313, R321, R322, R323, R331, R332, R333) by a functional group W. And a further fourth generation may be connected to the third generation branches in like fashion. The terminal R group is functionalized so that it is capable of binding to the substrate.

The R groups of all generations may be the same or different. Typically, the R group may be a repeating unit, a linear or branched organic moiety, such as but not limited to alkyl, alkenyl, alkynyl, cycloalkyl, aryl, ether, polyether, ester, aminoalkyl, and so on. However, it is also understood that not all of the R groups need to be the same repeating unit. Nor do all valence positions for the R group need be filled with a repeating unit. For instance, in the first generation branch, $R_x$, $R_1$, $R_2$, $R_3$ all of the R groups at this branch level may be the same repeating units. Or, $R_1$ may be a repeating unit, and $R_2$ and $R_3$ may be H or any other chemical entity. Or, $R_2$ may be a repeating unit, and $R_1$ and $R_3$ may be H or any other chemical entity. Likewise, for the second and third generation branches, any R group may be a repeating unit, H or any other chemical entity.

Thus, a variety of shapes of polymers may be made in this way, for instance, if $R_1$, $R_{11}$, $R_{111}$, $R_{112}$ and $R_{113}$ are the same repeating units, and all other R groups are H's or any number of small neutral molecule or atom, then a fairly long and thin polymer having a branch with three functional group termini for $R_{111}$, $R_{112}$ and $R_{113}$ is made. A variety of other optional chemical configurations are possible. Thus, it is possible to obtain from about 3 to about 81 termini having a functional group capable of binding to a substrate. A preferable number of termini may be from about 3 to about 75, from about 3 to about 70, from about 3 to about 65, from about 3 to about 60, from about 3 to about 55, from about 3 to about 50, from about 3 to about 45, from about 3 to about 40, from about 3 to about 35, from about 3 to about 30, from about 3 to about 27, from about 3 to about 25, from about 3 to about 21, from about 3 to about 18, from about 3 to about 15, from about 3 to about 12, from about 3 to about 9, or from about 3 to about 6.

T-Terminal Group

Terminal groups, T, are functional groups that are sufficiently reactive to undergo addition or substitution reactions. Examples of such functional groups include without limitation, amino, hydroxyl, mercapto, carboxyl, alkenyl, allyl, vinyl, amido, halo, urea, oxiranyl, aziridinyl, oxazolinyl, imidazolinyl, sulfonato, phosphonato, isocyanato, isothiocyanato, silanyl, and halogenyl.

W-Functional Group

In Formula I, W may be any functional group that may link a polymer to another (or any other divalent organic) moiety, such as but not limited to ether, ester, amide, ketone, urea, urethane, imide, carbonate, carboxylic acid anhydride, carbodiimide, imine, azo group, amidine, thiocarbonyl, organic sulphide, disulfide, polysulfide, organic sulphoxide, sulphite, organic sulphone, sulphonamide, sulphonate, organic sulphate, amine, organic phosphorous group, alkylen, alkyleneoxide, alkyleneamine and so on.

L-Spacer or Linker Group

In Chemical Formula 1, the linear portion of the polymer may include a spacer domain comprised of a linker region optionally interspersed with functional groups. The linker region may be comprised of a variety of polymers. The length of the linker may be determined by a variety of factors, including the number of branched functional groups binding to the substrate, strength of the binding to the substrate, the type of R group that is used, in particular, the type of repeating unit that is used, and the type of the protecting group or target nucleotide that is to be attached at the apex of the linear portion of the polymer. Therefore, it is understood that the linker is not to be limited to any particular type of polymer or to any particular length.

However, as a general guideline, the length of the linker may be from about 0.5 nm to about 20 nm, preferably, about 0.5 nm to about 10 nm, and most preferably about 0.5 nm to about 5 nm.

The chemical construct of the linker may include without limitation, a linear or branched organic moiety, such as but not limited to substituted or unsubstituted alkyl, alkenyl, alkynyl, cycloalkyl, cycloalkenyl, aryl, ether, polyether, ester, aminoalkyl, polyalkylene glycol and so on. The linker may further include functional groups such as those described above, and as such is not limited to any particular structure. The linker group functionalized at the tip may comprise a protective group.

X-Protecting Group

The choice of protecting group depends on numerous factors such as the desirability of acid- or base-lability. Therefore, the invention is not limited to any particular protecting group so long as it serves the function of preventing the reaction of the functional group with another chemical entity, and that it is capable of being stripped under desired specified conditions. A list of commercially available protecting groups may be found in the Sigma-Aldrich (2003) Catalog, the contents of which as it relates to the disclosure of protective groups is incorporated by reference herein in its entirety.

The polymer may be deprotected, either in succession or in a single operation. Removal of the polypeptide and deprotection can be accomplished in a single operation by treating the substrate-bound polypeptide with a cleavage reagent, for example thianisole, water, ethanedithiol and trifluoroacetic acid.

In general, in one aspect of the invention, the protecting groups used in the present invention may be those that are used in the sequential addition of one or more amino acids or suitably protected amino acids to a growing peptide chain.

Normally, either the amino or carboxyl group of the first amino acid is protected by a suitable protecting group.

In a particularly preferred method, the amino function is protected by an acid or base sensitive group. Such protecting groups should have the properties of being stable to the conditions of linkage formation, while being readily removable without destruction of the growing branched/linear polymer. Such suitable protecting groups may be without limitation 9-fluorenylmethyloxycarbonyl (Fmoc), t-butyloxycarbonyl (Boc), benzyloxycarbonyl (Cbz), biphenylisopropyl-oxycarbonyl, t-amyloxycarbonyl, isobornyloxycarbonyl, (a,a)-dimethyl-3,5-dimethoxybenzyloxycarbonyl, o-nitrophenylsulfenyl, 2-cyano-t-butyloxycarbonyl, and the like.

Particularly preferred protecting groups also include 2,2,5,7,8-pentamethylchroman-6-sulfonyl (pmc), p-toluenesulfonyl, 4-methoxybenzenesulfonyl, adamantyloxycarbonyl, benzyl, o-bromobenzyloxycarbonyl, 2,6-dichlorobenzyl, isopropyl, t-butyl (t-Bu), cyclohexyl, cyclophenyl and acetyl (Ac), 1-butyl, benzyl and tetrahydropyranyl, benzyl, p-toluenesulfonyl and 2,4-dinitrophenyl.

In the addition method, the branched termini of the linear/branched polymer is attached to a suitable solid support. Suitable solid supports useful for the above synthesis are those materials which are inert to the reagents and reaction conditions of the stepwise condensation-deprotection reactions, as well as insoluble in the media used.

The removal of a protecting group such as Fmoc from the linear tip of the branched/linear polymer may be accomplished by treatment with a secondary amine, preferably piperidine. The protected portion may be introduced in about 3-fold molar excess and the coupling may be preferably carried out in DMF. The coupling agent may be without limitation O-benzotriazol-1-yl-N,N,N',N'-tetramethyluronium-hexafluorophosphate (HBTU, 1 equiv.) and 1-hydroxybenzotriazole (HOBT, 1 equiv.).

The polymer may be deprotected, either in succession or in a single operation. Removal of the polypeptide and deprotection can be accomplished in a single operation by treating the substrate-bound polypeptide with a cleavage reagent, for example thianisole, water, ethanedithiol and trifluoroacetic acid.

The substrate may be any solid surface to which the branched/linear polymer may bind through either covalent or ionic bond. The substrate may be functionalized so that binding may occur between the branched termini of the branched/linear polymer. The surface of the substrate may be a variety of surfaces according to the needs of the practitioner in the art. Preferably, the substrate may be a glass slide. Other substrates may include membrane filters such as but not limited to nitrocellulose or nylon. The substrate may be hydrophilic or polar, and may possess negative or positive charge before or after coating.

The type of dendron and its preparation method is specifically disclosed in WO2005/026191, which is incorporated herein by reference.

Reaction scheme 1 is a scheme showing the synthesis of a dendron. Various starting materials, intermediate compounds, and dendron compounds can be used, wherein "X" may be any protecting group, including anthracenemethyl (A), Boc, Fmoc, Ns and so forth.

Reaction scheme 1

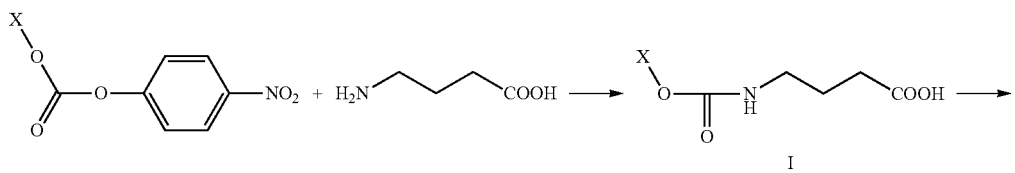

I

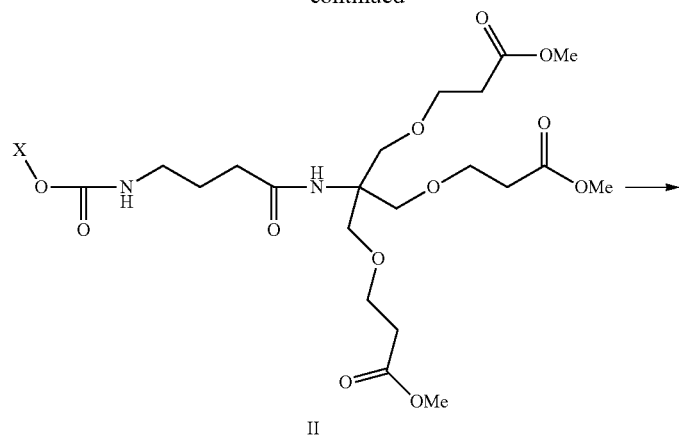
II
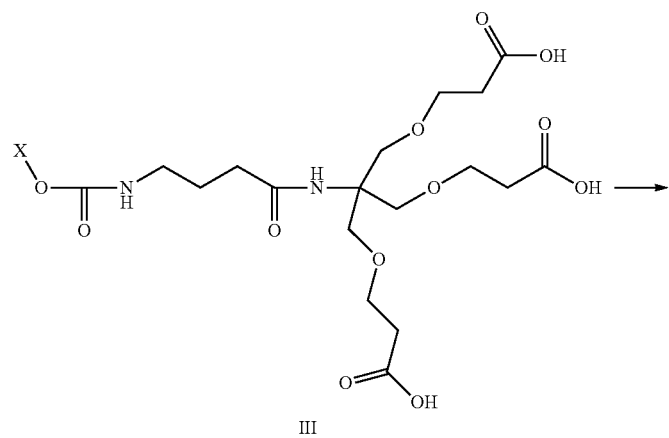
III
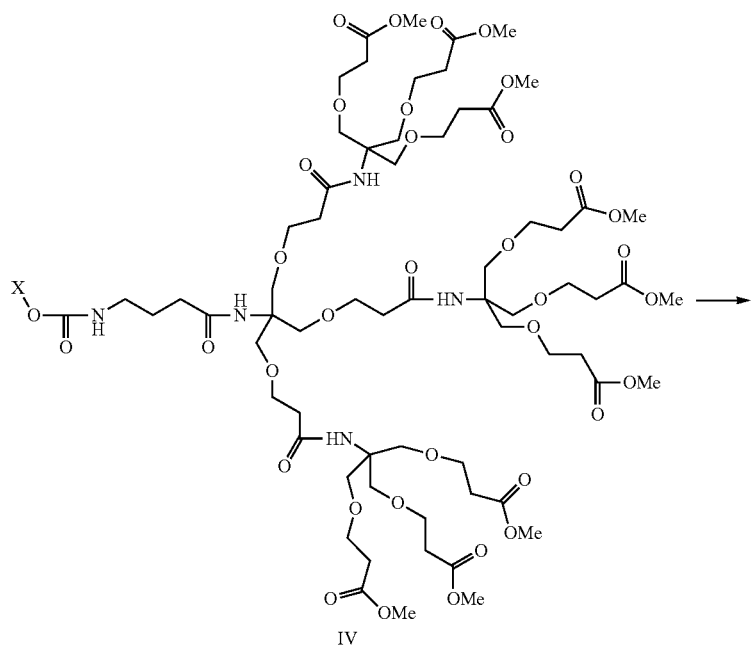
IV

-continued

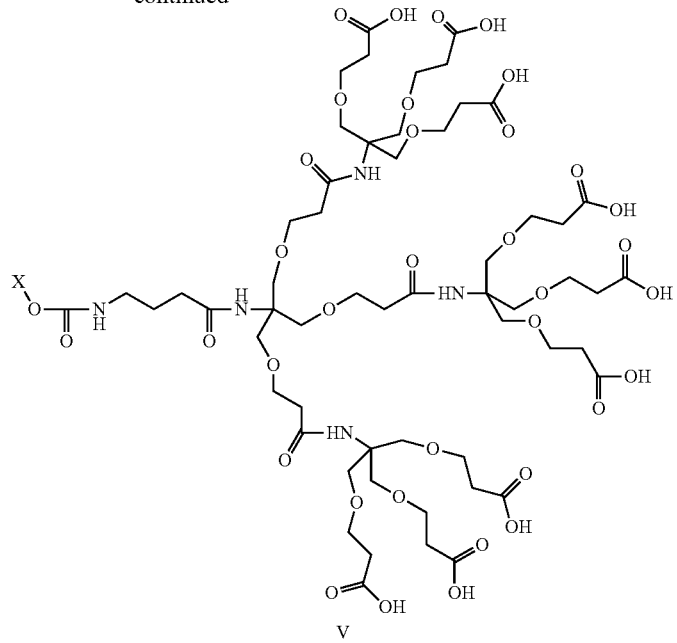

V

A second generation branch dendron having surface reactive functional groups at the branch termini may be used, which self assembles and provides appropriate spacing among themselves. Previous studies showed that multiple ionic attractions between cations on a glass substrate and anionic carboxylates at the dendron's termini successfully generated a well-behaved monolayer, and guaranteed an inter-ligand space of over 24 Å (Hong et al., Langmuir 19, 2357-2365 (2003)). To facilitate deprotection and increase the deprotected apex amine's reactivity, the structure was modified. Also, covalent bond formation between the dendron's carboxylic acid groups and the surface hydroxyl groups is as effective as ionic attraction, while also providing enhanced thermal stability. Moreover, an oligoethereal interlayer was effective for suppressing non-specific oligonucleotide binding.

The hydroxylated substrate was prepared by using a previously reported method (Maskis et al., Nucleic Acids Res. 20, 1679-1684 (1992)). Substrates including oxidized silicon wafer, fused silica, and glass slide, were modified with (3-glycidoxypropyl)methyldiethoxysilane (GPDES) and ethylene glycol (EG). The dendron was introduced to the above substrates through a coupling reaction between the dendron's carboxylic acid group and the substrate's hydroxyl group using 1-[3-(dimethylamino)propyl]-3-ethylcarbodiimide hydrochloride (EDC) or 1-3-dicyclohexylcarbodiimide (DCC) in the presence of 4-dimethylaminopyridine (DMAP) (Boden et al., J. Org. Chem. 50, 2394-2395 (1985); Dhaon et al., J. Org. Chem. 47, 1962-1965 (1982)). The increase in thickness after dendron introduction was 11±2 Å, which was comparable to the previous value observed for the ionic bonding (Hong et al., Langmuir 19, 2357-2365 (2003)).

After modification with di(N-succinimidyl) carbonate (DSC) according to a previously established method (Beier et al., Nucleic Acids Res. 27, 1970-1977 (1999)), probe oligonucleotides were immobilized onto the activated surface of glass slide by spotting 50 mM sodium bicarbonate buffer (10% dimethylsulfoxide (DMSO), pH 8.5) solution of the appropriate amine-tethered oligonucleotide (20, uM) using a Microsys 5100 Microarrayer (Cartesian Technologies, Inc.) in a class 10,000 clean room. Typically, for substrates with a reactive amine surface group, a thiol-tethered oligonucleotide and a heterobifunctional linker such as succinimidyl 4-maleimido butyrate (SMB) or sulphosuccinimidyl-4-(N-maleimidomethyl) cyclohexane-1-carboxylate (SSMCC) are employed (Oh et al., Langmuir 18, 1764-1769 (2002); Frutos et al., Langmuir 16, 2192-2197 (2000)). In contrast, because the dendron-modified surface guarantees a certain distance among the amine functional groups, use of homobifunctional linkers such as DSC is not problematic. As a result, an amine-tethered oligonucleotide can be utilized for spotting. Unless cost effectiveness is important, use of easily oxidized thiol-tethered oligonucleotide should be avoided, although it is possible that such thiol-tethered oligonucleotides may be useful under certain conditions.

To improve the recognition efficiency between complementary DNA strands at the single molecular level, DNA oligomers was immobilized onto a nanoscale-controlled dendron surface. The surface seemed to be ideal to increase the efficiency since the mesospacing existing in the dendron relieved the immobilized DNA from the steric hindrance (B. J. Hong, S. J. Oh, T. O. Youn, S. H. Kwon, J. W. Park, Langmuir 21, 4257, 2005). Either glycidylpropyldiethoxymethylsilane (or GPDES) or N-(3-(triethoxysilyl)propyl)-O-polyethyleneoxide urethane (or TPU) was employed to generate a sublayer, and the dendron (9-anthrylmethyl N-({[tris ({2-[({tris[(2-carboxyethoxy)methyl]methyl}amino) carbonyl]ethoxy}methyl)methyl]amino}carbonyl) propylcarbamate) (or 9-acid) was immobilized onto them. Previously, mesospacing between the dendrons on the GPDES-modified surface was 32 Å on average (B. J. Hong, S. J. Oh, T. O. Youn, S. H. Kwon, J. W. Park, Langmuir 21, 4257, 2005). In the case of TPU, an absorption peak observed at 257 nm arising from the anthracene moiety of the pristine dendron was one half of that in the GPDES case. Therefore it is suggested that the spacing of the dendron is larger than 32 Å in the TPU case. After deprotection of the anthracene protecting group, the amine group was activated with di(N-succinimidyl)carbonate, and eventually an amine tethering oligonucleotide was immobilized.

Figure 3:
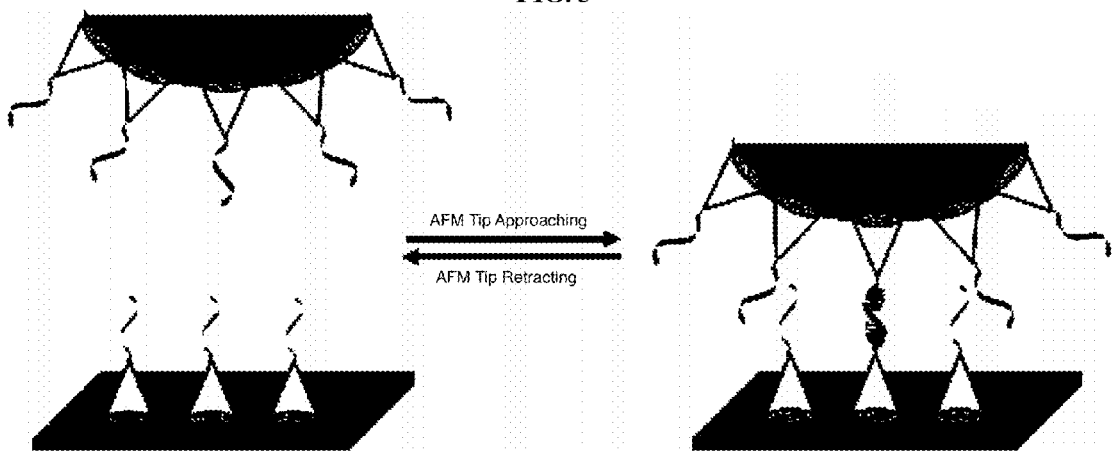
FIG. 3 is a schematic drawing of the interface between the probe tip of AFM and substrate target for measuring binding and unbinding forces with the AFM methodology.

To understand the effect of the spacing, the two types of modification were employed for the substrate, while spacing on AFM tip was fixed with use of 9-acid/TPU. Since estimation of the spring constant was believed to give a typical error of 10~20%, the force was measured under various conditions with an identical tip (FIG. 3). For example, force curves were obtained for a complementary 30-base DNA (Table 1) immobilized on 9-acid/GPDES substrate at various loading rates in the range between 110 nm/s and 540 nm/s. The perfectly matched and internal mismatched oligomer sequences are shown in Table 1, where the underlined parts are mismatched sites.

caused by alterations in biological composition. In addition, the dendron of the present invention allows measurement of interaction force between singular biotin and streptavidin by adjusting spacing between biotin molecules.

Dendron types that are applicable to the present invention are further indicated in detail in U.S. patent application Ser. No. 10/917,601 and WO 2005/026191, the contents of which are incorporated by reference herein in their entirety.

The present invention, as shown in subsequent examples, maintains ample space between ligand molecules by fixing a ligand onto the AFM tip with the help of a dendron that can manipulate meso space. This minimizes unwanted steric hindrance and static interaction between ligand and receptor, providing an optimal environment for binding. This environ-

TABLE 1

| SIZE | Oligomer on the substrate | Oligomer on the tip (perfect matching) | Oligomer on the tip (single base internal mismatching) | Oligomer on the tip (double base internal mismatching) |
|---|---|---|---|---|
| 20 bases | 5'-H$_2$N-CCATCGTGGTTGC TCCTCAG-3' (SEQ ID NO: 1) | 5'-H$_2$N-CTGAGGAGCAAC CACGATGG-3' (SEQ ID NO: 5) | 5'-H$_2$N-CTGAGGAGCTAC CACGATGG-3' (SEQ ID NO: 9) | 5'-H$_2$N-CTGAGGAGCTTC CACGATGG-3' (SEQ ID NO: 13) |
| 30 bases | 5'-H$_2$N-GCTGCTATGGAG ACACGCCCTGGA ACGAAG-3' (SEQ ID NO: 2) | 5'-H$_2$N-CTTCGTTCCAGGG CGTGTCTCCATAG CAGC-3' (SEQ ID NO: 6) | 5'-H$_2$N-CTTCGTTCCAGGG CGCGTCTCCATAG CAGC-3' (SEQ ID NO: 10) | 5'-H$_2$N-CTTCGTTCCAGGG CTCGTCTCCATAG CAGC-3' (SEQ ID NO: 14) |
| 40 bases | 5'-H$_2$N-TGGATCTGGGGT GCCATTCCGCTGT CTCAAGGTGTGCT CG-3' (SEQ ID NO: 3) | 5'-H$_2$N-CGAGCACACCTT GAGACAGCGGAA TGGCACCCCAGA TCCA-3' (SEQ ID NO: 7) | 5'-H$_2$N-CGAGCACACCTT GAGACAGCGTAA TGGCACCCCAGA TCCA-3' (SEQ ID NO: 11) | 5'-H$_2$N-CGAGCACACCTT GAGACAGCGTCA TGGCACCCCAGA TCCA-3' (SEQ ID NO: 15) |
| 50 bases | 5'-H$_2$N-GTCTGACCTGTTC CAACGACCCGTA TCACTCCGCTCCT GCCTGCTCTC CA-3' (SEQ ID NO: 4) | 5'-H$_2$N-TGGAGAGCAGGC AGGAGCGGAGTG ATACGGGTCGTT GGAACAGGTCAG AC-3' (SEQ ID NO: 8) | 5'-H$_2$N-TGGAGAGCAGGC AGGAGCGGAGTG TTACGGGTCGTTG GAACAGGTCAGA C-3' (SEQ ID NO: 12) | 5'-H$_2$N-TGGAGAGCAGGC AGGAGCGGAGTG TAACGGGTCGTT GGAACAGGTCAG AC-3' (SEQ ID NO: 16) |

A solid substrate with a dendron controlled meso space maintains even distancing among monomolecules, thus effectively widening research applications to drug screening, investigation of protein-protein interaction and protein-small molecule interaction. Bio-AFM enables highly accurate measurements while minimizing molecular damage.

The present invention maintains even spacing between biomolecules fixed on the surface of solid substrate dendron, with adjusted meso space structure. Unwanted steric hindrance is minimized, providing an optimal environment for observing interactions between monomolecules. The term biomolecule encompasses substances such as proteins, antigens, antibodies, signaling proteins, peptides, integral membrane proteins, small molecules, steroids, glucose, DNA, RNA, and others.

Specifically, according to Examples 8 and 9, and FIGS. 11 to 15, it has been demonstrated that the present invention causes uniform force between PLD1-PX and Munc-18-1, which form a specific bond. The present invention can be applied to drug screening by measuring interaction force using Bio-AFM. By observing the change of interaction force between biomolecules in accordance with changes in the environment, cause and effect relations can be more clearly established for a wide array of diseases that are believed to be ment also minimizes multiple bonding, and thus allows close observation of ligand-receptor interaction on the monomolecular level.

The present invention, by using a surface of controlled meso space structure when introducing an AFM tip loaded with specific ligands (which form specific bonds with cell surface receptors) maintains even spacing between ligands and thus allows for accurate mapping of receptor distribution. When using AFM tips which meso space have not been adjusted, however, ligand distribution becomes uneven and multiple bonds with the receptor diminishes mapping accuracy. Therefore the present invention presents versatile uses in studying ligand-receptor interactions.

Cell receptors can include but are not limited to small molecules, peptides, proteins, steroid hormone receptors, carbohydrates, lipids, membrane proteins, glycoproteins, glycolipids, lectin, neurotrophin receptors, DNA, and RNA. Any substance that exists on the cell surface and is capable of interaction with ligand fixed onto an AFM Tip surface can be used as a receptor.

Additionally, ligand types fixed onto the AFM Tip can include but are not limited to small molecules, peptides, proteins, steroids, carbohydrates, lipids, membrane proteins, neurotrophins, antibodies, DNA, RNA, and complex compounds. In other words, any substance that can be loaded onto an AFM Tip and is observable by interaction with receptors can be used as ligands.

Figure 16:
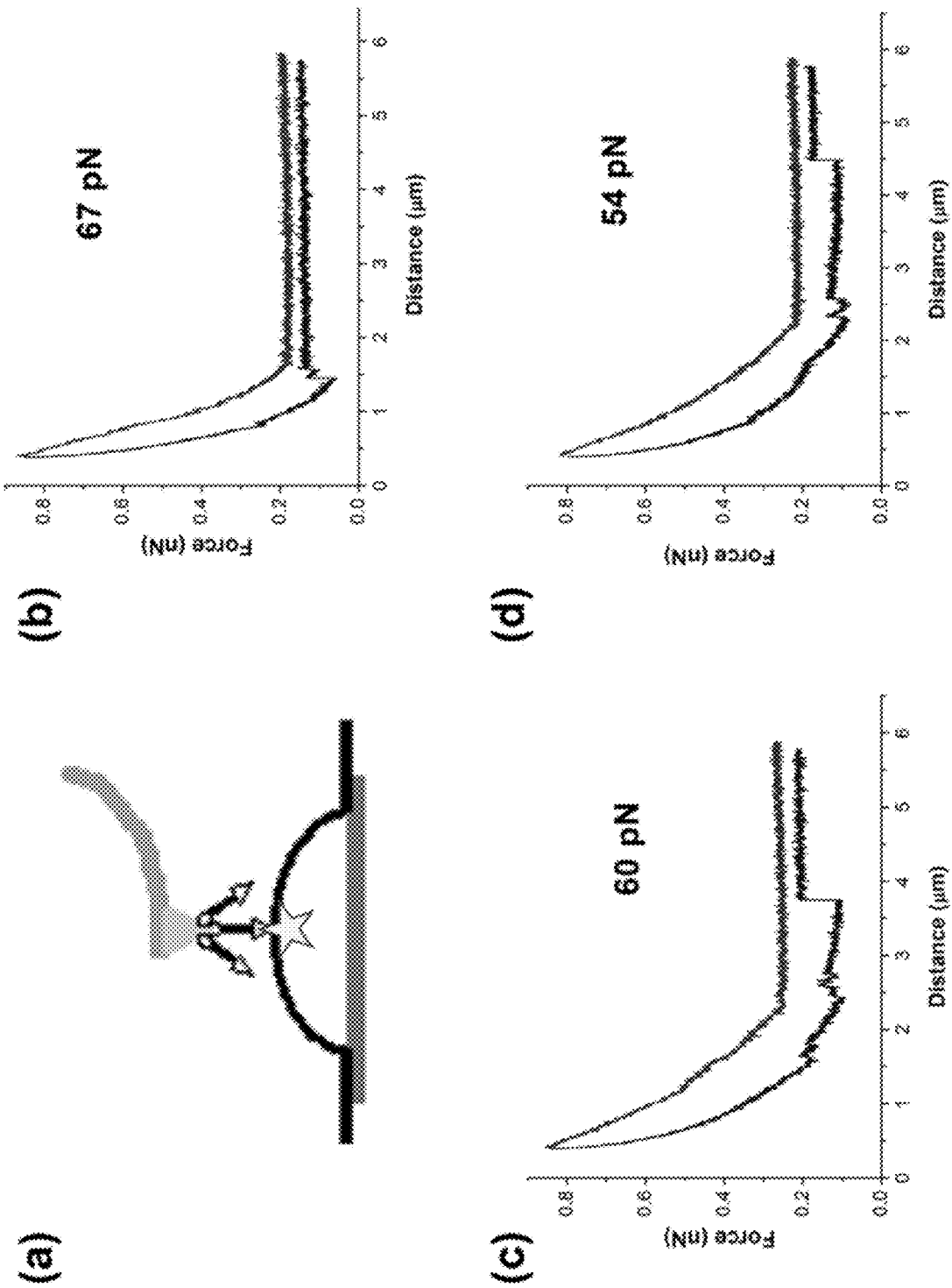
FIG. 16a shows a schematic view of the method of screening the receptors on a cell with a ligand-coated AFM tip.
FIGS. 16b-16d show the force curves for the interaction between FPR1 and its biding peptide.
Figure 17:
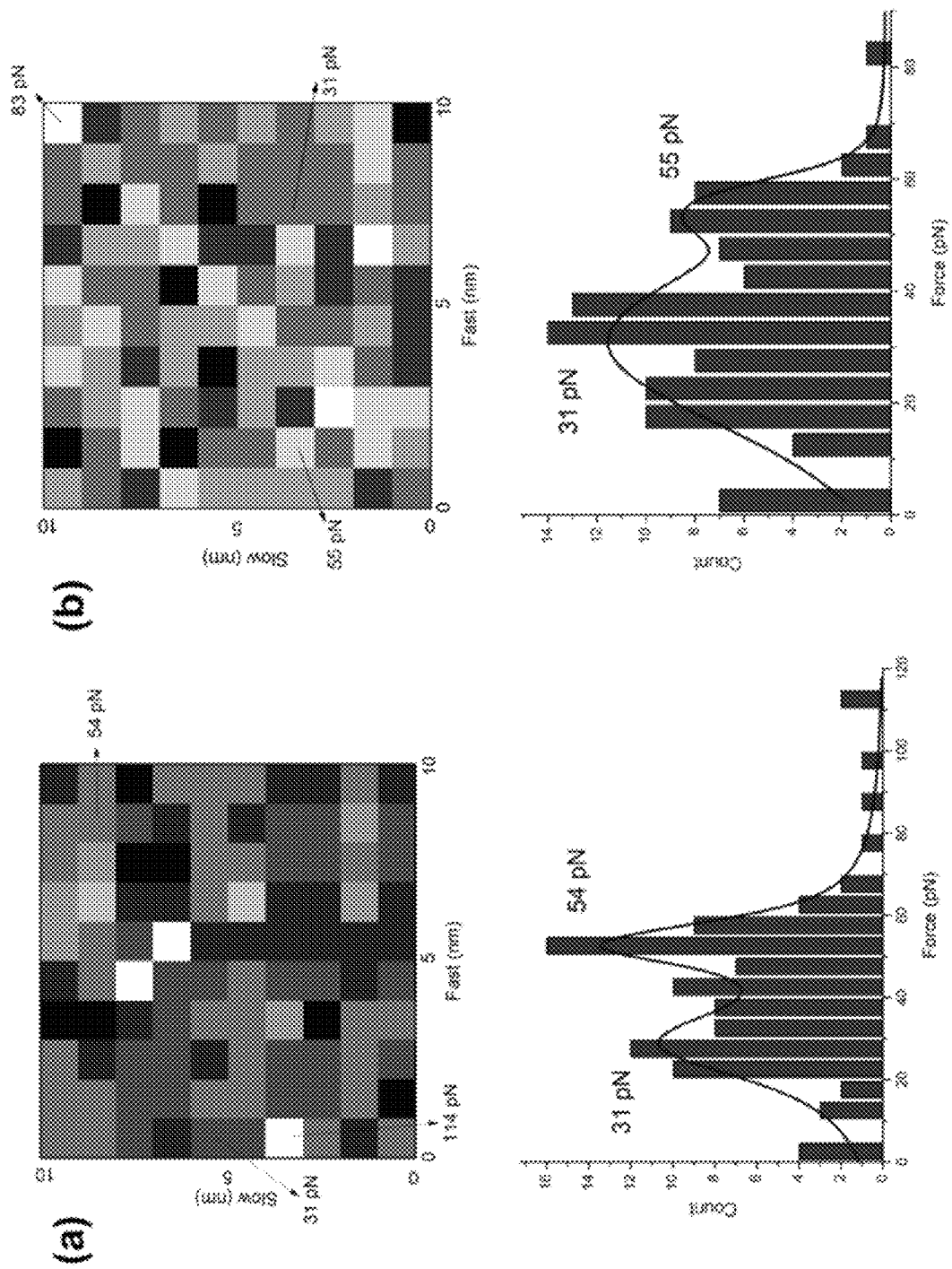
FIGS. 17a-17b show the force map and histogram for the interaction between FPR1 and its biding peptide on each different area of a cell.

In Examples 11 to 15, and FIGS. 16 to 18 of the present invention, peptide-protein interactions, carbohydrate-glycolipid interactions, lectin-glycoprotein interactions, carbohydrate-glycoprotein interactions, and neurotrophin-neurotrophin receptor interactions were surveyed.

The present invention is further explained in more detail with reference to the following examples. These examples, however, should not be interpreted as limiting the scope of the present invention in any manner.

PREPARATION EXAMPLES

Numbering scheme is used for compounds throughout the Examples such as compound 1, compound 2, I, II, III, IV, V and so on. It is to be understood however, that the compound numbering scheme is consistent with and is confined to the particular Example section to which it is recited. For instance, compound 1 as recited in Example 2 may not necessarily be the same compound 1 as found in Example 3.

Example 1

Methods for Making Microarray Using Size-Controlled Macromolecule

Figure 2B:
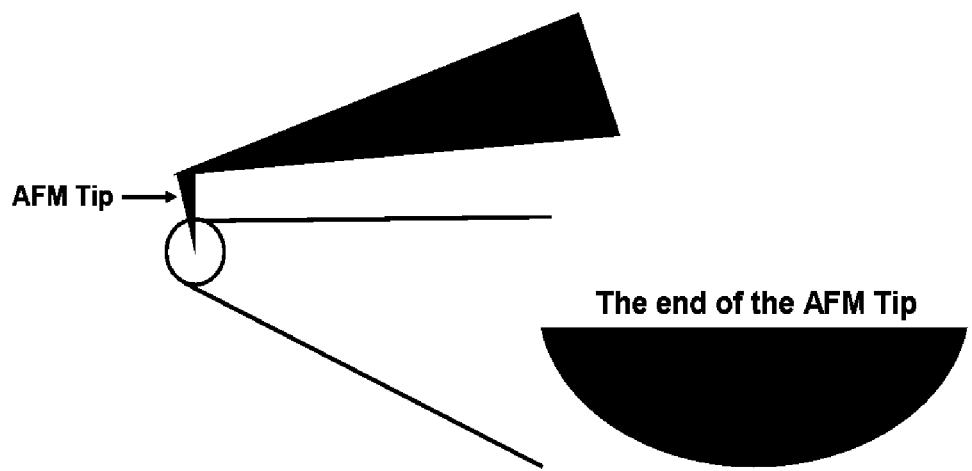
FIG. 2B shows an enlarged view of the tip of AFM cantilever in accordance with the exemplary embodiment of the present invention.
Figure 2C:
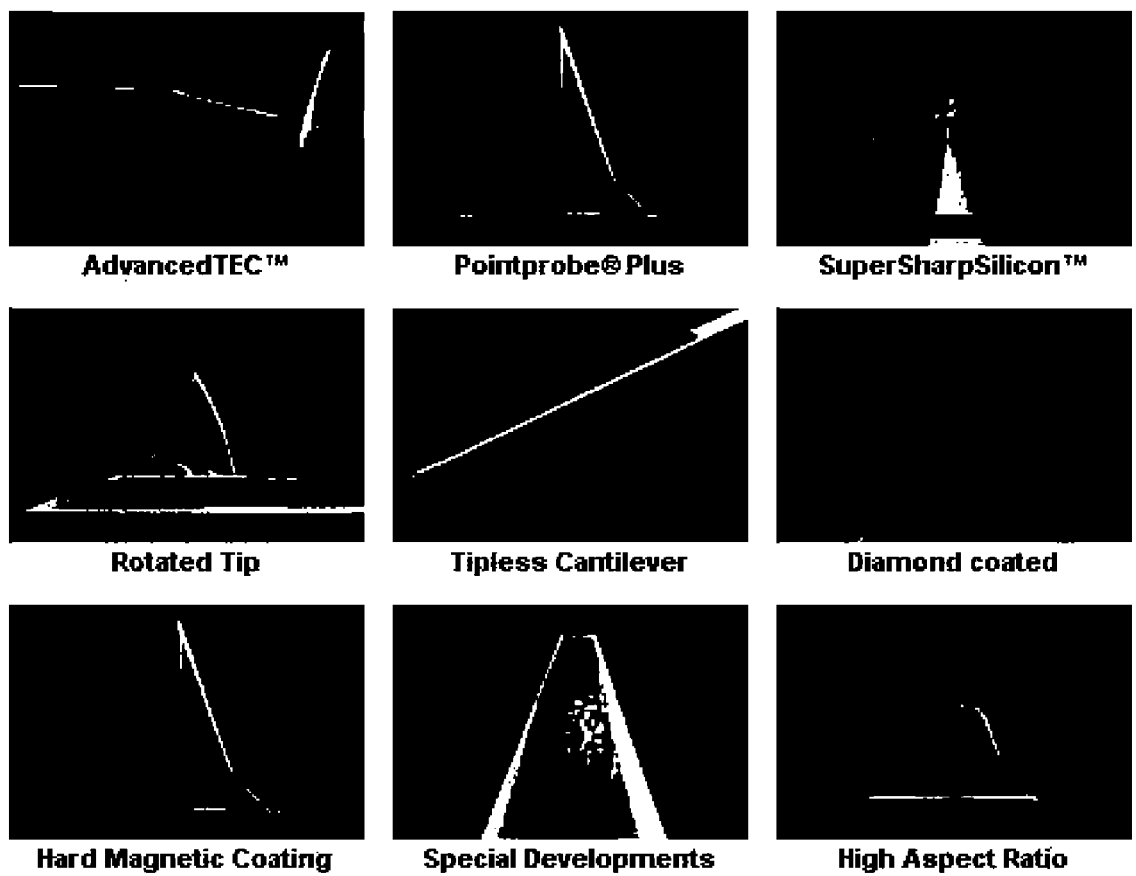
FIG. 2C shows a variety of commercially available AFM tip.

In Example 1, designations I, II, III, IV, and V refer to various compounds and intermediate compounds as shown in FIG. 2.

Example 1.1

Materials

The silane coupling reagents, (3-glycidoxypropyl)methyldiethoxysilane (GPDES) and (3-aminopropyl)diethoxymethylsilane (APDES), were purchased from Gelest, Inc. and all other chemicals were of reagent grade from Sigma-Aldrich. Reaction solvents for the silylation are anhydrous ones in Sure/Seal bottles from Aldrich. All washing solvents for the substrates are of HPLC grade from Mallinckrodt Laboratory Chemicals. The UV grade fused silica plates (30 mm×10 mm×1.5 mm) were purchased from CVI Laser Corporation. The polished prime Si(100) wafers (dopant, phosphorus; resistivity, 1.5-2.1 $\Omega\cdot$cm) were purchased from MEMC Electronic Materials, Inc. Glass slides (2.5×7.5 cm) were purchased from Corning Co. All of the oligonucleotides were purchased from Metabion. Ultrapure water (18 M $\Omega$/cm) was obtained from a Milli-Q purification system (Millipore).

Example 1.2

Instruments

The film thickness was measured with a spectroscopic ellipsometer (J. A. Woollam Co. Model M-44). UV-vis spectra were recorded on a Hewlett-Packard diodearray 8453 spectrophotometer. Tapping mode AFM experiments were performed with a Nanoscope IIIa AFM (Digital Instruments) equipped with an "E" type scanner.

Example 1.3

Cleaning the Substrates

Substrates such as oxidized silicon wafer, fused silica, and glass slide, were immersed into Piranha solution (conc. $H_2SO_4$:30% $H_2O_2$=7:3 (v/v)) and the reaction bottle containing the solution and the substrates was sonicated for an hour. (Caution: Piranha solution can oxidize organic materials explosively. Avoid contact with oxidizable materials.) The plates were washed and rinsed thoroughly with a copious amount of deionized water after the sonication. The clean substrates were dried in a vacuum chamber (30-40 mTorr) for the next steps.

Example 1.4

Preparing the Hydroxylated Substrates

The above clean substrates were soaked in 160 ml toluene solution with 1.0 ml (3-glycidoxypropyl)methyldiethoxysilane (GPDES) for 10 h. After the self-assembly, the substrates were washed with toluene briefly, placed in an oven, and heated at 110° C. for 30 min. The plates were sonicated in toluene, toluene-methanol (1:1 (v/v)), and methanol in a sequential manner for 3 min at each washing step. The washed plates were dried in a vacuum chamber (30-40 mTorr). GPDES-modified substrates were soaked in a neat ethylene glycol (EG) solution with two or three drops of 95% sulfuric acid at 80-100° C. for 8 h. After cooling, the substrates were sonicated in ethanol and methanol in a sequential manner each for 3 min. The washed plates were dried in a vacuum chamber (30-40 mTorr).

Example 1.5

Preparing the Dendron-Modified Substrates

The above hydroxylated substrates were immersed into a methylene chloride solution dissolving the dendron (1.2 mM) and a coupling agent, 1-[-3-(dimethylamino)propyl]-3-ethylcarbodiimide hydrochloride (EDC) or 1,3-dicyclohexylcarbodiimide (DCC) (11 mM) in the presence of 4-dimethylaminopyridine (DMAP) (0.82 mM). After 3 days at room temperature, the plates were sonicated in methanol, water, and methanol in a sequential manner each for 3 min. The washed plates were dried in a vacuum chamber (30-40 mTorr) for the next step.

Example 1.6

Preparing the NHS-Modified Substrates

The dendron-modified substrates were immersed into a methylene chloride solution with 1.0 M trifluoroacetic acid (TFA). After 3 h, they were again soaked in a methylene chloride solution with 20% (v/v) diisopropylethylamine (DIPEA) for 10 min. The plates were sonicated in methylene chloride and methanol each for 3 min. After being dried in a vacuum chamber, the deprotected substrates were incubated in the acetonitrile solution with di(N-succinimidyl)carbonate (DSC) (25 mM) and DIPEA (1.0 mM). After 4 h reaction under nitrogen atmosphere, the plates were placed in a stirred dimethylformamide solution for 30 min and washed briefly with methanol. The washed plates were dried in a vacuum chamber (30-40 mTorr) for the next step.

Example 1.7

Arraying Oligonucleotides on the NHS-Modified Substrates

Probe oligonucleotides in 50 mM NaHCO3 buffer (pH 8.5) were spotted side by side in a 4 by 4 format on the NHS-modified substrate. The microarray was incubated in a humidity chamber (80% humidity) for 12 h to give the amine-tethered DNA sufficient reaction time. Slides were then stirred in a hybridization buffer solution (2×SSPE buffer (pH 7.4) containing 7.0 mM sodium dodecylsulfate) at 37° C. for 1 h and in boiling water for 5 min to remove non-specifically bound oligonucleotides. Finally, the DNA-functionalized microarray was dried under a stream of nitrogen for the next step. For a fair comparison, different kinds of probes were spotted in a single plate.

Example 1.8

Hybridization

Hybridization was performed in the hybridization buffer solution containing a target oligonucleotide (1.0 nM) tagged with a Cy3 fluorescent dye at 50° C. for 1 h using a GeneTAC™ HybStation (Genomic Solutions, Inc.). The microarray was rinsed with the hybridization buffer solution in order to remove excess target oligonucleotide and dried with nitrogen. The fluorescence signal on each spot was measured with a ScanArray Lite (GSI Lumonics) and analyzed by Imagene 4.0 (Biodiscovery).

Example 1.9

Synthesis of the Dendron

Example 1.9.1

Preparation of 9-anthrylmethyl N-(3-carboxylpropyl)carbamate (I)—Compound I

4-Aminobutyric acid (0.50 g, 4.8 mmol, 1.0 equiv) and triethylamine (TEA) (1.0 ml, 7.3 mmol, 1.5 equiv) were dissolved in N,N-dimethylformamide (DMF) and stirred at 50° C. 9-Anthrylmethyl ρ-nitrophenyl carbonate (1.81 g, 4.8 mmol, 1.0 equiv) was slowly added while stirring. After stirring at 50° C. for 2 h, the solution was evaporated to dryness, and the solution was basified with 0.50 N sodium hydroxide (NaOH) solution. The aqueous solution was washed with ethyl acetate (EA), stirred in an ice bath and acidified with dilute hydrochloric acid (HCl). After the product was extracted with EA, the organic solution was dried with anhydrous $MgSO_4$, filtered and evaporated. The total weight of the resulting yellow powder was 1.06 g and the yield was 65%.

$^1$H NMR ($CDCl_3$)

δ 11.00-9.00 (br, $CH_2COOH$, 1H), 8.41 (s, $C_{14}H_9CH_2$, 1H), 8.31 (d, $C_{14}H_9CH_2$, 2H), 7.97 (d, $C_{14}H_9CH_2$, 2H), 7.51 (t, $C_{14}H_9CH_2$, 2H), 7.46 (t, $C_{14}H_9CH_2$, 2H), 6.08 (s, $C_{14}H_9CH_2O$, 2H), 5.01 (t, $OCONHCH_2$, 1H), 3.23 (q, $NHCH_2CH_2$, 2H), 2.34 (t, $CH_2CH_2COOH$, 2H), 1.77 (m, $CH_2CH_2CH_2$, 2H).

$^{13}$C NMR (CDCl3)

δ 178.5 ($CH_2COOH$), 157.9 (OCONH), 132.1 ($C_{14}H_9CH_2$), 131.7 ($C_{14}H_9CH_2$), 129.7 ($C_{14}H_9CH_2$), 129.7 ($C_{14}H_9CH_2$), 127.3 ($C_{14}H_9CH_2$), 126.8 ($C_{14}H_9CH_2$), 125.8 ($C_{14}H_9CH_2$), 124.6 ($C_{14}H_9CH_2$), 60.2 ($C_{14}H_9CH_2$), 41.0 ($NHCH_2CH_2$), 31.7 ($CH_2CH_2COOH$), 25.6 ($CH_2CH_2CH_2$).

Example 1.9.2

Preparation of 9-anthrylmethyl N-{[(tris{[2-(methoxycarbonyl)ethoxy]methyl}methyl)amino]carbonyl}propylcarbonate (II)—Compound II 9-Anthrylmethyl N-(3-carboxylpropyl)carbamate (0.65 g, 1.93 mmol, 1.5 equiv), 1-[3-(dimethylamino)propyl]-3-ethylcarbodiimide hydrochloride (EDC) (0.37 g, 1.93 mmol, 1.5 equiv), and 1-hydroxybenzotriazole hydrate (HOBT) (0.261 g, 1.93 mmol, 1.5 equiv) were dissolved in acetonitrile and stirred at room temperature. Tris{[(methoxycarbonyl)ethoxy]methyl}aminomethane (0.49 g, 1.29 mmol, 1.0 equiv) dissolved in acetonitrile was added with stirring, After stirring at room temperature for 12 h, the acetonitrile was evaporated. The crude product was dissolved in EA and washed with 1.0 N HCl and saturated sodium bicarbonate solution. After being dried with anhydrous $MgSO_4$, filtered, and evaporated, the crude product was loaded in a column packed with silica gel. Purification by column chromatography (eluent:ethyl acetate:hexane=5:1 (v/v)) resulted in a viscous yellow liquid. The total weight of the yellow liquid was 0.67 g, and the yield was 74%.

$^1$H NMR ($CDCl_3$)

δ 8.43 (s, $C_{14}H_9CH_2$, 1H), 8.36 (d, $C_{14}H_9CH_2$, 2H), 7.99 (d, $C_{14}H_9CH_2$, 2H), 7.53 (t, $C_{14}H_9CH_2$, 2H), 7.47 (t, $C_{14}H_9CH_2$, 2H), 6.15 (s, CONHC, 1H), 6.08 (s, $C_{14}H_9CH_2O$, 2H), 5.44 (t, $OCONHCH_2$, 1H), 3.63-3.55 (m, $CH_2OCH_2CH_2COOCH_3$, 21H), 3.27 (q, $NHCH_2CH_2$, 2H), 2.46 (t, $CH_2CH_2COOCH_3$, 6H), 2.46 (t, $CH_2CH_2CONH$, 2H), 1.81 (m, $CH_2CH_2CH_2$, 2H).

$^{13}$C NMR ($CDCl_3$)

δ173.2 ($CH_2CONH$), 172.7 ($CH_2COOCH_3$), 157.4 (OCONH), 132.9 ($C_{14}H_9CH_2$), 131.5 ($C_{14}H_9CH_2$), 129.5 ($C_{14}H_9CH_2$), 129.4 ($C_{14}H_9CH_2$}, 127.5 ($C_{14}H_9CH_2$), 127.0 ($C_{14}H_9CH_2$), 125.6 ($C_{14}H_9CH_2$), 124.7 ($C_{14}H_9CH_2$), 69.6 ($NHCCH_2O$), 67.2 ($C_{14}H_9CH_2$), 60.1 ($OCH_2CH_2$), 59.4 ($NHCCH_2$), 52.1 ($OCH_3$), 40.8 ($NHCH_2CH_2$), 35.1 ($OCH_2CH_2$), 34.7 ($CH_2CH_2CONH$), 26.3 ($CH_2CH_2CH_2$).

Anal. Calcd for $C_{36}H_{46}N_2O_{12}$.0.5 $H_2O$: C, 61.18; H, 6.65; N, 4.03. Found: C, 61.09; H, 6.69; N, 3.96.

Example 1.9.3

Preparation of 9-anthrylmethyl N-[({tris[(2-carboxyethoxy)methyl]methyl}amino)carbonyl]propylcarbamate (III)—Compound III 9-Anthrylmethyl N-{[(tris{[2-(methoxycarbonyl)ethoxy]methyl}methyl)amino]carbonyl}propyl-carbonate (0.67 g, 0.93 mmol) was dissolved in acetone (30 ml) and 0.20 N NaOH (30 ml, 6 mmol). After being stirred at room temperature for 1 d, the acetone was evaporated. The aqueous solution was washed with EA, stirred in an ice bath and acidified with dilute HCl. After the product was extracted with EA, the organic solution was dried with anhydrous $MgSO_4$, filtered and evaporated. Solidification in acetone and ether solution at −20° C. resulted in a yellow powder. The total weight of the final pale yellow powder was 0.54 g with a yield of 88%.

$^1$H NMR($CDCl_3$)

δ 11.00-9.00 (br, $CH_2COOH$, 3H}, 8.61 (s, $C_{14}H_9CH_2$, 1H}, 8.47 (d, $C_{14}H_9CH_2$, 2H), 8.11 (d, $C_{14}H_9CH_2$, 2H), 7.60 (t, $C_{14}H_9CH_2$, 2H}, $C_{14}H_9CH_2$, 2H), 6.63 (s, CONHC, 1H), 6.36 (t, $OCONHCH_2$, 1H), 6.12 (s, $C_{14}H_9CH_2O$, 2H). 3.40-363 (m, $CH_2OCH_2CH_2COOH$, 12H), 3.20 (q, $NHCH_2CH_2$, 2H), 2.52 (t, $CH_2CH_2COOH$, 6H), 2.17 (t, $CH_2CH_2CONH$, 2H), 1.75 (m, $CH_2CH_2CH_2$, 2H).

$^{13}$C NMR ($CDCl_3$)

δ 172.2 ($CH_2COOH$), 172.0 ($CH_2CONH$), 156.7 (OCONH), 131.2 ($C_{14}H_9CH_2$), 130.7 ($C_{14}H_9CH_2$), 128.6 ($C_{14}H_9CH_2$), 128.4 ($C_{14}H_9CH_2$), 127.3 ($C_{14}H_9CH_2$), 126.2 ($C_{14}H_9CH_2$), 124.8 ($C_{14}H_9CH_2$), 124.0 ($C_{14}H_9CH_2$), 68.6 ($NHCCH_2O$), 66.5 ($C_{14}H_9CH_2$), 59.5 ($OCH_2CH_2$), 58.0 ($NHCCH_2$), 40.0 ($NHCH_2CH_2$), 34.0 ($OCH_2CH_2$), 33.5 ($CH_2CH_2CONH$), 25.8 ($CH_2CH_2CH_2$).

Anal. Calcd for $C_{33}H_{40}N_2O_{12} \cdot 1.5 H_2O$: C, 57.97; H, 6.34; N, 4.10. Found: C, 57.89; H, 6.21; N, 4.09.

Example 1.9.4

Preparation of 9-anthrylmethyl N-[({tris[(2-{[(tris{[2-(methoxycarbonyl)ethoxy]methyl}(methyl)amino]carbonyl}ethoxy)methyl]methyl}amino)carbonyl]propylcarbamate (IV)—Compound IV 9-Anthrylmethyl N-[({tris[(2-carboxyethoxy)methyl]methyl}amino)carbonyl]propylcarbamate (0.54 g, 0.82 mmol, 1.0 equiv), EDC (0.55 g, 2.87 mmol, 3.5 equiv), and HOBT (0.39 g, 2.89 mmol, 3.5 equiv) were dissolved in acetonitrile and stirred at room temperature. Tris{[(methoxycarbonyl)ethoxy]methyl}aminomethane (0.96 g, 2.53 mmol, 3.1 equiv) dissolved in acetonitrile was added with stirring. After stirring at room temperature for 36 h, the acetonitrile was evaporated. The crude product was dissolved in EA and washed with 1.0 N HCl and saturated sodium bicarbonate solution. After drying with anhydrous $MgSO_4$, filtered, and evaporated, the crude product was loaded in a column packed with silica gel. Column purification (eluent:ethyl acetate:methanol=20:1 (v/v)) resulted in a viscous yellow liquid. The total weight of the yellow liquid was 1.26 g with an 88% yield.

$^1$H NMR ($CDCl_3$)

δ 8.47 (s, $C_{14}H_9CH_2$, 1H), 8.39 (d, $C_{14}H_9CH_2$, 2H), 8.02 (d, $C_{14}H_9CH_2$, 2H), 7.53 (t, $C_{14}H_9CH_2$, 2H), 7.47 (t, $C_{14}H_9CH_2$, 2H), 6.60 (s, $CH_2CH_2CH_2CONHC$, 1H), 6.13 (s, $OCH_2CH_2CONHC$, 3H), 6.11 (s, $C_{14}H_9CH_2O$, 2H), 5.79 (t, $OCONHCH_2$, 1H), 3.65-3.60 (m, $CH_2OCH_2CH_2CONH$, $CH_2OCH_2CH_2COOCH_3$, 75H), 3.29 (q, $NHCH_2CH_2$, 2H), 2.50 (t, $CH_2CH_2COOCH_3$, 18H), 2.36 (t, $OCH_2CH_2CONH$, 6H), 2.27 (t, $CH_2CH_2CH_2CONH$, 2H), 1.85 (m, $CH_2CH_2CH_2$, 2H).

$^{13}$C NMR ($CDCl_3$)

δ 173.3 ($OCH_2CH_2CONH$), 172.5 ($CH_2CH_2CH_2CONH$), 171.6 ($CH_2COOCH_3$), 157.2 (OCONH), 131.8 ($C_{14}H_9CH_2$), 131.5 ($C_{14}H_9CH_2$), 129.4 ($C_{14}H_9CH_2$), 129.3 ($C_{14}H_9CH_2$), 127.6 ($C_{14}H_9CH_2$), 127.0 ($C_{14}H_9CH_2$), 125.6 ($C_{14}H_9CH_2$), 124.7 ($C_{14}H_9CH_2$), 69.5 ($NHCCH_2OCH_2CH_2COOCH_3$), 67.9 ($NHCCH_2OCH_2CH_2CONH$), 67.2 ($C_{14}H_9CH_2$), 60.3 ($OCH_2CH_2CONH$), 60.2 ($OCH_2CH_2COOCH_3$), 59.2 ($NHCCH_2OCH_2CH_2COOCH_3$, $NHCCH_2OCH_2CH_2CONH$), 52.1 ($OCH_3$), 41.0 ($NHCH_2CH_2$), 37.6 ($OCH_2CH_2CONH$), 35.1 ($OCH_2CH_2COOCH_3$), 34.7 ($CH_2CH_2CH_2CONH$), 26.3 ($CH_2CH_2CH_2$).

Anal. Calcd for $C_{81}H_{121}N_5O_{36} \cdot H_2O$: C, 55.31; H, 7.05; N, 3.98. Found: C, 55.05; H, 7.08; N, 4.04.

MALDI-TOF-MS: 1763.2 (MNa+), 1779.2 (MK+).

Example 1.9.5

Preparation of 9-anthrylmethyl N-({[tris({2-[({tris[(2-carboxyethoxy)methyl]methyl}amino)carbonyl]ethoxy}methyl)methyl]amino}carbonyl)propylcarbamate (V—Compound V 9-Anthrylmethyl N-[({tris[(2-{[(tris {[2-(methoxycarbonyl)ethoxy]methyl}methyl)amino]carbonyl}ethoxy)methyl]methyl}amino)carbonyl]propylcarbamate (0.60 g, 0.34 mmol) was dissolved in acetone (30 ml) and 0.20 N NaOH (30 ml). After stirring at room temperature for 1 d, the acetone was evaporated. The aqueous solution was washed with EA, stirred in an ice bath and acidified with dilute HCl. After the product was extracted with EA, the organic solution was dried with anhydrous $MgSO_4$, filtered and evaporated. The total weight of the final yellow powder was 0.37 g and the yield was 68%.

$^1$H NMR (DMSO)

δ 13.00-11.00 (br, $CH_2COOH$, 9H), 8.66 (s, $C_{14}H_9CH_2$, 1H), 8.42 (d, $C_{14}H_9CH_2$, 2H), 8.13 (d, $C_{14}H_9CH_2$, 2H), 7.62 (t, $C_{14}H_9CH_2$, 2H), 7.54 (t, $C_{14}H_9CH_2$, 2H), 7.12 (t, OCONHCH_2, 1H), 7.10 (s, $OCH_2CH_2CONHC$, 3H), 7.06 (s, $CH_2CH_2CH_2CONHC$, 1H), 6.06 (s, $C_{14}H_9CH_2O$, 2H), 3.57-3.55 (m, $CH_2OCH_2CH_2CONH$, $CH_2OCH_2CH_2COOH$, 48H), 3.02 (q, $NHCH_2CH_2$, 2H), 2.42 (t, $CH_2CH_2COOH$, 18H), 2.32 (t, $OCH_2CH_2CONH$, 6H), 2.11 (t, $CH_2CH_2CH_2CONH$, 2H), 1.60 (m, $CH_2CH_2CH_2$, 2H).

$^{13}$C NMR (DMSO)

δ 172.8 ($CH_2COOH$), 172.2 ($CH_2CH_2CH_2CONH$), 170.5 ($OCH_2CH_2CONH$), 156.5 (OCONH), 131.0 ($C_{14}H_9CH_2$), 130.6 ($C_{14}H_9CH_2$), 129.0 ($C_{14}H_9CH_2$), 128.7 ($C_{14}H_9CH_2$), 127.6 ($C_{14}H_9CH_2$), 126.7 ($C_{14}H_9CH_2$), 125.4 ($C_{14}H_9CH_2$), 124.3 ($C_{14}H_9CH_2$), 68.3 ($NHCCH_2OCH_2CH_2COOH$), 67.4 ($NHCCH_2OCH_2CH_2CONH$), 66.8 ($C_{14}H_9CH_2$), 59.8 ($OCH_2CH_2COOH$), 59.6 ($OCH_2CH_2CONH$), 57.9 ($NHCCH_2OCH_2CH_2CONH$), 55.9 ($NHCCH_2OCH_2CH_2COOH$), 36.4 ($NHCH_2CH_2$), 34.6 ($OCH_2CH_2COOH$), 30.8 ($OCH_2CH_2CONH$), 29.7 ($CH_2CH_2CH_2CONH$), 25.9 ($CH_2CH_2CH_2$).

Preparation Example 2

Methods of Producing Alternative Starting Material Dendron Macromolecule—Fmoc-Spacer-[9]-Acid In Example 2, various indicated compounds are referred to as compound 1, 2 and so forth.

First, a spacer, 6-azidohexylamine (1) from 1,6-dibromohexane was synthesized according to Lee, J. W.; Jun, S. I.; Kim, K. *Tetrahedron Lett.*, 2001, 42, 2709.

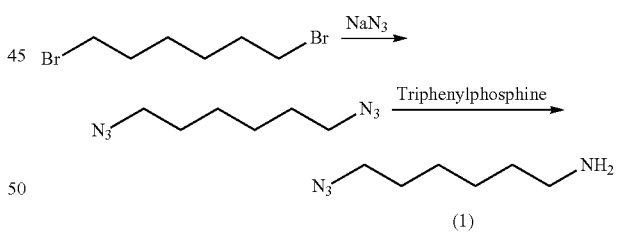

This spacer was attached to repeating unit (2) through unsymmetric urea formation and made $N_3$-spacer-[3]ester (3). The repeating unit was synthesized by condensation of TRIS with tert-butyl acrylate, which had been reported in Cardona, C. M.; Gawley, R. E. *J. Org. Chem.* 2002, 67, 141.

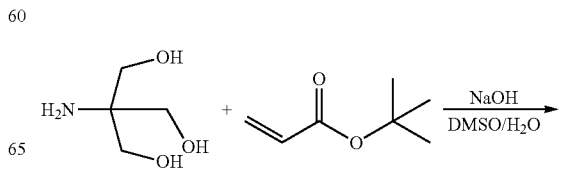

-continued

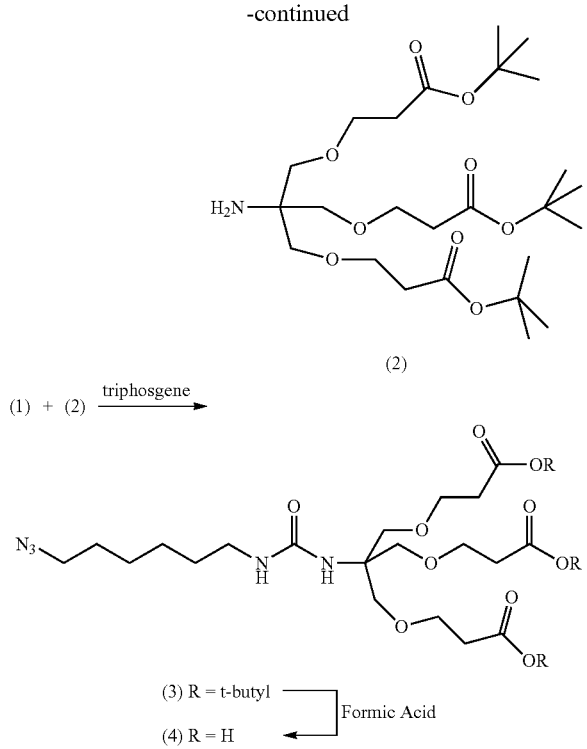

This triester was transformed to N₃-spacer-[3]acid (4) through hydrolysis and coupled with triester (2) under peptide coupling conditions, which led to N₃-spacer-[9]ester. After reduction of azide to amine and protection of amine with Fmoc group, hydrolysis of nonaester afforded Fmoc-spacer-[9]acid (5).

N-(6-Azidohexyl)-N'-tris {[2-(tert-butoxycarbonyl)ethoxy]methyl}-methylurea (3)

Triphosgene (1.3 g, 4.3 mmol) was dissolved in anhydrous $CH_2Cl_2$ (20 mL). A mixture of 6-azidohexylamine (1) (1.6 g, 12 mmol) and N,N-diisopropylethylamine (DIEA, 2.4 mL, 13.8 mmol) in anhydrous $CH_2Cl_2$ (35 mL) was added dropwise to the stirred solution of triphosgene over a period of 7 h using a syringe pump. After further stirring for 2 h, a solution of (2) (6.4 g, 13 mmol) and DIEA (2.7 mL, 15.2 mmol) in anhydrous $CH_2Cl_2$ (20 mL) was added. The reaction mixture was stirred for 4 h at room temperature under nitrogen, and washed with 0.5 M HCl and brine. The organic layer was then dried over anhydrous $MgSO_4$, and the solvent was removed by evacuation. Purification with column chromatography (silica, 1:1 EtOAc/hexane) yielded colorless oil (3.0 g, 40%).

$^1$H NMR (CDCl₃, 300 MHz): δ 1.45 (s, (CH₃)₃C, 27H); 1.36-1.58 (m, CH₂CH₂CH₂CH₂, 8H); 2.46 (t, CH₂CH₂O, J=6.4 Hz, 6H); 3.13 (m, CONHCH₂, 2H); 3.26 (t, N₃CH₂, J=6.9 Hz, 2H); 3.64-3.76 (m, CCH₂O and CH₂CH₂O, 12H); 5.00 (t, CH₂NHCO, J=6.7 Hz, 1H); 5.29 (s, CONHC, 1H).

$^{13}$C NMR (CDCl₃, 75 MHz): δ 26.52, 26.54, 28.81, 30.26 (CH₂CH₂CH₂CH₂); 28.14 ((CH₃)₃C); 36.20 (CH₂CH₂O); 39.86 (CONHCH₂); 51.40 (N₃CH₂); 58.81 (CCH₂O); 67.16 (CH₂CH₂O); 69.23 (CCH₂O); 80.58 ((CH₃)₃C); 157.96 (NHCONH); 171.26 (COOt-Bu).

FAB-MS: 674.26 (M⁺).

N-(6-Azidohexyl)-N'-tris {[2-carboxyethoxy]methyl}methylurea (4)

N₃-spacer-[3]ester (3) (0.36 g, 0.56 mmol) was stirred in 6.6 mL of 96% formic acid for 24 h. The formic acid was then removed at reduced pressure at 50° C. to produce colorless oil in a quantitative yield.

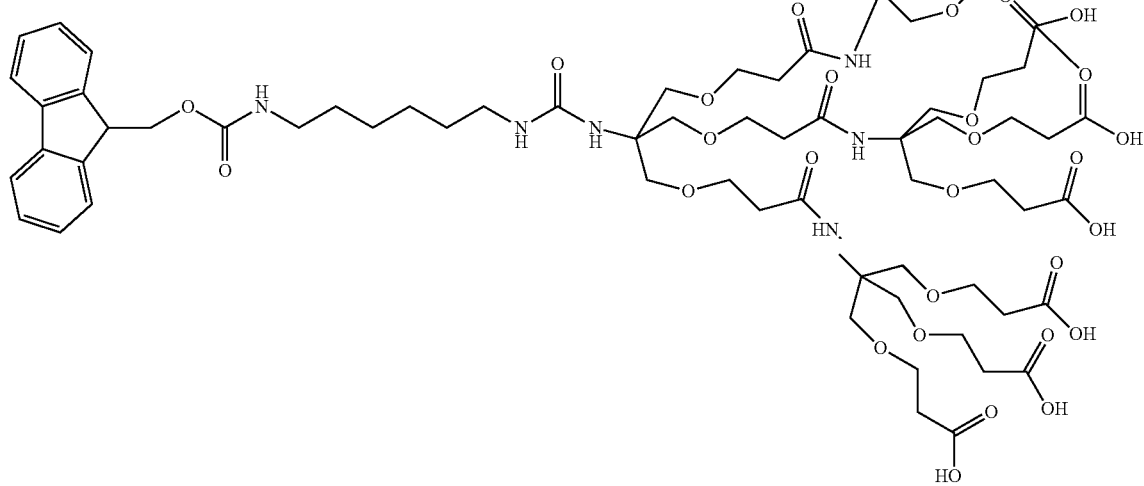

(5)

¹H NMR (CD₃COCD₃, 300 MHz): δ 1.34-1.60 (m, CH₂CH₂CH₂CH₂, 8H); 2.53 (t, CH₂CH₂O, J=6.4 Hz, 6H); 3.07 (t, CONHCH₂, J=6.9 Hz, 2H), 3.32 (t, N₃CH₂, J=6.9 Hz, 2H), 3.67-3.73 (m, CCH₂O and CH₂CH₂O, 12H).

¹³C NMR (CD₃COCD₃, 75 MHz): δ 27.21, 29.54, 31.02 (CH₂CH₂CH₂CH₂); 35.42 (CH₂CH₂O); 40.27 (CONHCH₂); 52.00 (N₃CH₂); 59.74 (CCH₂O); 67.85 (CH₂CH₂O); 70.96 (CCH₂O); 158.96 (NHCONH); 173.42 (COOH).

FAB-MS: 506.19 (MH⁺).

N-(6-Azidohexyl)-N'-tris[(2-{[(tris {[2-(tert-butoxy-carbonyl)ethoxy]-methyl}methyl)amino]carbonyl}ethoxy)methyl]methylurea (4.1)

The HOBt (0.20 g, 1.5 mmol), DIEA (0.30 mL, 1.8 mmol), and EDC (0.33 g, 1.8 mmol) were added to (4) (0.25 g, 0.50 mmol) in 5.0 mL of dry acetonitrile. Then, the amine (2) (1.14 g, 2.3 mmol) dissolved in 2.5 mL of dry acetonitrile was added, and the reaction mixture was stirred under N₂ for 48 h. After removal of the solvent at reduced pressure, the residue was dissolved in MC and washed with 0.5 M HCl and brine. The organic layer was then dried over MgSO₄, the solvent was removed in vacuo, and column chromatography (SiO2, 2:1 EtOAc/hexane) yielded a colorless oil (0.67 g, 70%).

¹H NMR (CDCl₃, 300 MHz): δ 1.45 (s, (CH₃)₃C, 81H); 1.36-1.58 (m, CH₂CH₂CH₂CH₂, 8H); 2.40-2.47 (m, CH₂CH₂O gen. 1 & 2, 24H); 3.13 (m, CONHCH₂, 2H), 3.26 (t, N₃CH₂, 6.9 Hz, 2H), 3.62-3.69 (m, CCH₂O gen. 1 & 2, CH₂CH₂O gen. 1 & 2, 48H); 5.36 (t, CH₂NHCO, J=6.7 Hz, 1H), 5.68 (br, CONHC, 1H), 6.28 (br, amide NH, 3H).

¹³C NMR (CDCl₃, 75 MHz): δ 26.59, 26.69, 28.91, 30.54 (CH₂CH₂CH₂CH₂); 28.22 ((CH₃)₃C); 36.20 (CH₂CH₂O gen. 2); 37.43 (CH₂CH₂O gen. 1); 39.81 (CONHCH₂); 51.47 (N₃CH₂); 58.93 (CCH₂O gen. 1); 59.89 (CCH₂O gen. 2); 67.15 (CH₂CH₂O gen. 2); 67.68 (CH₂CH₂O gen. 1); 69.23 (CCH₂O gen. 2); 70.12 (CCH₂O gen. 1); 80.57 ((CH₃)₃C); 158.25 (NHCONH); 171.01 (COOt-Bu) 171.41 (CONH amides).

MALDI-MS: 1989.8 (MNa⁺), 2005.8 (MK⁺).

N-(6-Aminohexyl)-N'-tris[(2-{[(tris{[2-(tert-butoxy-carbonyl)ethoxy]-methyl}methyl)amino]carbonyl}ethoxy)methyl]methylurea (4.2)

Nona-tert-butyl ester (4.1) (0.37 g, 0.20 mmol) was stirred with 10% Pd/C (37.0 mg) in ethanol (20.0 mL) under H₂ at room temperature for 12 h. After checking completion of the reaction with TLC, the mixture was filtered with a 0.2 μm Millipore filter. After the filter paper was rinsed with CH₂Cl₂, the combined solvent was removed in vacuo, and colorless oil was recovered.

N-{6-(9-fluorenylmethoxycarbonyl)aminohexyl}-N'-tris[(2-{[(tris{[2-(tert-butoxycarbonyl)ethoxy]methyl}methyl)amino]carbonyl}ethoxy)methyl]methylurea (4.3)

The amine (4.2) (0.33 g, 0.17 mmol) and DIEA (33 μL, 0.19 mmol) were dissolved in 5.0 mL of CH₂Cl₂, and stirred for 30 min under nitrogen atmosphere. 9-Fluorenylmethyl chloroformate (48 mg, 0.19 mmol) in 2.0 mL of CH₂Cl₂ was added, and the reaction mixture was stirred for 3 h at room temperature. The solvent was removed under reduced pressure and washed with 0.5 M HCl and brine. The residue was purified with column chromatography (silica, EtOAc) to yield colorless oil (0.18 g, 64%).

¹H NMR (CDCl₃, 300 MHz): δ 1.45 (s, (CH₃)₃C, 81H); 1.23-1.58 (m, CH₂CH₂CH₂CH₂, 8H); 2.37-2.47 (m, CH₂CH₂O gen. 1 & 2, 24H); 3.10-3.22 (m, CONHCH₂, 4H); 3.62-3.70 (m, CCH₂O gen. 1 & 2, CH₂CH₂O gen. 1 & 2, 48H); 4.22 (t, CH(fluorenyl)-CH₂, J=7.1 Hz, 1H); 4.36 (d, fluorenyl-CH₂, J=7.1 Hz, 2H); 5.27-5.35 (m, CH₂NHCO, 2H); 5.67 (br, CONHC, 1H); 6.25 (br, amide, 3H); 7.28-7.77 (fluorenyl, 8H).

¹³C NMR (CDCl₃, 75 MHz): δ 26.85, 27.02, 30.27, 30.88 (CH₂CH₂CH₂CH₂); 28.49 ((CH₃)₃C); 36.48 (CH₂CH₂O gen. 2); 37.73 (CH₂CH₂O gen. 1); 40.03, 41.34 (CONHCH₂); 47.68 (CH(fluorenyl)-CH₂); 59.22 (CCH₂O gen. 1); 60.16 (CCH₂O gen. 2); 66.87 (fluorenyl-CH₂); 67.43 (CH₂CH₂O gen. 2); 67.98 (CH₂CH₂O gen. 1); 69.52 (CCH₂O gen. 2); 70.42 (CCH₂O gen. 1); 80.84 ((CH₃)₃C); 120.28, 125.52, 127.38, 127.98, 141.65, 144.48 (fluorenyl); 156.88 (OCONH); 158.52 (NHCONH); 171.27 (COOt-Bu) 171.65 (amide CONH).

MALDI-MS: 2186.8 (MNa⁺), 2002.8 (MK⁺).

N-{6-(9-fluorenylmethoxycarbonyl)aminohexyl}-N'-tris[(2-{[(tris{[2-carboxyethoxy]methyl}methyl)amino]carbonyl}ethoxy)methyl]-methylurea (5)

Nona-tert-butyl ester having a protecting group (4.3) (0.12 g, 72 mmol) was stirred in 10 mL of 96% formic acid for 18 h. The formic acid was then removed at reduced pressure at 50° C. to produce colorless oil in a quantitative yield.

¹H NMR (CD₃COCD₃, 300 MHz): δ 1.23-1.51 (m, CH₂CH₂CH₂CH₂, 8H); 2.44-2.58 (m, CH₂CH₂O gen. 1 & 2, 24H); 3.15-3.18 (m, CONHCH₂, 4H); 3.61-3.75 (m, CCH₂O gen. 1 & 2, CH₂CH₂O gen. 1 & 2, 48H); 4.23 (t, CH(fluorenyl)-CH₂, J=7.0 Hz, 1H); 4.35 (d, fluorenyl-CH₂, J=7.0 Hz, 2H); 5.85, 6.09 (br, CH₂NHCO, 2H); 6.57 (br, CONHC, 1H); 6.88 (br, amide NH, 3H); 7.31-7.88 (fluorenyl, 8H).

¹³C NMR (CD₃COCD₃, 75 MHz): δ 27.21, 27.33, 30.69, 30.98 (CH₂CH₂CH₂CH₂); 35.31 (CH₂CH₂O gen. 2); 37.83 (CH₂CH₂O gen. 1); 40.56, 41.54 (CONHCH₂); 48.10 (CH (fluorenyl)-CH₂); 59.93 (CCH₂O gen. 1); 61.10 (CCH₂O gen. 2); 66.86 (fluorenyl-CH₂); 67.81 (CH₂CH₂O gen. 2); 68.37 (CH₂CH₂O gen. 1); 69.80 (CCH₂O gen. 2); 70.83 (CCH₂O gen. 1); 120.84, 126.13, 127.98, 128.56, 142.10, 145.16 (fluorenyl); 157.50 (OCONH); 159.82 (NHCONH); 173.20 (amide CONH); 173.93 (COOH).

Example 3

Additional Dendron Compounds

It is to be noted that while a particular protecting group may be shown with a macromolecule, the compounds are not limited to the specific protecting groups shown. Moreover, while various chains and spacers are depicted indicating an exact molecular structure, modifications are possible according to accepted chemical modification methods to achieve the function of a density controlled, preferably low density, array on a substrate surface. As a point of reference for the shorthand description of the compounds, the left most letter(s) indicates the protecting group; the numeral in brackets indicates the number of branched termini; and the right most chemical entity indicates the chemistry on the branched termini. For example, "A-[27]-acid" indicates anthrylmethyl protecting group; 27 termini, and acid groups at the termini.

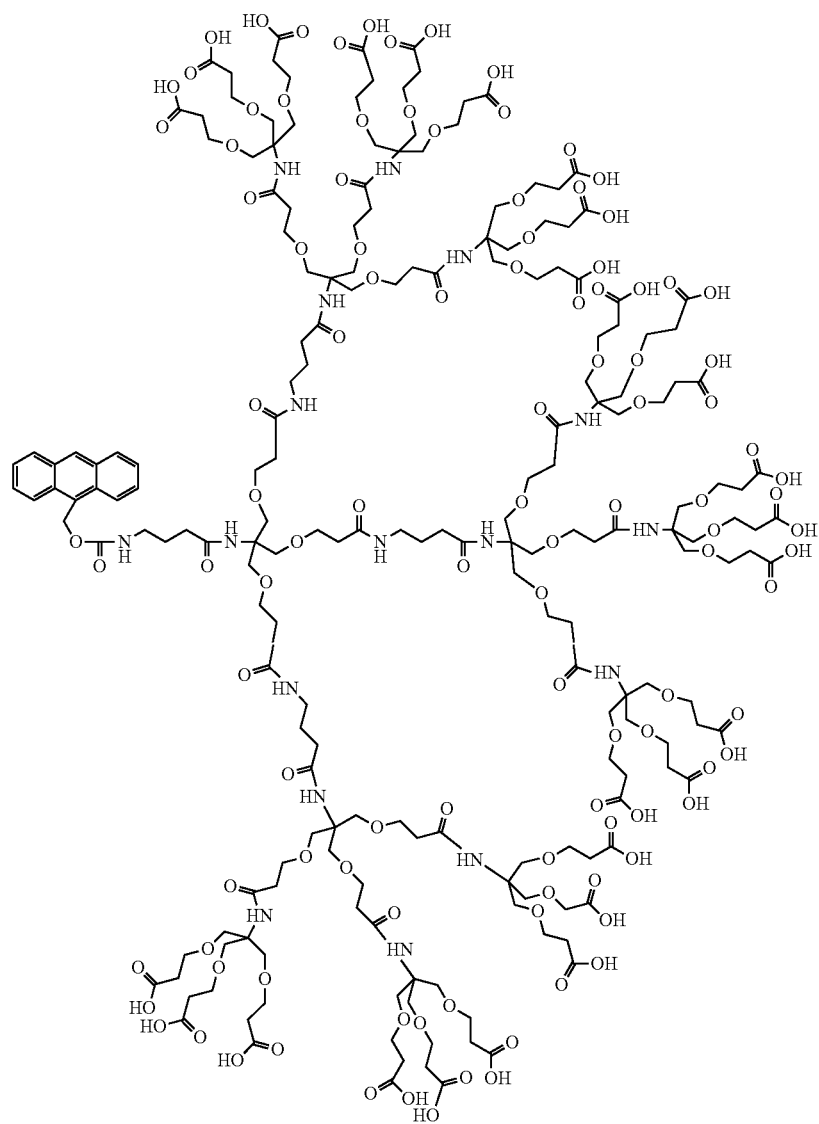
A-[27]-acid
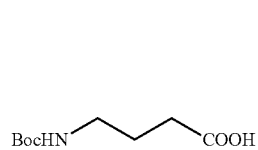
Boc-[1]-acid
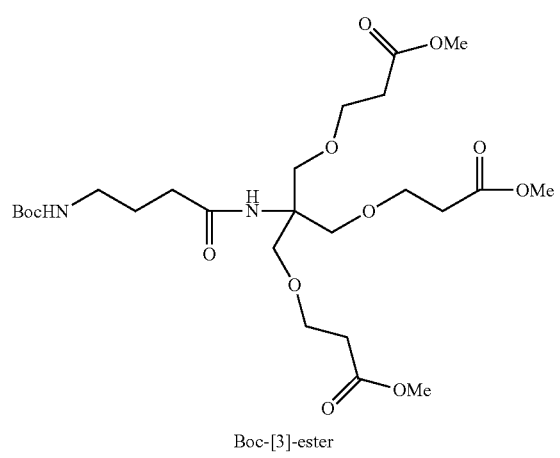
Boc-[3]-ester

33
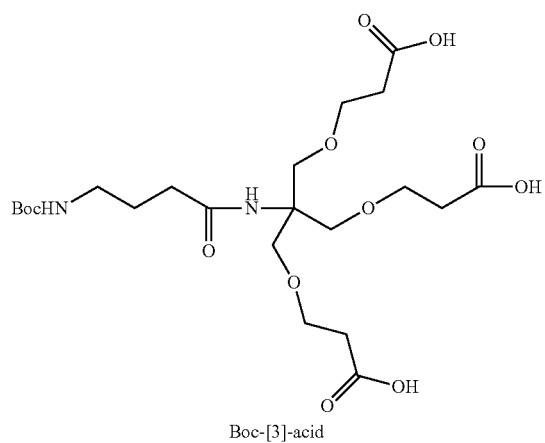
Boc-[3]-acid
34
-continued
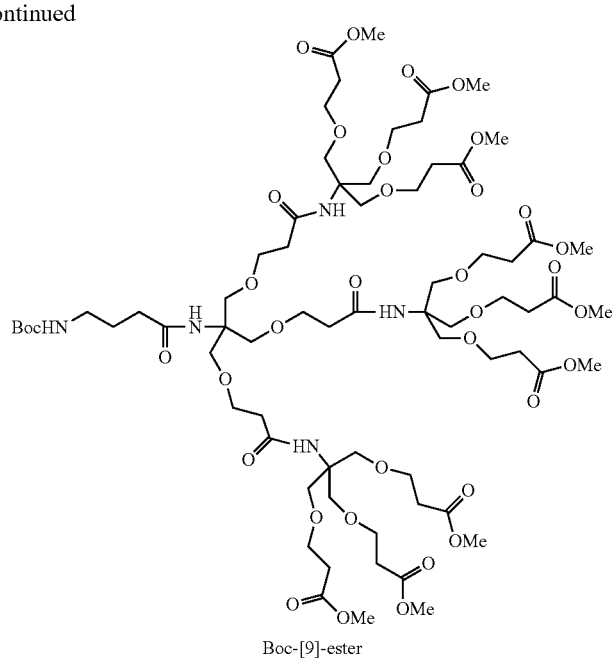
Boc-[9]-ester
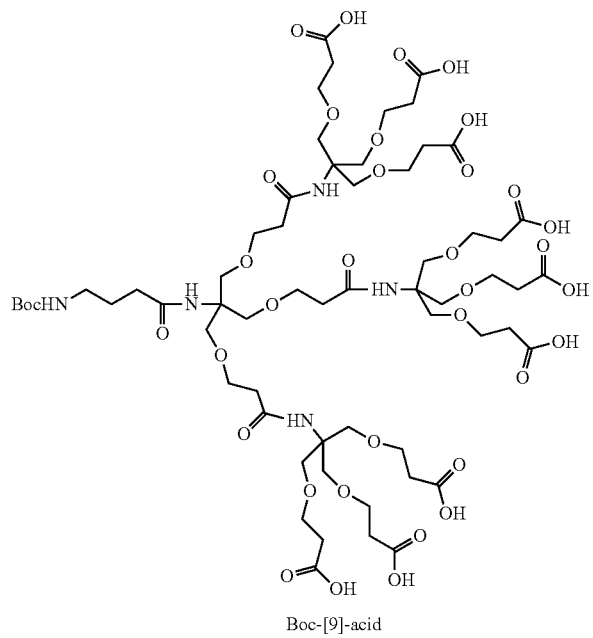
Boc-[9]-acid
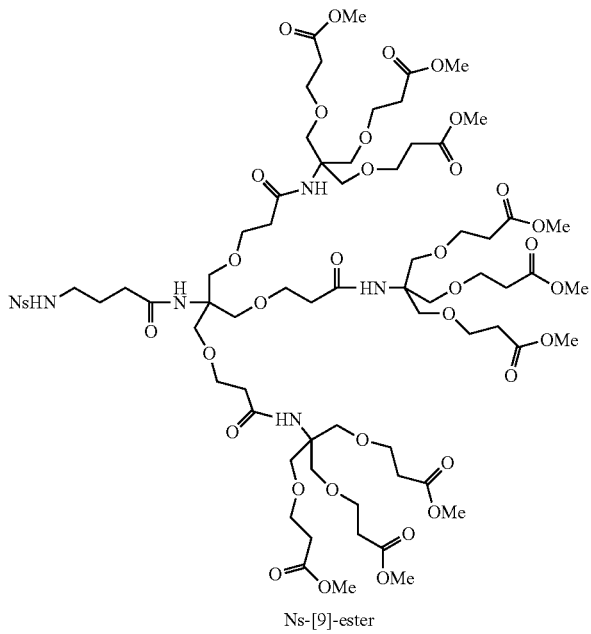
Ns-[9]-ester

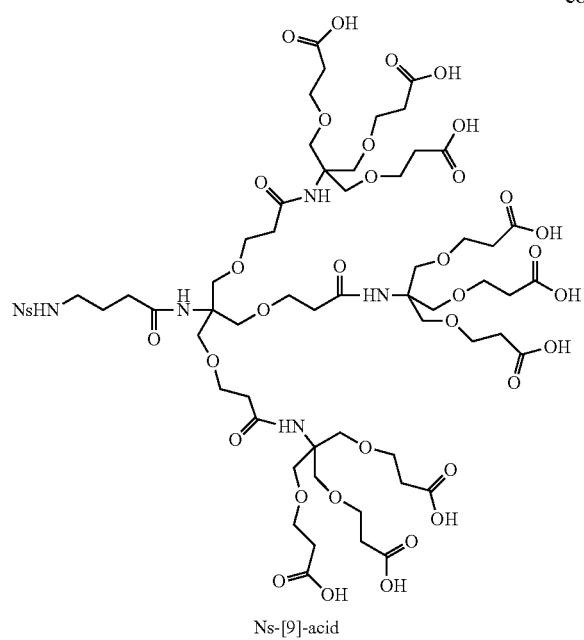
Ns-[9]-acid
Ns: 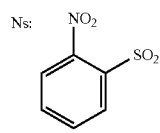
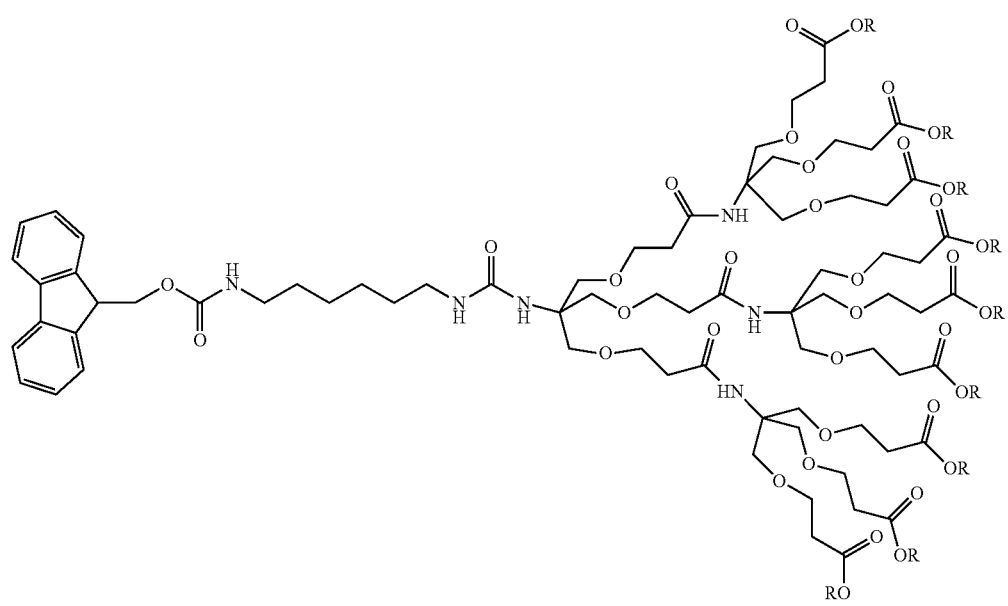
Fmoc-[9]-ester (R = t-butyl)

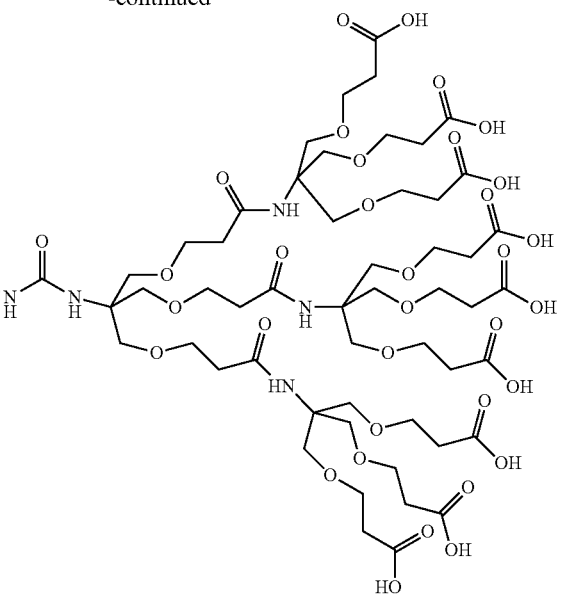
Fmoc-[9]-acid
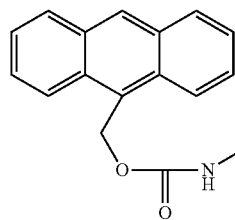
AE-[1]-acid
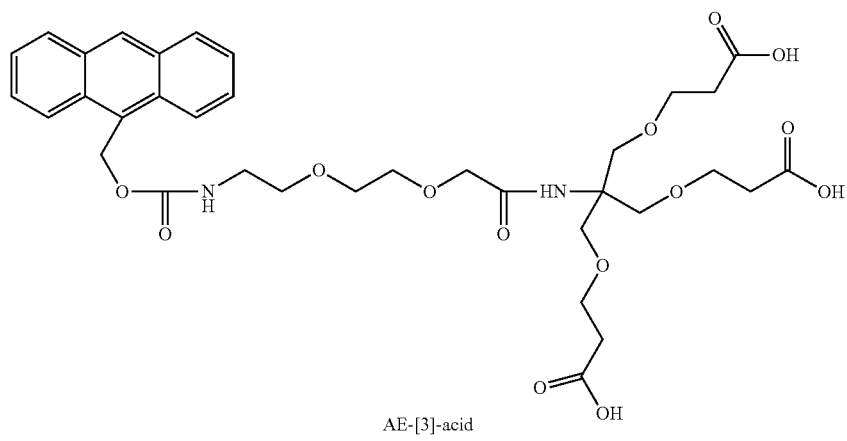
AE-[3]-acid

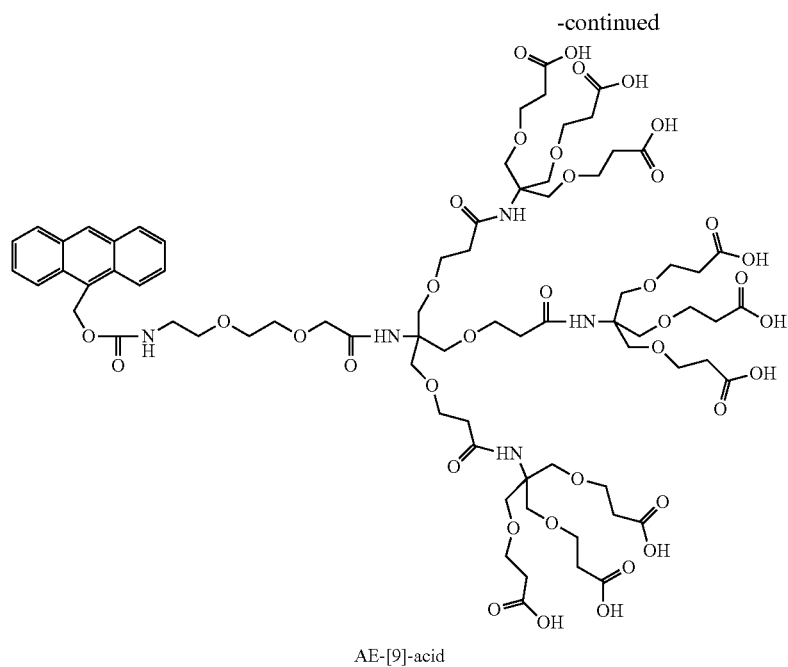
AE-[9]-acid
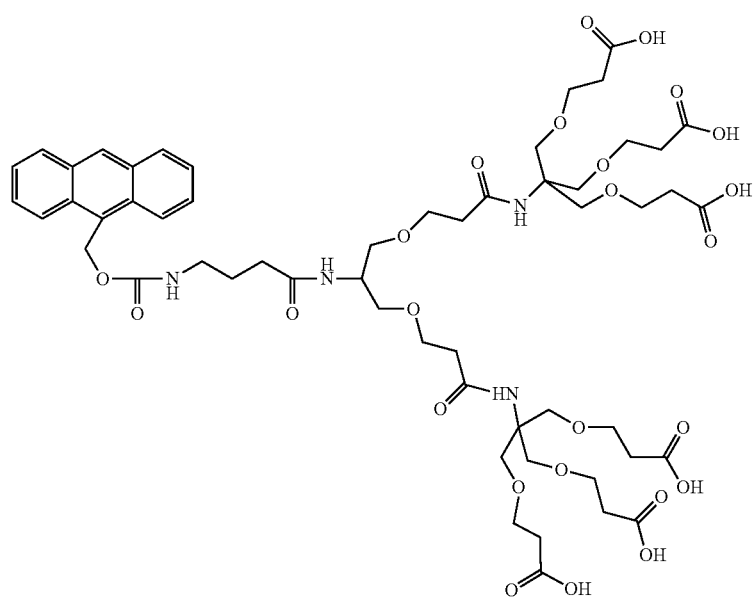
A-[6]-acid

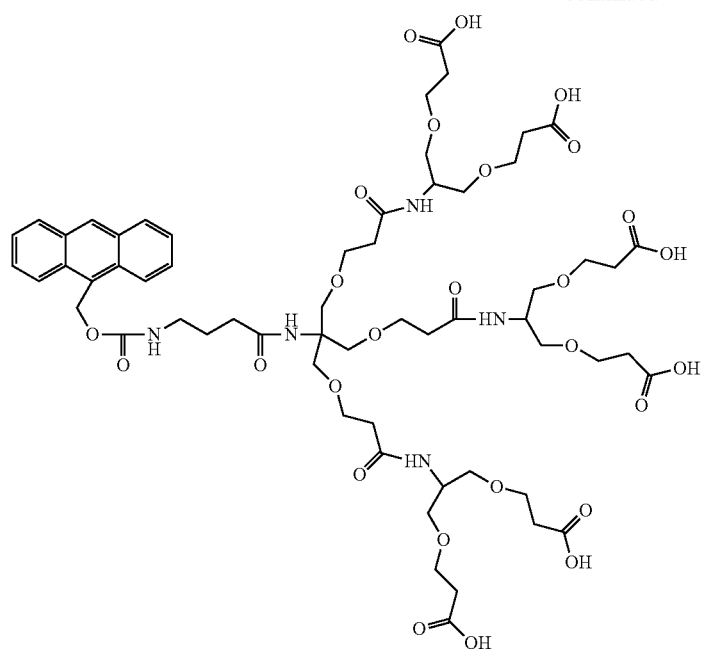
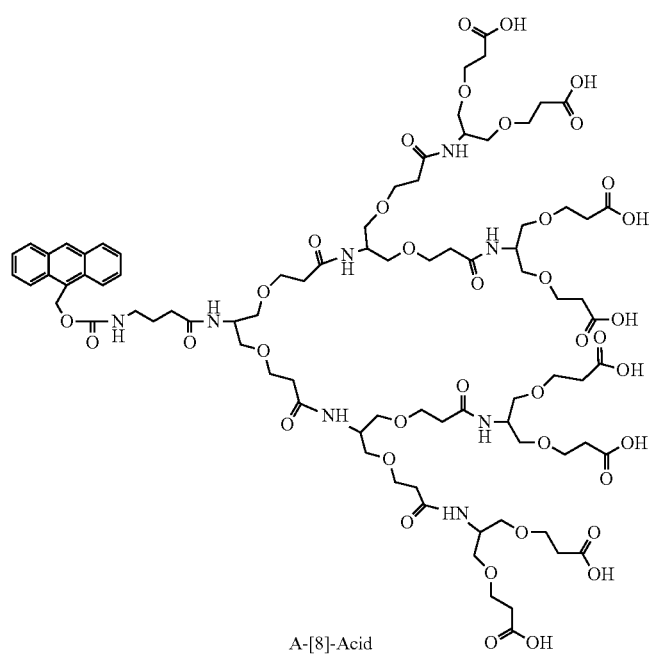
A-[8]-Acid

-continued
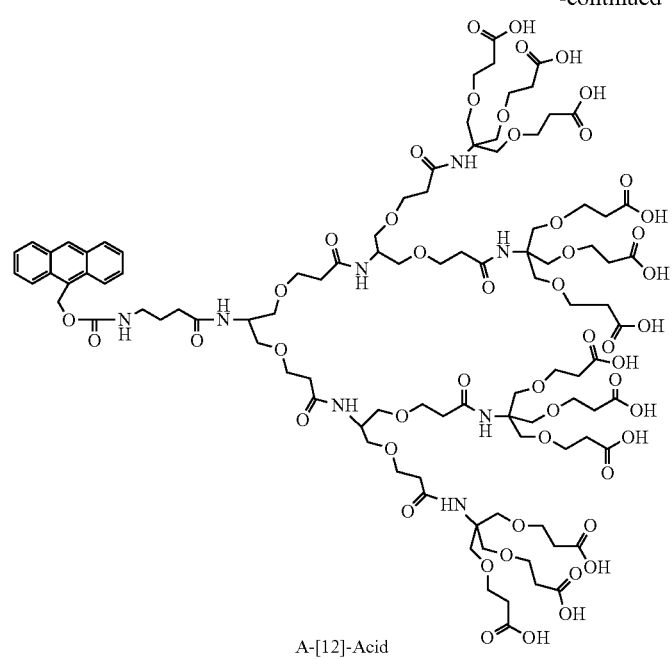
A-[12]-Acid
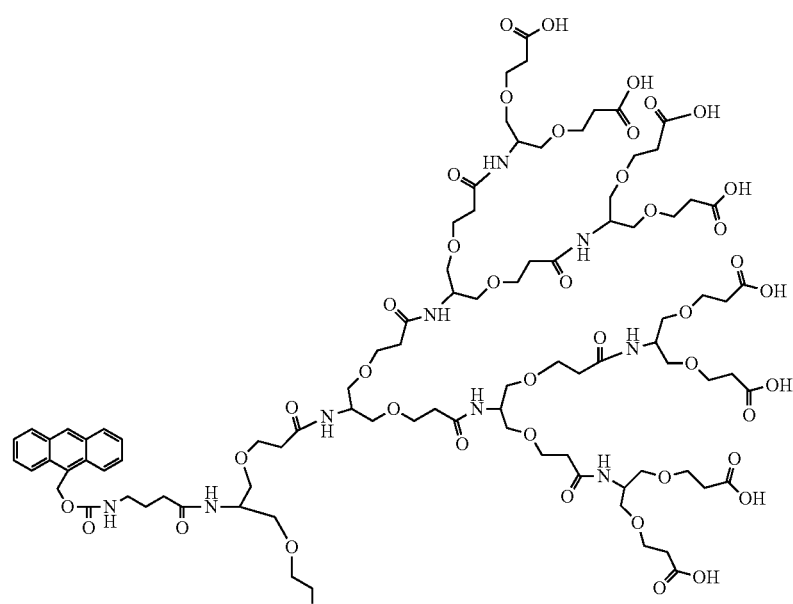

-continued
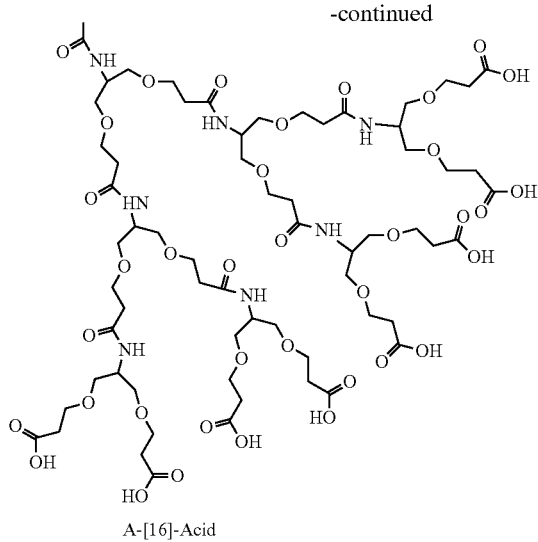
A-[16]-Acid
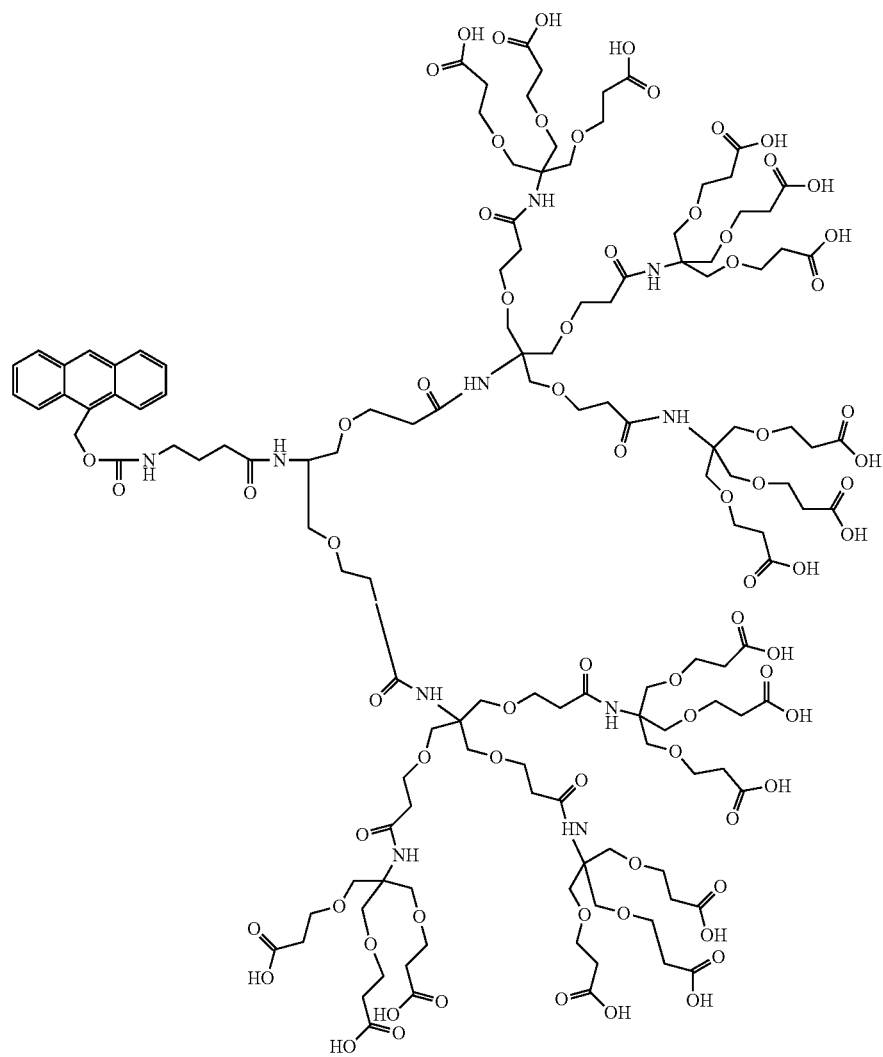
A-[18]-Acid

-continued
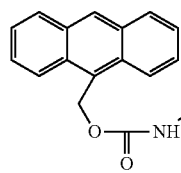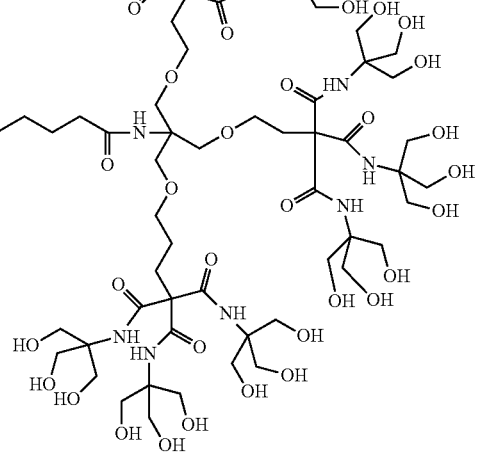
G.R. Newkome *J. Org. Chem.* 1985, 50, 2003
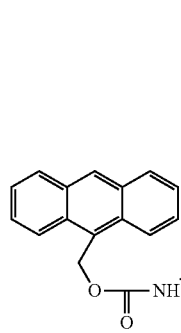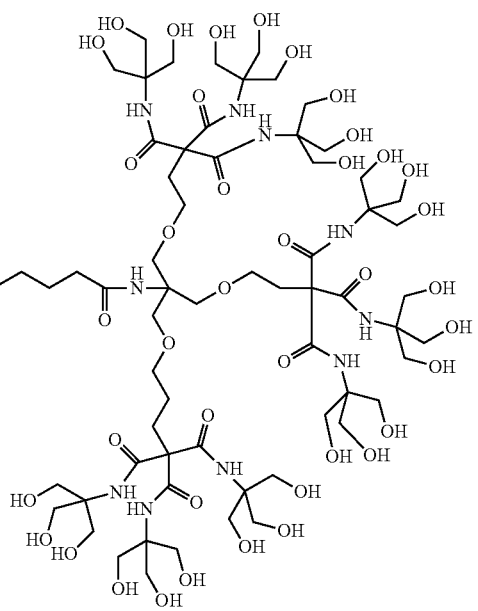
G.R. Newkome *J. Org. Chem.* 1985, 50, 2003

-continued
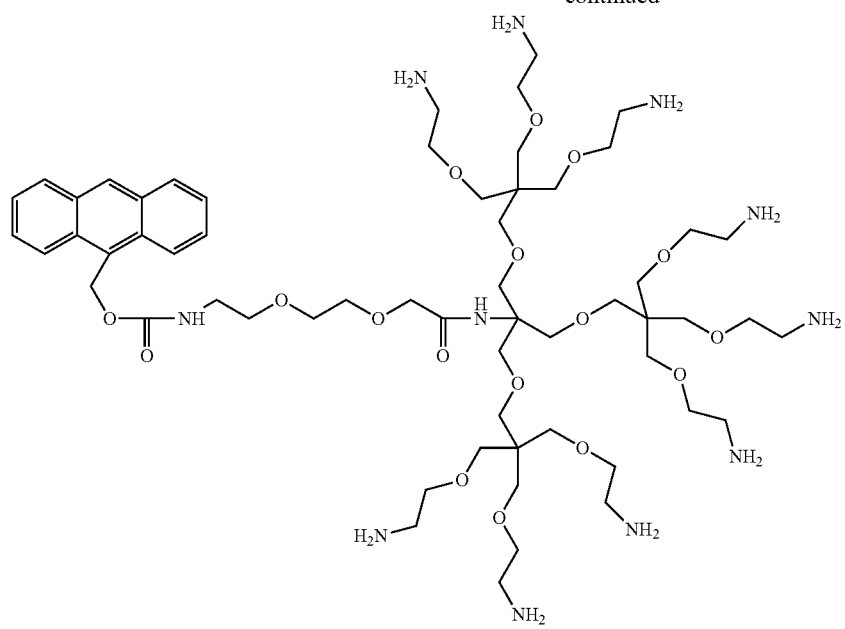
J.-J. Lee *Macromolecules* 1994, 27, 4632
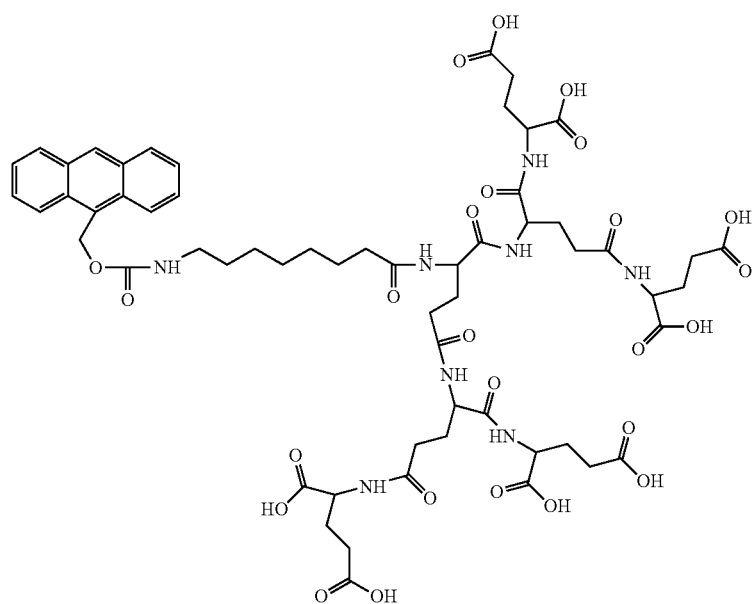
L.J. Twyman *Tetrahedron Lett.* 1994, 35, 4423

-continued
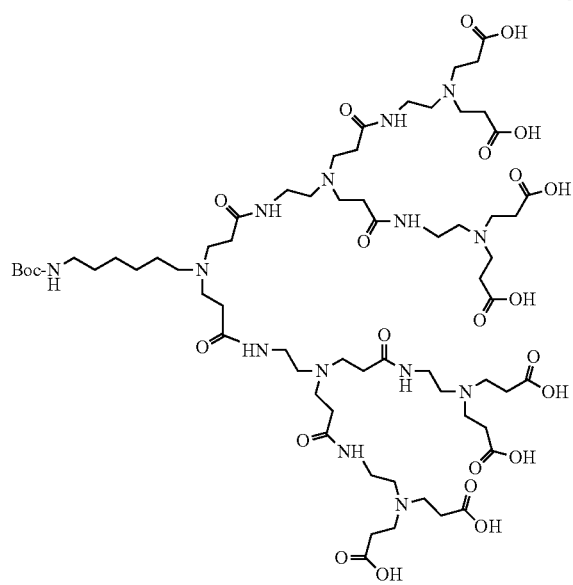
D.A. Tomalia *Polym. J.* 1985, 17, 117
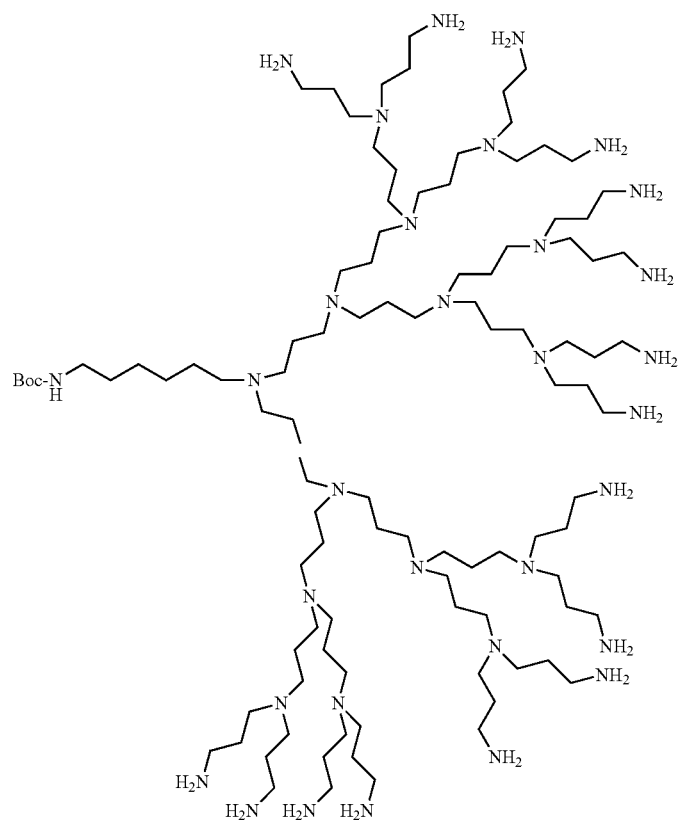
E. Buhleier. *Synthesis* 1978, 155

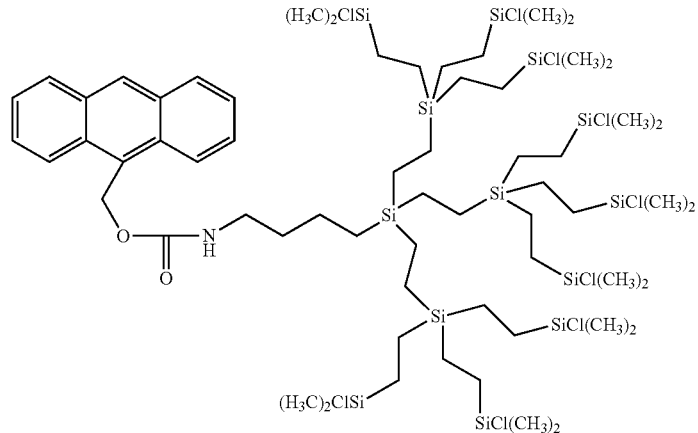
A. W. van der Made *J. Chem. Soc., Chem. Commun.* 1992, 1400
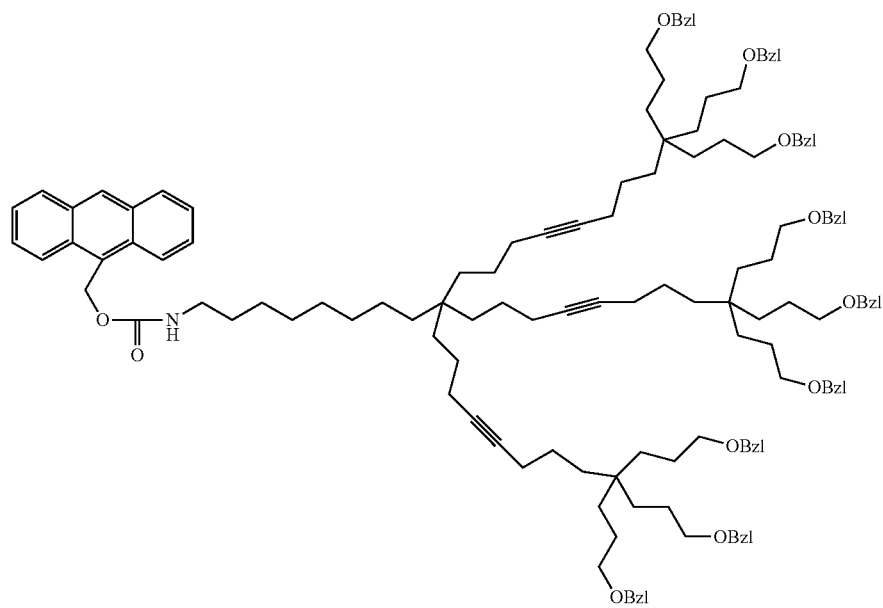
G. R. Newkome *Angew. Chem. Int. Ed. Engl.* 1991, 30, 1176

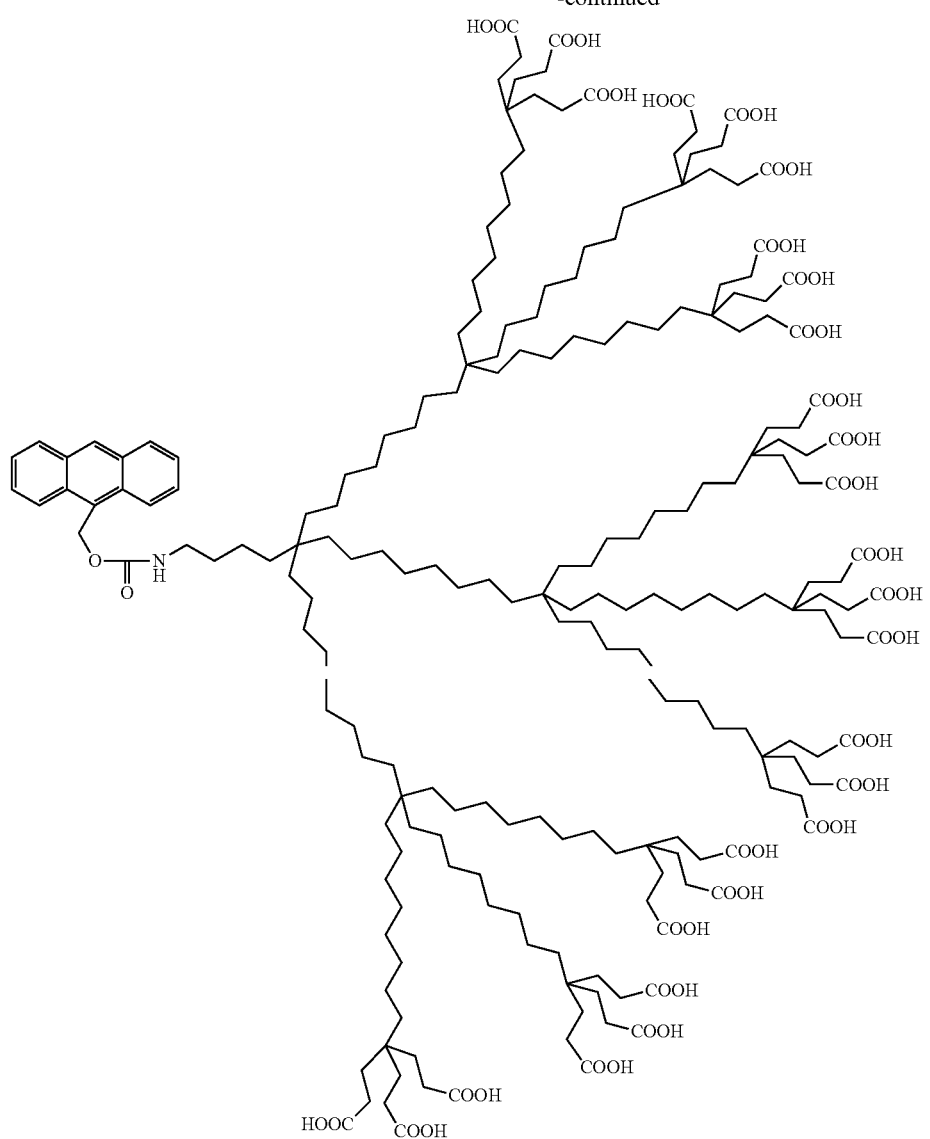
G.R. Newkome Angew. Chem. Int. Ed. Engl. 1991, 30, 1176
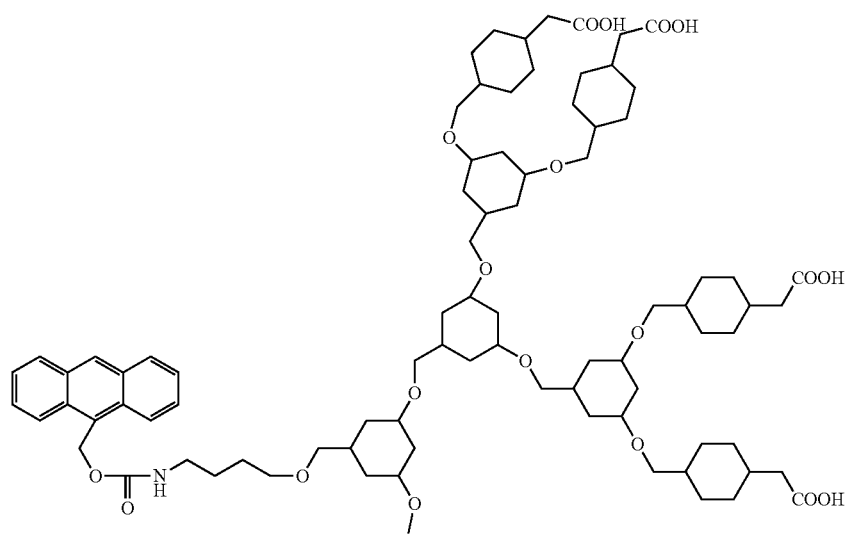

-continued
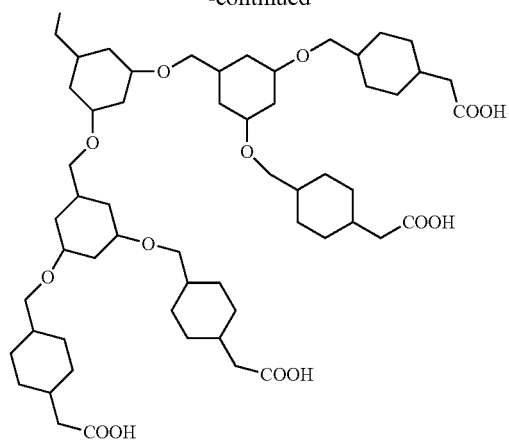
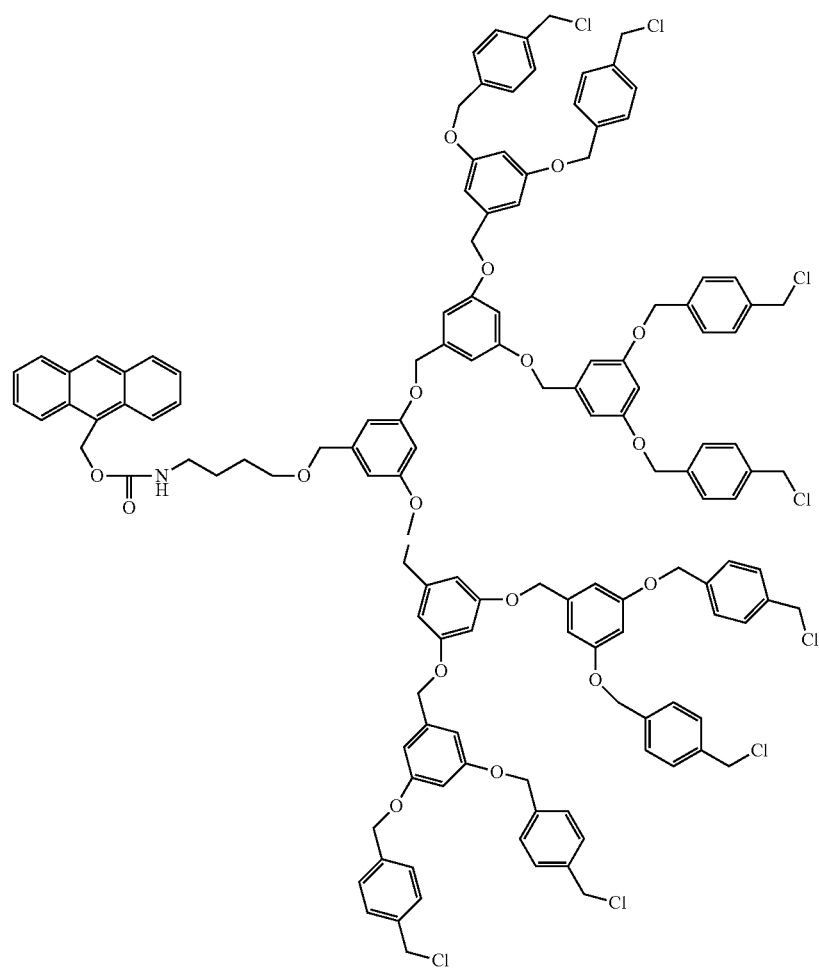
K. L. Wooley *J. Chem. Soc., Perkin Trans. 1* 1991, 1059

Example 3.1
Preparation Methods
1. A-[3]-OEt (3)
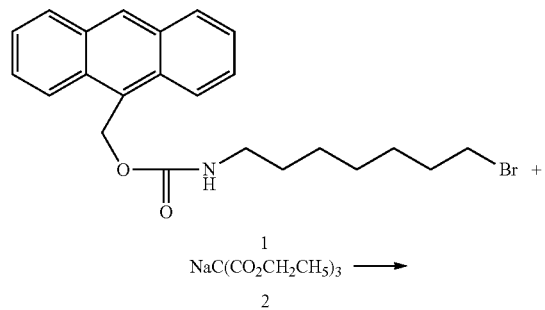
Compound 1 reacted with NaC(CO₂Et)₃ 2 in C₆H₆/DMF at 80° C.
2. A-[3]-OMe (5)
A-[3]-OEt 3 was reduced with LiAlH₄ or LiBH₄ in ether, reacted with chloroacetic acid in the presence of t-BuOK/t-BUOH, and esterified with MeOH.
3. A-[3]-OTs (7)

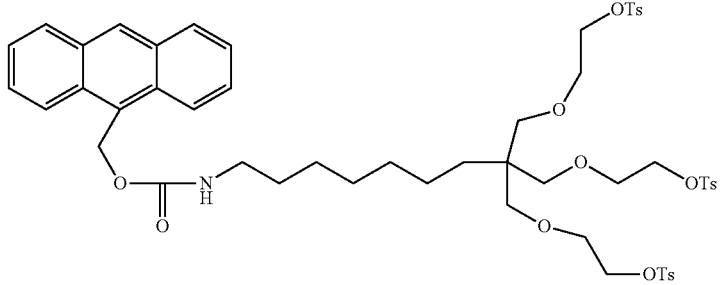
7
Reduction of A-[3]-OMe 5 with LiAlH₄ in ether yields triol compound 6, which is tosylated to compound 7.
4. A-[9]-OEt (8)
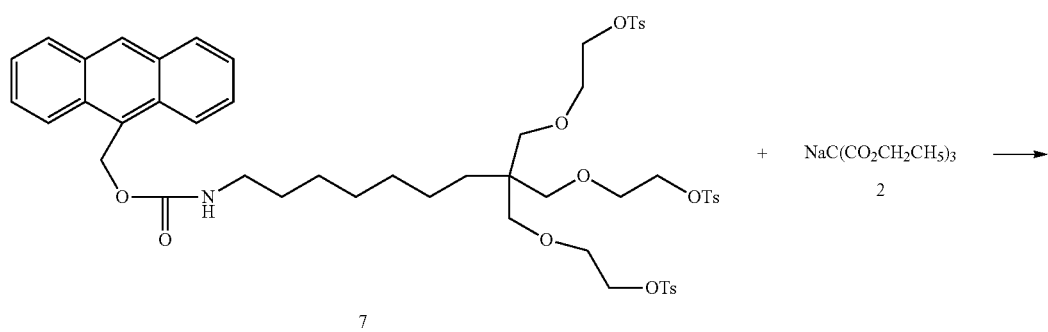
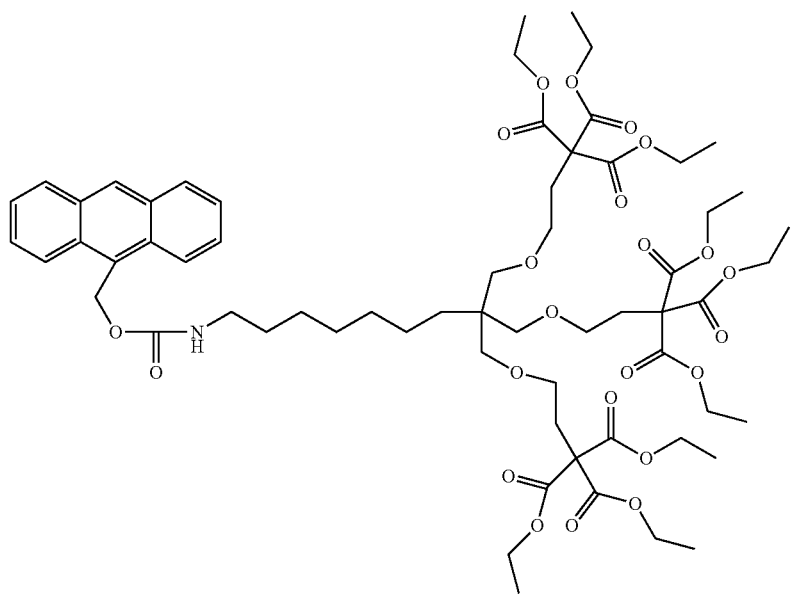
8

A-[3]-OTs 7 was treated with NaC(CO$_2$Et)$_3$ in C$_6$H$_6$-DMF to afford the desired nonaester (compound 8)
5. A-[27]-OH (9)
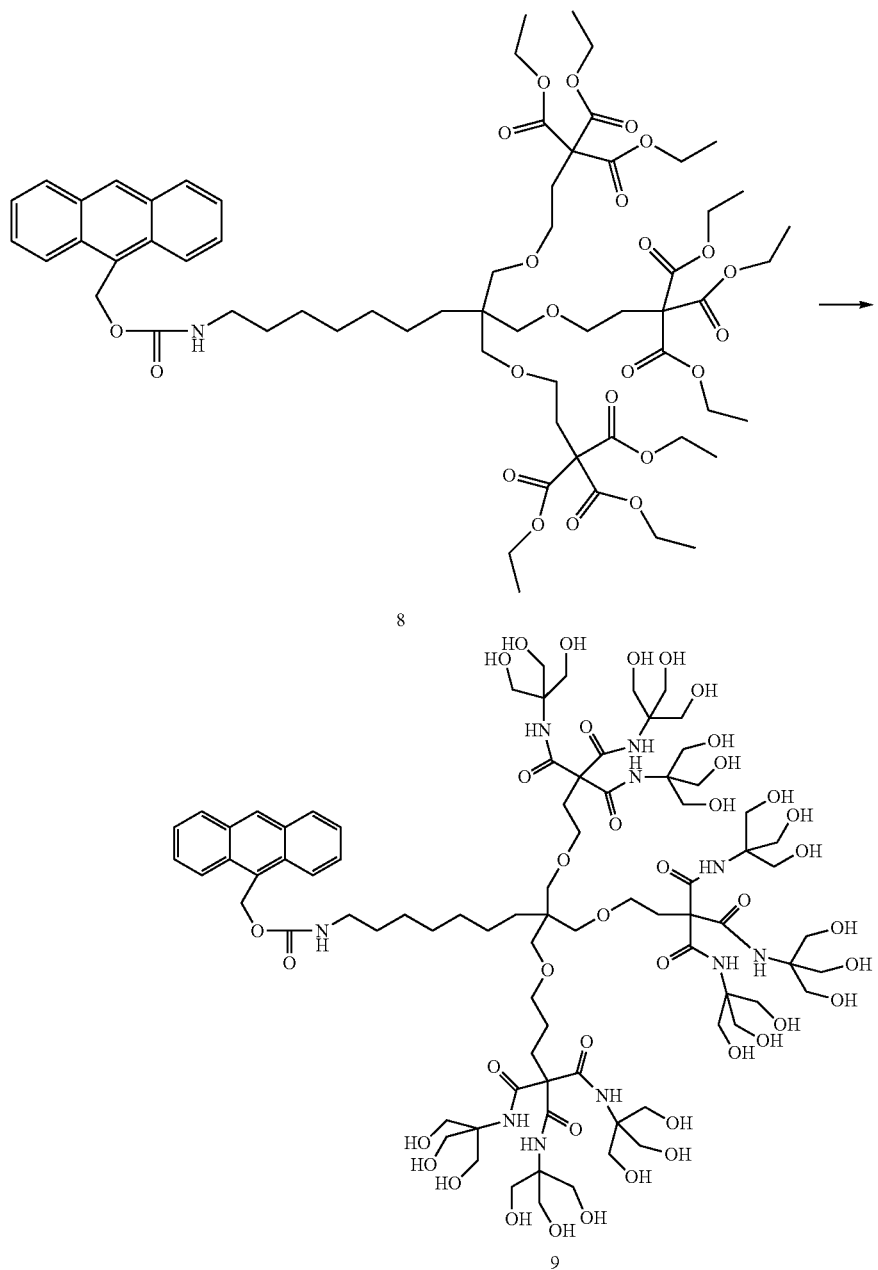
A-[9]-OEt 8 was treated with tris(hydroxymethyl)aminomethane and K$_2$CO$_3$ in DMSO at 70° C.
Example 3.2
1. Boc-[2]-OMe (3)

-continued

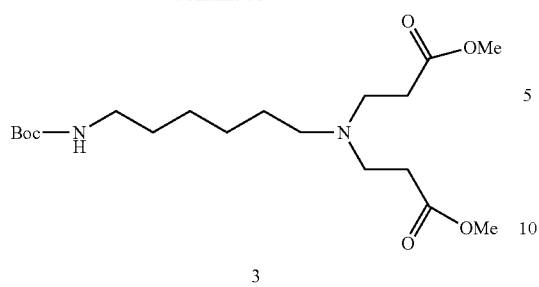

3

Compound 1 was reacted with methyl acrylate 2 in methanol solvent at temperature below 50° C. Excess reagents and solvent were removed under high vacuum at temperature below 55° C.

2. Boc-[4]-NH$_2$ (5)

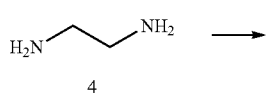

3

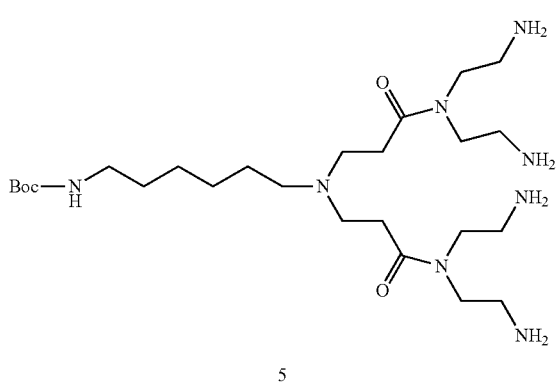

5 below 50° C. Excess reagents and solvent were removed under high vacuum at temperature below 55° C.

3. Boc-[8]-OMe (6)

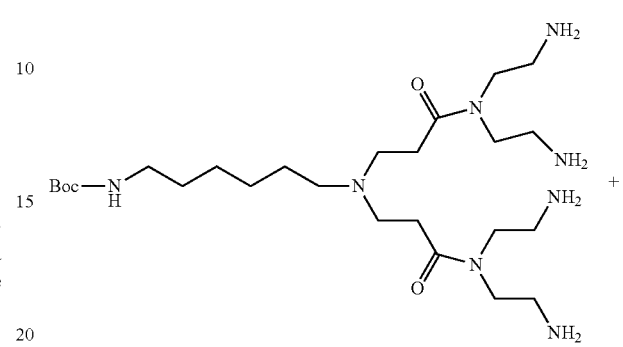

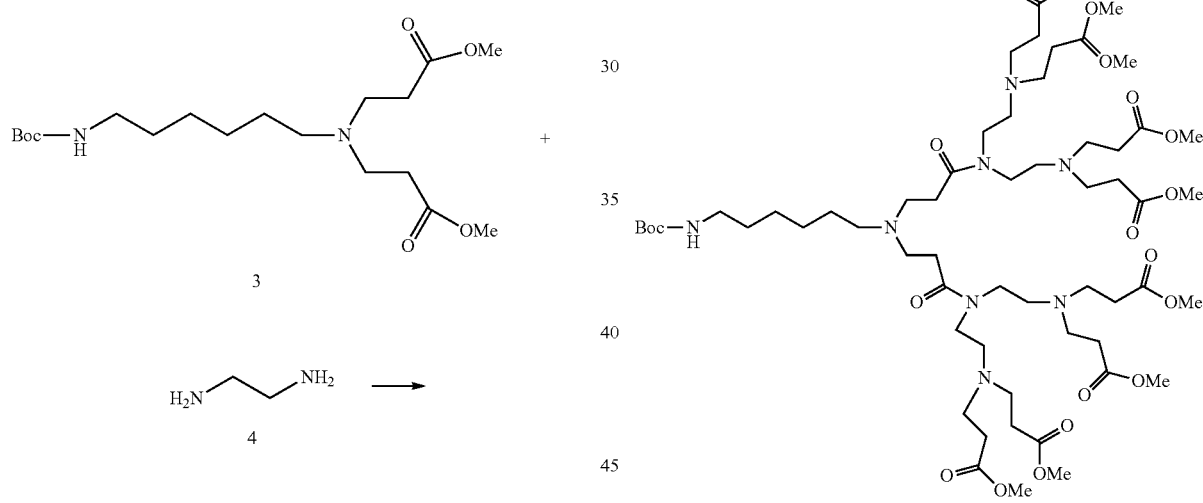

6

Boc-[4]-NH$_2$ 5 was reacted with methyl acrylate 2 in methanol solvent at temperature below 50° C. Excess reagents and solvent were removed under high vacuum at temperature below 55° C.

Example 3.3

1. Boc-[2]-OH (3)

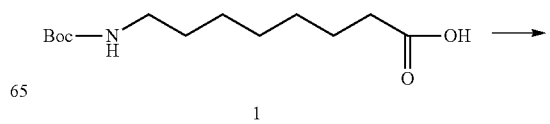

1

Boc-[2]-OMe 3 was reacted with large excesses of ethylenediamine (EDA) 4 in methanol solvent at temperature

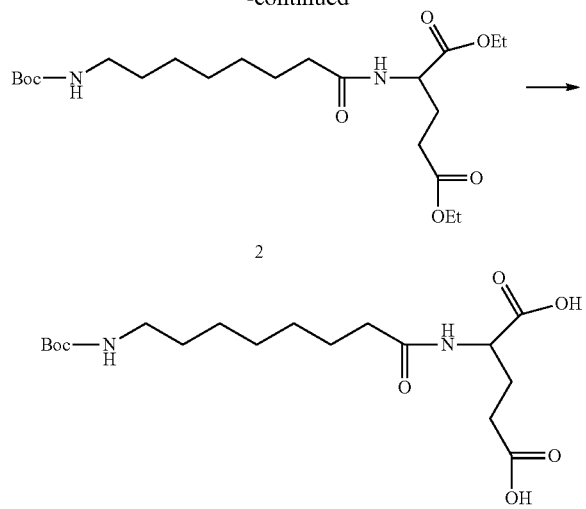

2

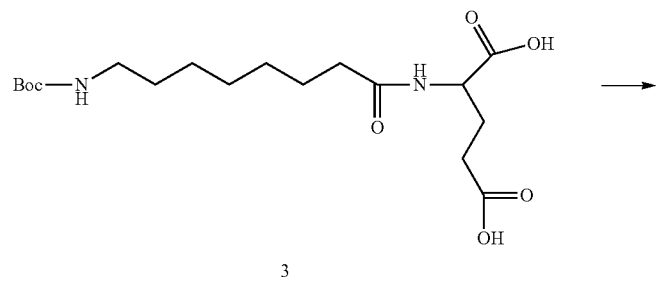

3

Compound 1, 1-[3-(dimethylamino)propyl]-3-ethylcarbodiimide hydrochloride (EDC), and 1-hydroxybenzotriazole hydrate (HOBT) were dissolved in acetonitrile and stirred at room temperature. L-glutamic acid-diethyl ester (H$_2$NCH(CO$_2$Et)CH$_2$CH$_2$CO$_2$Et) dissolved in acetonitrile was added with stirring, After stirring at room temperature for 12 h, the acetonitrile was evaporated. The crude product was dissolved in EA and washed with 1.0 N HCl and saturated sodium bicarbonate solution. After being dried with anhydrous MgSO$_4$, filtered, and evaporated, the crude product was loaded in a column packed with silica gel. Purification by column chromatography (eluent:ethyl acetate:haxane) resulted in a viscous yellow liquid.

Compound 2 was hydrolyzed by NaOH solution. After being stirred at room temperature for 1 d, the organic liquid was evaporated. The aqueous solution was washed with EA, stirred in an ice bath and acidified with dilute HCl. After the product was extracted with EA, the organic solution was dried with anhydrous MgSO$_4$, filtered and evaporated.

2. Boc-[4]-OH (3)

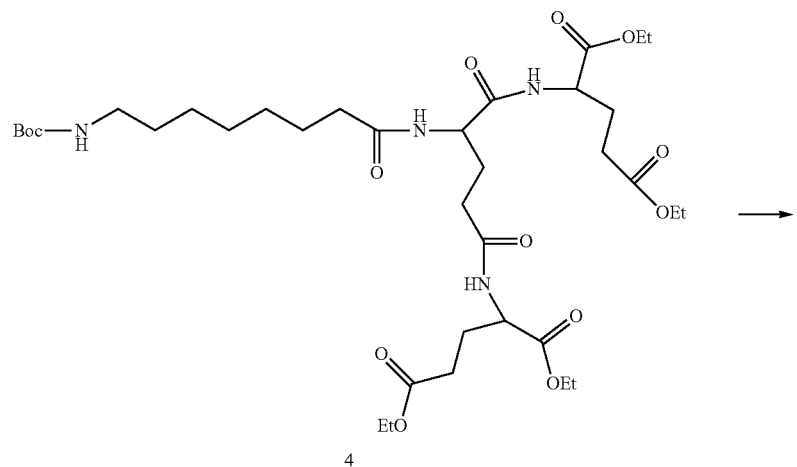

3

4

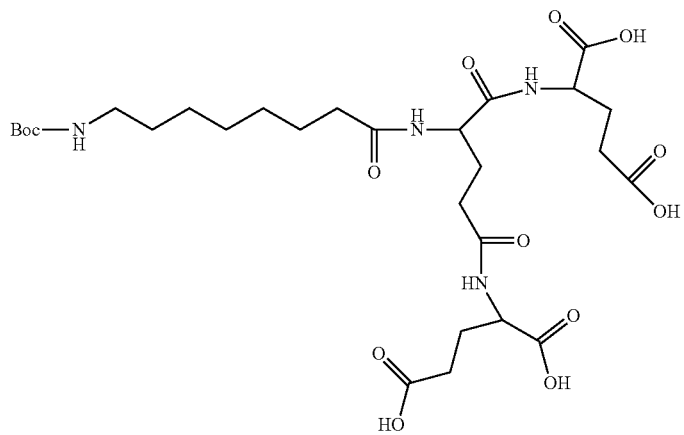

5

Compound 3, 1-[3-(dimethylamino)propyl]-3-ethylcarbodiimide hydrochloride (EDC), and 1-hydroxybenzotriazole hydrate (HOBT) were dissolved in acetonitrile and stirred at room temperature. L-glutamic acid-diethyl ester ($H_2NCH(CO_2Et)CH_2CH_2CO_2Et$) dissolved in acetonitrile was added with stirring, After stirring at room temperature for 12 h, the acetonitrile was evaporated. The crude product was dissolved in EA and washed with 1.0 N HCl and saturated sodium bicarbonate solution. After being dried with anhydrous $MgSO_4$, filtered, and evaporated, the crude product was loaded in a column packed with silica gel. Purification by column chromatography (eluent:ethyl acetate:haxane) resulted in a viscous yellow liquid.

Compound 4 was hydrolyzed by NaOH solution. After being stirred at room temperature for 1 d, the organic liquid was evaporated. The aqueous solution was washed with EA, stirred in an ice bath and acidified with dilute HCl. After the product was extracted with EA, the organic solution was dried with anhydrous $MgSO_4$, filtered and evaporated.

3. Boc-[8]-OH (3)

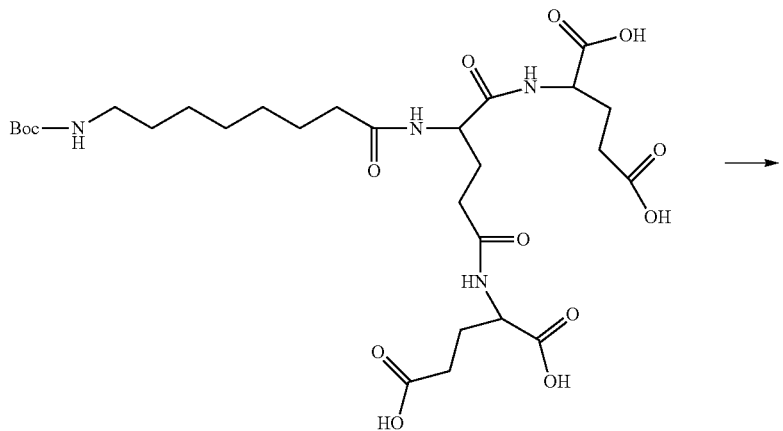

5

-continued

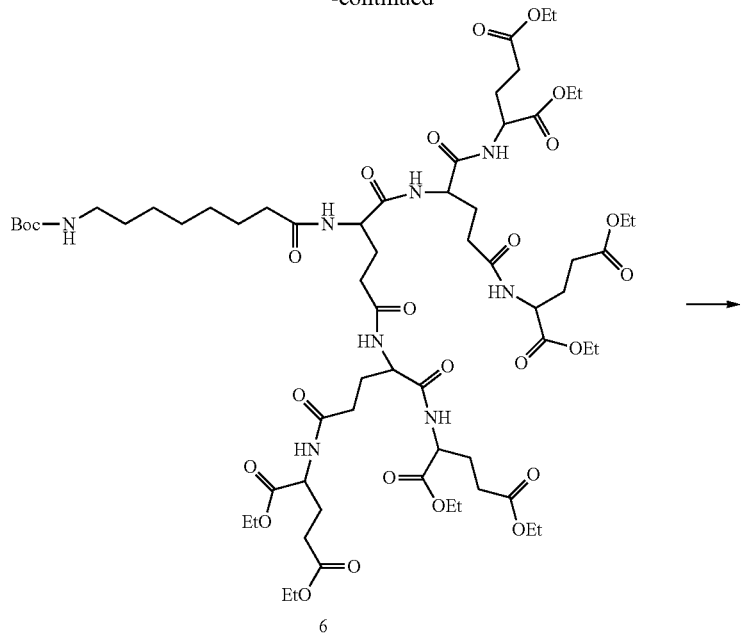
6

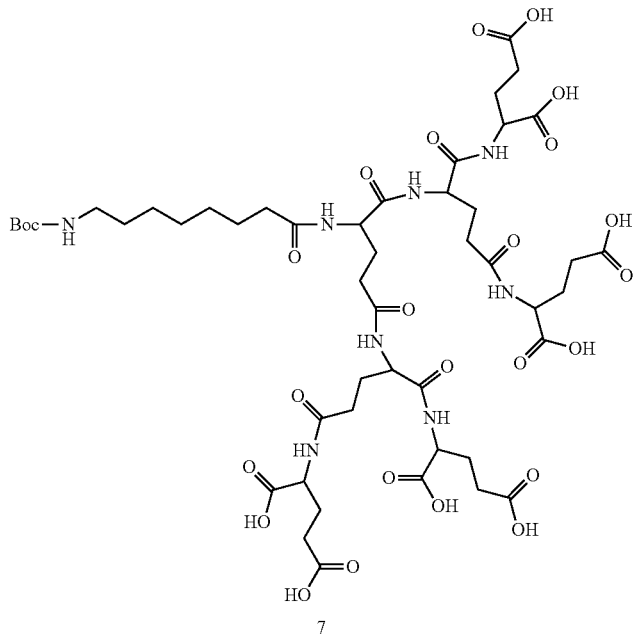
7

Compound 5, 1-[3-(dimethylamino)propyl]-3-ethylcarbodiimide hydrochloride (EDC), and 1-hydroxybenzotriazole hydrate (HOBT) were dissolved in acetonitrile and stirred at room temperature. L-glutamic acid-diethyl ester (H$_2$NCH(CO$_2$Et)CH$_2$CH$_2$CO$_2$Et) dissolved in acetonitrile was added with stirring, After stirring at room temperature for 12 h, the acetonitrile was evaporated. The crude product was dissolved in EA and washed with 1.0 N HCl and saturated sodium bicarbonate solution. After being dried with anhydrous MgSO$_4$, filtered, and evaporated, the crude product was loaded in a column packed with silica gel. Purification by column chromatography (eluent:ethyl acetate:haxane) resulted in a viscous yellow liquid.

Compound 6 was hydrolyzed by NaOH solution. After being stirred at room temperature for 1 d, the organic liquid was evaporated. The aqueous solution was washed with EA, stirred in an ice bath and acidified with dilute HCl. After the product was extracted with EA, the organic solution was dried with anhydrous MgSO$_4$, filtered and evaporated.

Example 3.4

1. Boc-[2]-CN (3)

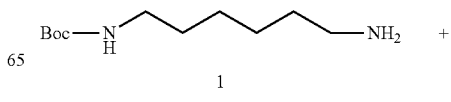
1

-continued

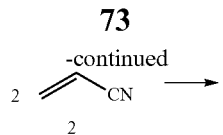

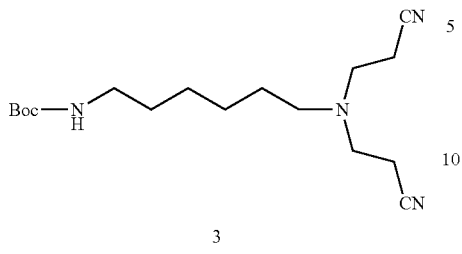

3

Compound 1 was dissolved at room temp. in acrylonitrile. Glacial acetic acid was added and the solution is heated under reflux for 24 h. Excess acrylonitrile was distilled off under vacuum, the residue was extracted with chloroform, and added to concentrated ammonia solution. The organic phase was separated, washed with water, and dried with sodium sulfate.

2. Boc-[2]-NH$_2$ (4)

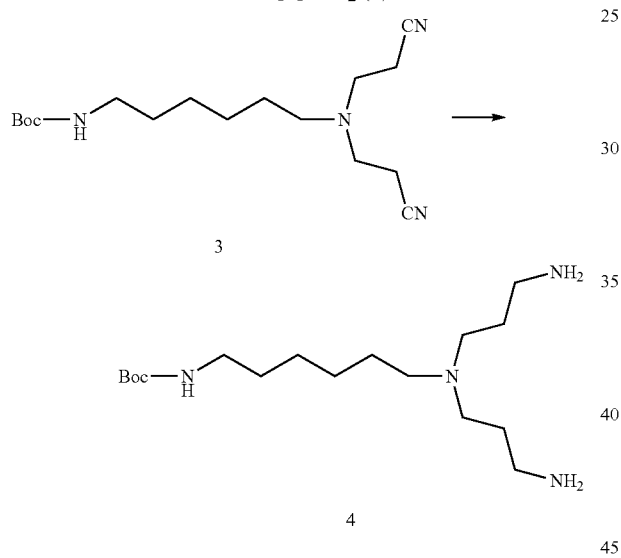

Boc-[2]-CN 3 was dissolved in methanol and cobalt(II) chloride hexahydrate was added. Sodium borohydride was added in portions. The resultant mixture was stirred for 2 h at room temp. and then cautiously acidified with concentrated hydrochloric acid. The solvent was removed under vacuum and concentrated. The organic phase was separated, washed with water, and dried with sodium sulfate.

3. Boc-[4]-CN (5)

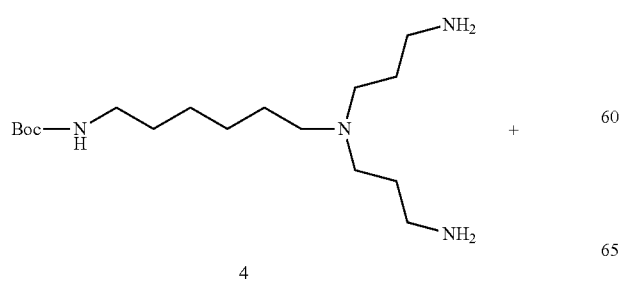

-continued

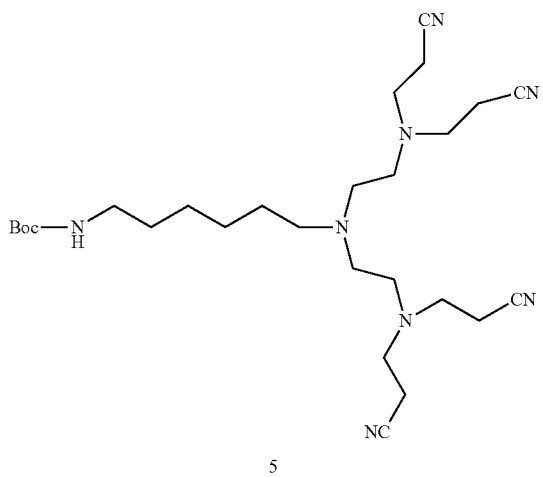

5

Boc-[2]-NH$_2$ 4 was dissolved at room temp. in acrylonitrile. Glacial acetic acid was added and the solution is heated under reflux for 24 h. Excess acrylonitrile was distilled off under vacuum, the residue was extracted with chloroform, and added to concentrated ammonia solution. The organic phase was separated, washed with water, and dried with sodium sulfate.

4. Boc-[4]-NH$_2$ (6)

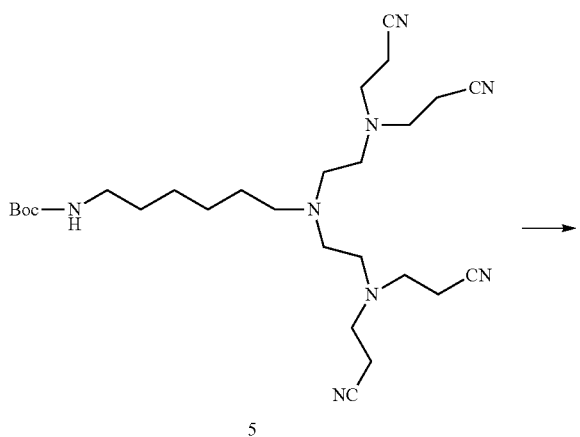

5

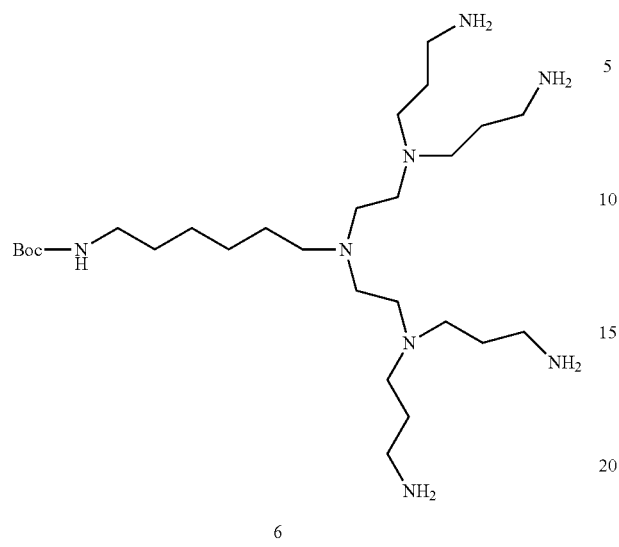

6

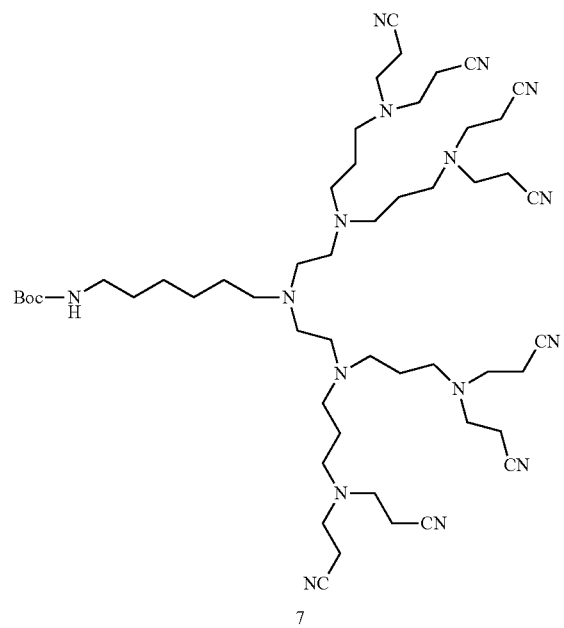

7

Boc-[4]-CN 5 was dissolved in methanol and cobalt(II) chloride hexahydrate was added. Sodium borohydride was added in portions. The resultant mixture was stirred for 2 h at room temp. and then cautiously acidified with concentrated hydrochloric acid. The solvent was removed under vacuum and concentrated. The organic phase was separated, washed with water, and dried with sodium sulfate.

Boc-[4]-NH$_2$ 6 was dissolved at room temp. in acrylonitrile. Glacial acetic acid was added and the solution is heated under reflux for 24 h. Excess acrylonitrile was distilled off under vacuum, the residue was extracted with chloroform, and added to concentrated ammonia solution. The organic phase was separated, washed with water, and dried with sodium sulfate.

5. Boc-[8]-CN (7)

6. Boc-[8]-NH$_2$ (8)

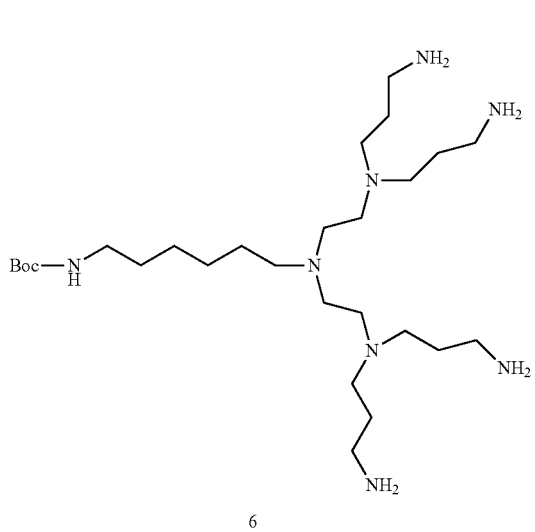

6

+

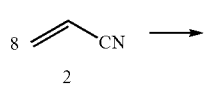

8           2

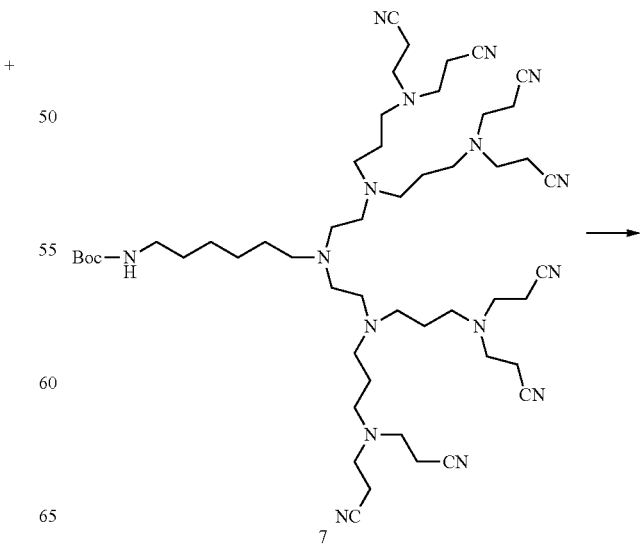

7

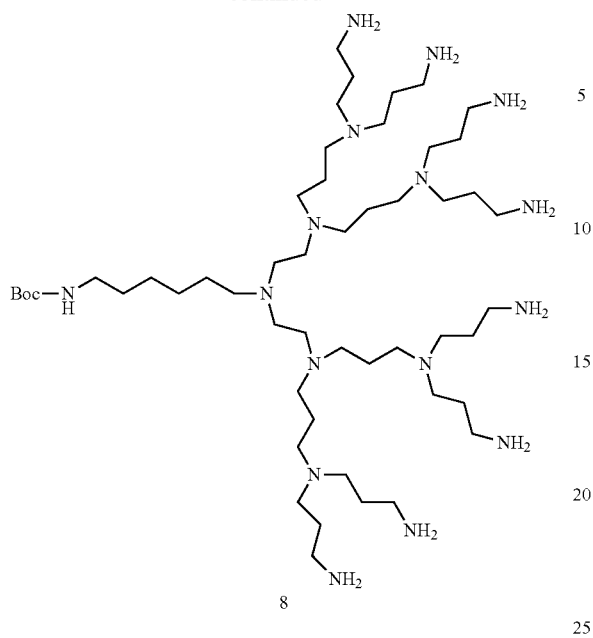

Boc-[8]-CN 7 was dissolved in methanol and cobalt(II) chloride hexahydrate was added. Sodium borohydride was added in portions. The resultant mixture was stirred for 2 h at room temp. and then cautiously acidified with concentrated hydrochloric acid. The solvent was removed under vacuum and concentrated. The organic phase was separated, washed with water, and dried with sodium sulfate.

7. Boc-[16]-CN (9)

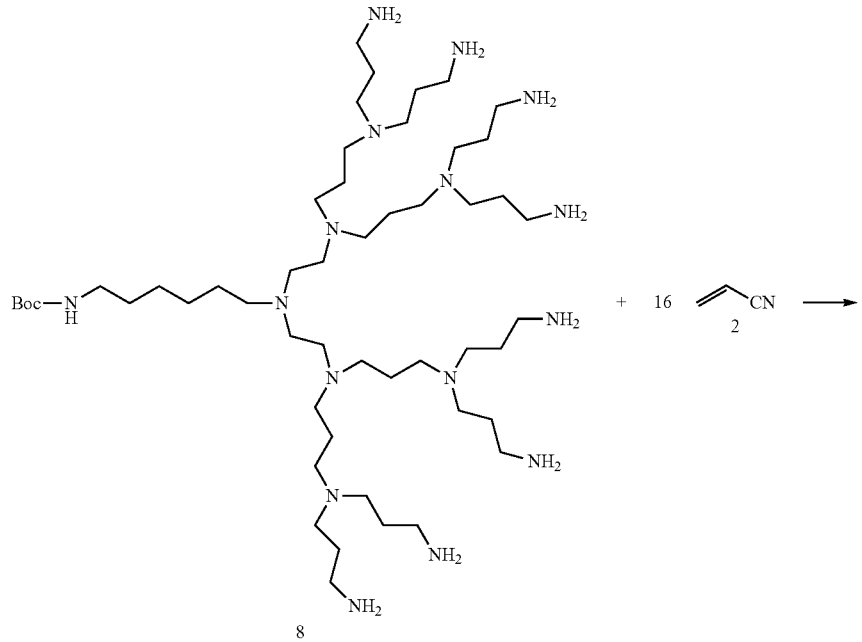

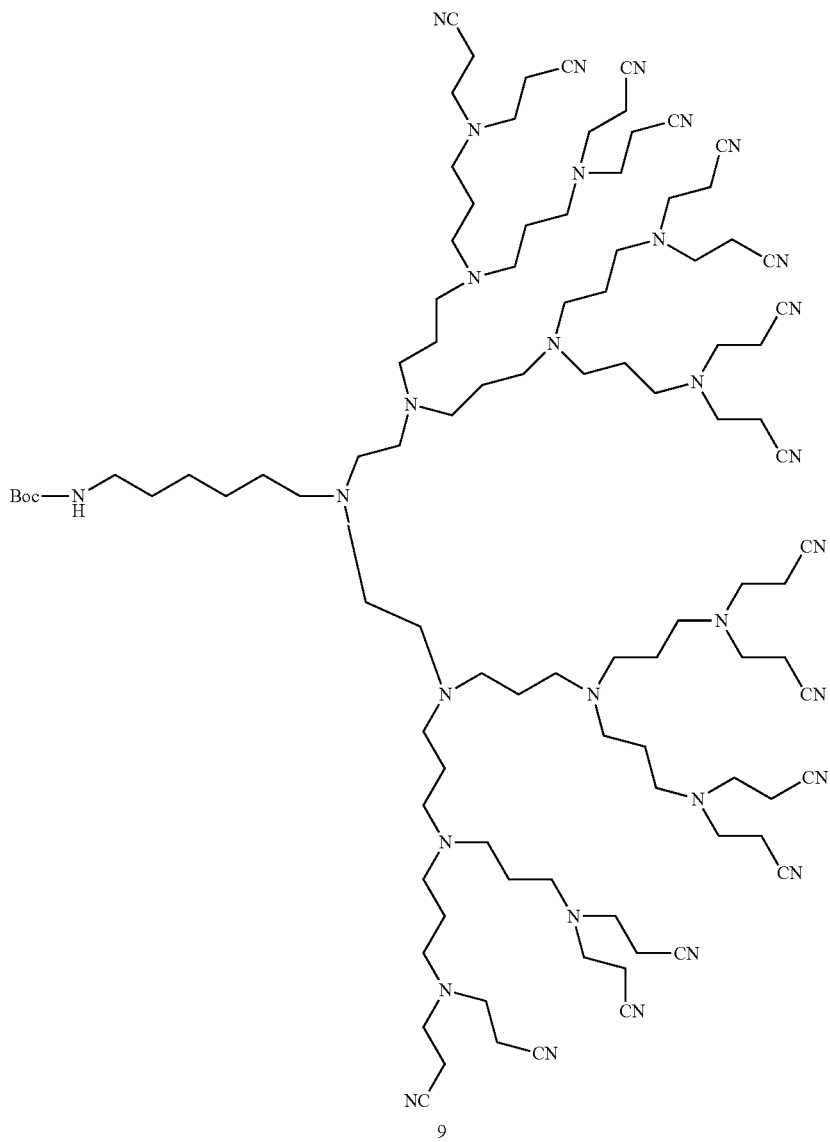
9
Boc-[8]-NH$_2$ 8 was dissolved at room temp. in acrylonitrile. Glacial acetic acid was added and the solution is heated under reflux for 24 h. Excess acrylonitrile was distilled off under vacuum, the residue was extracted with chloroform, and added to concentrated ammonia solution. The organic phase was separated, washed with water, and dried with sodium sulfate.

7. Boc-[16]-NH$_2$ (10)
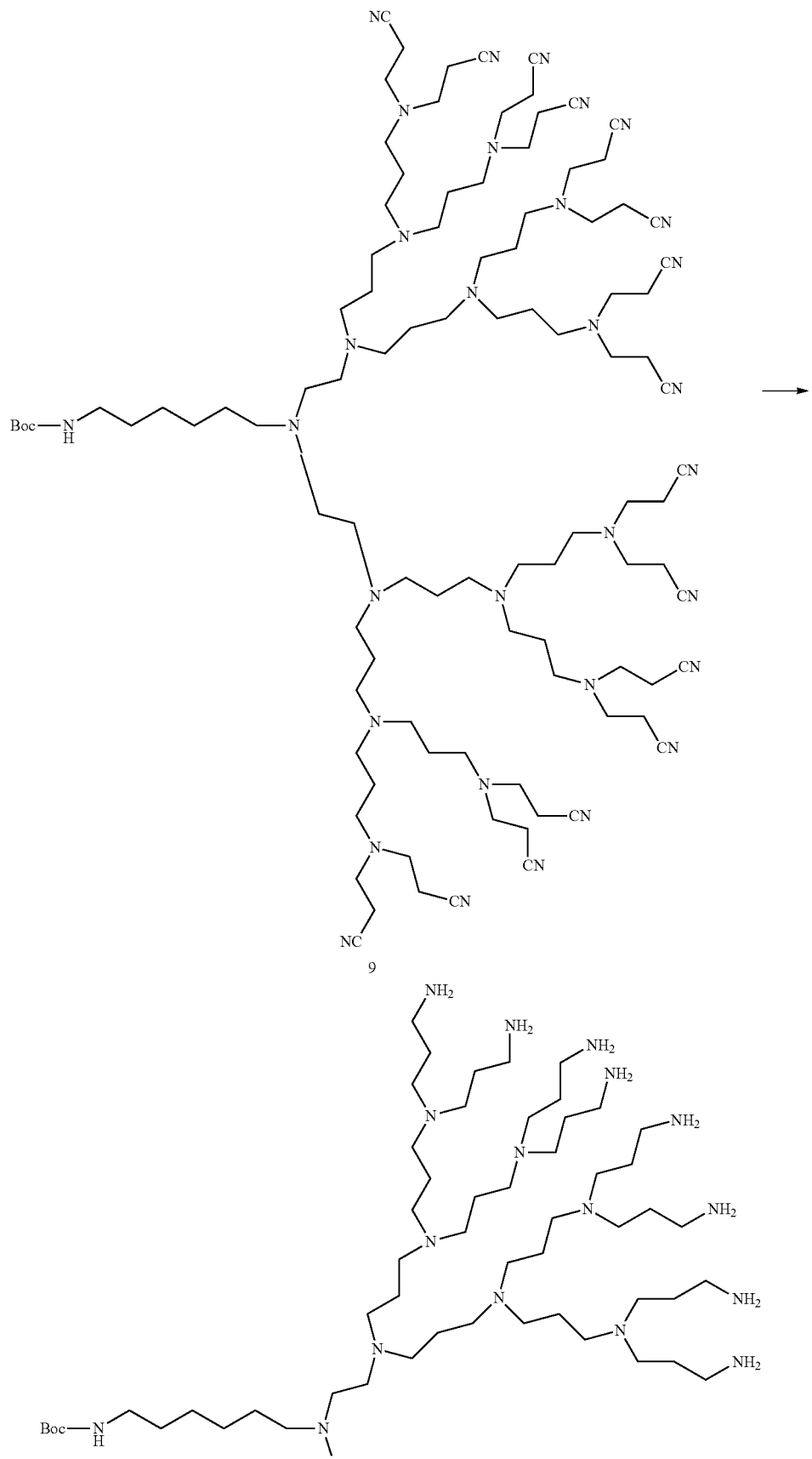

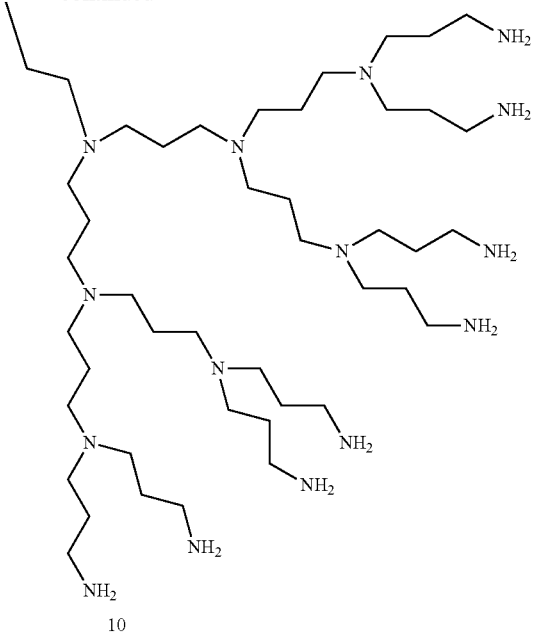

10

Boc-[16]-CN 9 was dissolved in methanol and cobalt(II) chloride hexahydrate was added. Sodium borohydride was added in portions. The resultant mixture was stirred for 2 h at room temp. and then cautiously acidified with concentrated hydrochloric acid. The solvent was removed under vacuum and concentrated. The organic phase was separated, washed with water, and dried with sodium sulfate.

Example 3.5

1. A-[3]-Alkene (3)

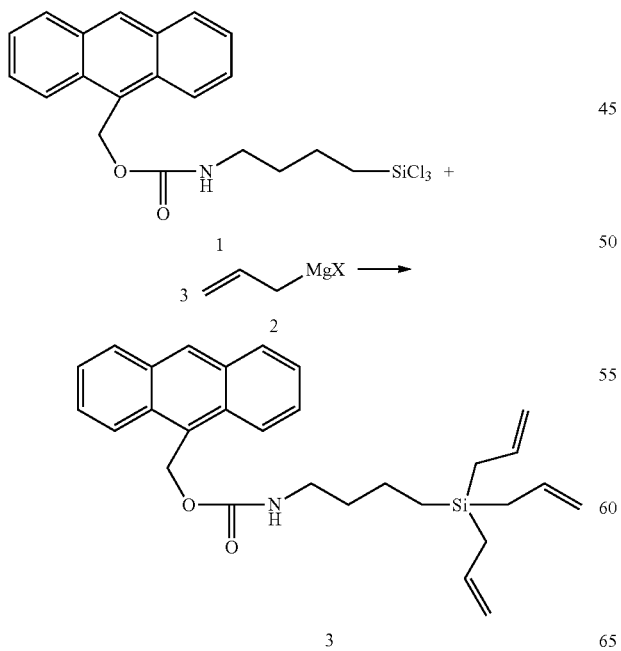

A-[1]-SiCl$_3$ 1 was refluxed with 10% excess of allylmagnesium bromide in diethyl ether for 4 h, and cooled to 0° C. and hydrolyzed with 10% aqueous NH$_4$Cl. The organic layer was washed with water, dried MgSO$_4$ and concentrated.

2. A-[3]-SiCl$_3$ (4)

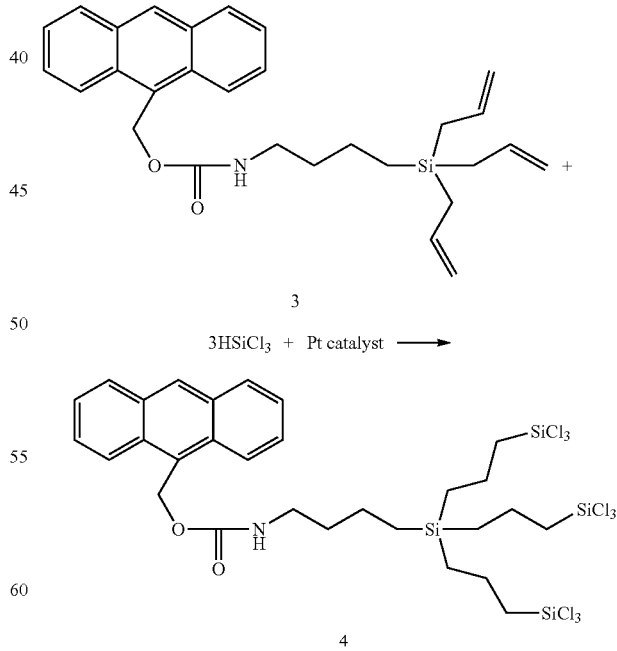

A mixture of A-[3]-Alkene 3, HSiCl$_3$, and a common platinum-based hydrosilylation catalyst, e.g. H2PtCl6 in propan-2-ol (Speier's catalyst) or platinum divinylsiloxane complecx (Karstedt's catalyst), was stirred for 24 h at room temp. When the reaction was completed, excess HSiCl₃ was removed under vacuum.

3. A-[9]-Alkene (5)

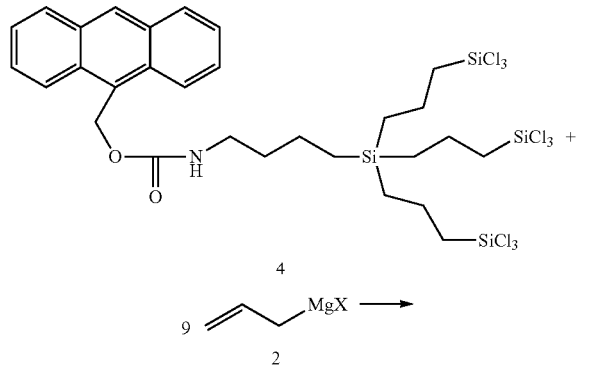
4

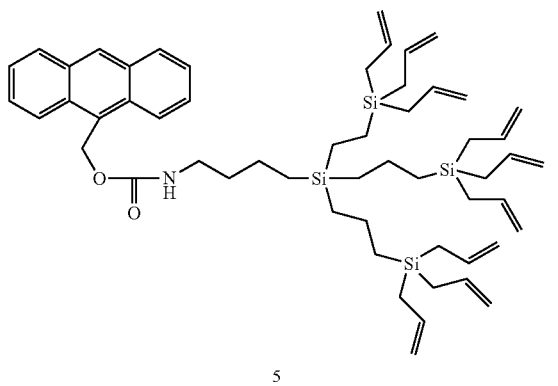
5

A-[3]-SiCl₃ 4 was refluxed with 10% excess of allylmagnesium bromide in diethyl ether for 4 h, and cooled to 0° C. and hydrolyzed with 10% aqueous NH₄Cl. The organic layer was washed with water, dried MgSO₄ and concentrated.

4. A-[9]-SiCl₃ (6)

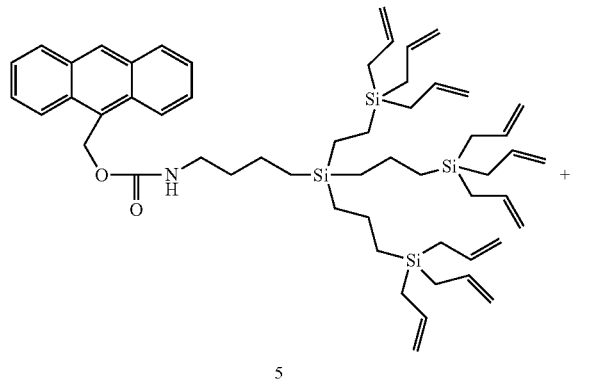
5

3HSiCl₃ + Pt catalyst ⟶

-continued

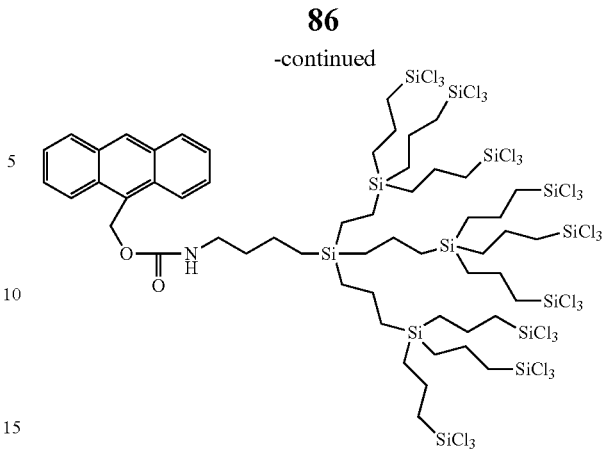
6

A mixture of A-[9]-Alkene 5, HSiCl₃, and a common platinum-based hydrosilylation catalyst, e.g. H2PtCl6 in propan-2-ol (Speier's catalyst) or platinum divinylsiloxane complecx (Karstedt's catalyst), was stirred for 24 h at room temp. When the reaction was completed, excess HSiCl₃ was removed under vacuum.

Example 3.6

1. [1]-acid-[3]-triol (3)

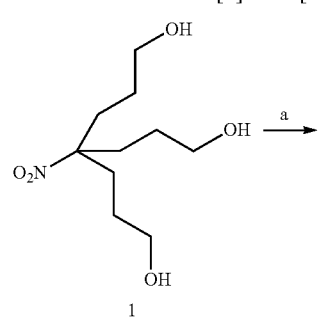

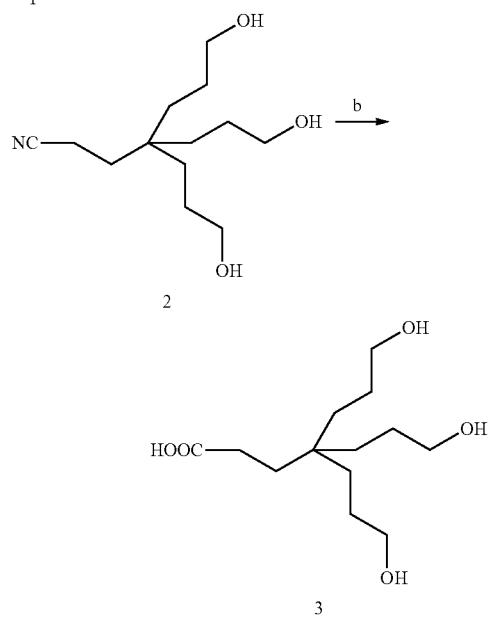

(a) The triol 1 was cyanoethylated affording the nitrile compound 2. Acrylonitrile, nBu₃SnH, and azobisisobutyronitrile was added in PhCH₃ including compound 1 at 110° C. (b) The nitirle compound 2 was hydrolyzed to give compound 3 with carboxylic acid cleanly in such condition as KOH, EtOH/H₂O, H₂O₂, Δ.

2. A-[3]-triol (5)
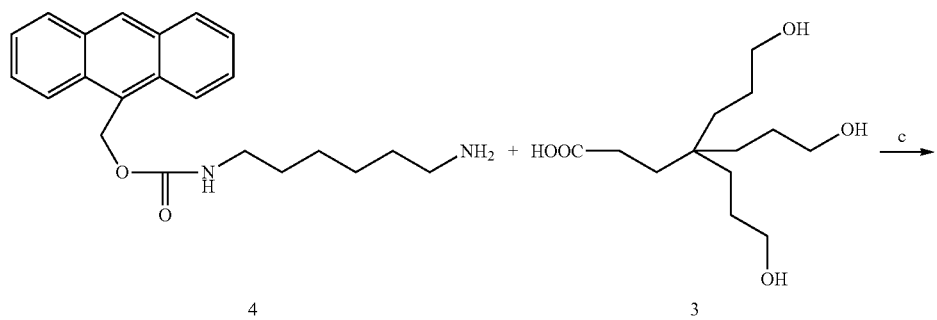
4         3
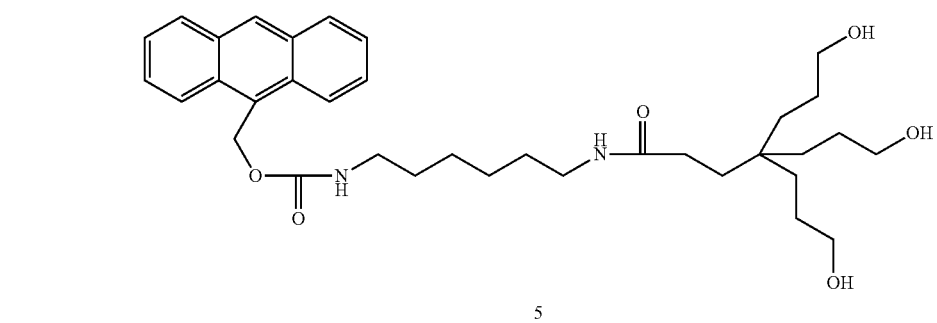
5
(c) [1]-acid-[3]-triol was linked with compound 4 through an amide coupling reaction using 1-[3-(dimethylamino)propyl]-3-ethylcarbodiimide hydrochloride (EDC) and 1-hydroxybenzotriazole hydrate (HOBT).
3. A-[3]-tribromide (6)
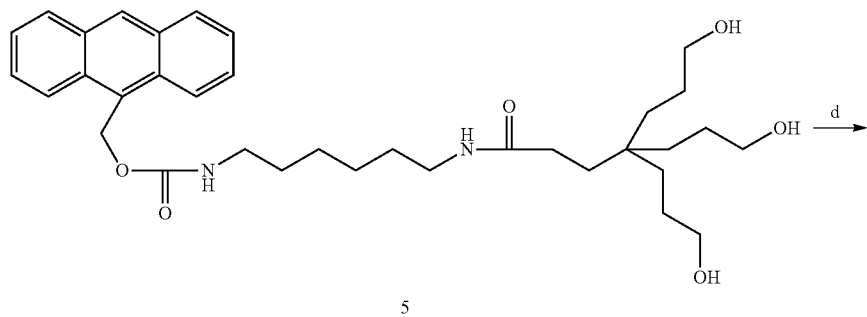
5
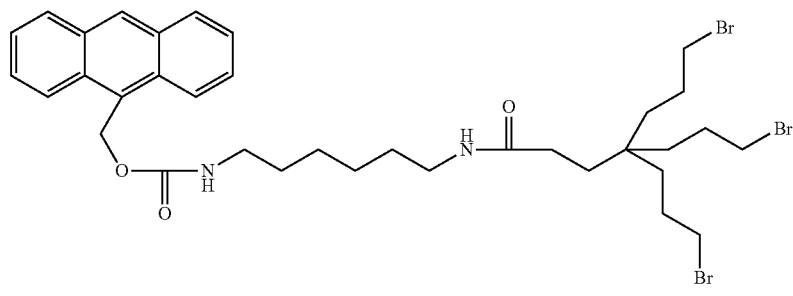
6

(d) The alcohol was used to synthesize tribromide by bromination with HBr/H$_2$SO$_4$ at 100° C.

4. [1]-CN-[3]-OBzl (8)

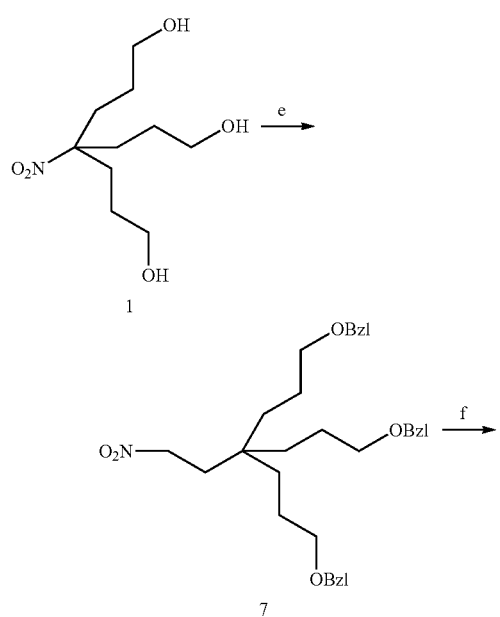

(e) The triol 1 was treated with benzyl chloride to give trisether using Me$_2$SO and KOH. (f) The trisether 8 was cyanoethylated affording the nitrile compound 9. Acrylonitrile, nBu$_3$SnH, and azobisisobutyronitrile was added in PhCH$_3$ including compound 8 at 110° C.

5. [1]-OH-[3]-OBzl (11)

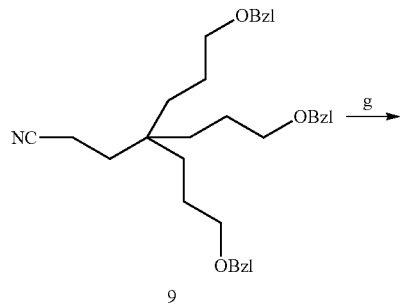

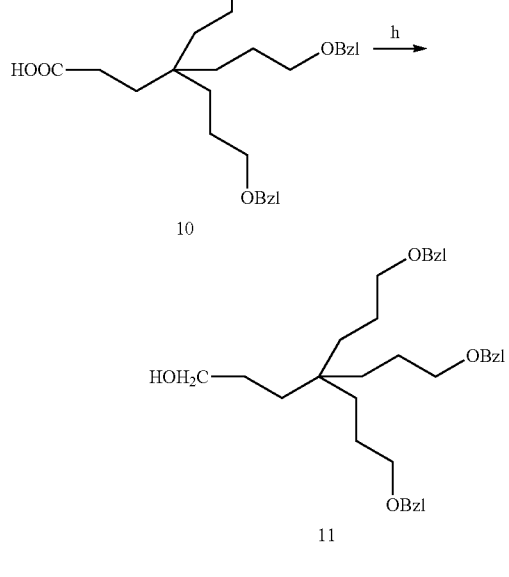

(g) The nitirle compound 9 was hydrolyzed to give compound 10 with carboxylic acid cleanly in such condition as KOH, EtOH/H$_2$O, H$_2$O$_2$, Δ. (h) The compound 10 with a carboxylic acid was proceeded with excess 1.0 M BH$_3$.THF solution to converse the acid into alcohol.

6. [1]-Alkyne-[3]-OBzl (13)

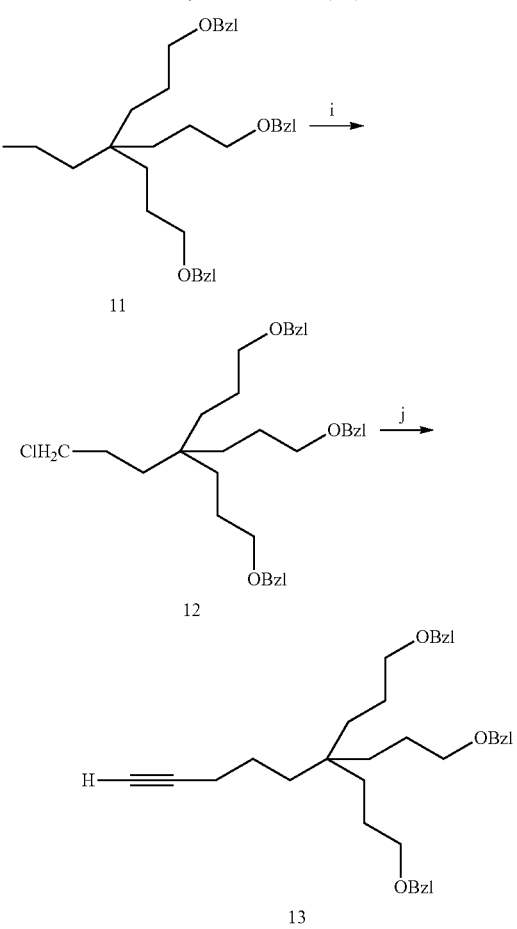

(i) The alcohol was transformed into chloride (CH$_2$Cl$_2$) with excess SOCl$_2$ and a catalytic amount of pyridine. (j) The chloride was reacted with lithium acetylide ethylenediamine complex in dimethylsulphoxide at 40° C.

7. A-[3]-Alkyne-[9]-OBzl (14)

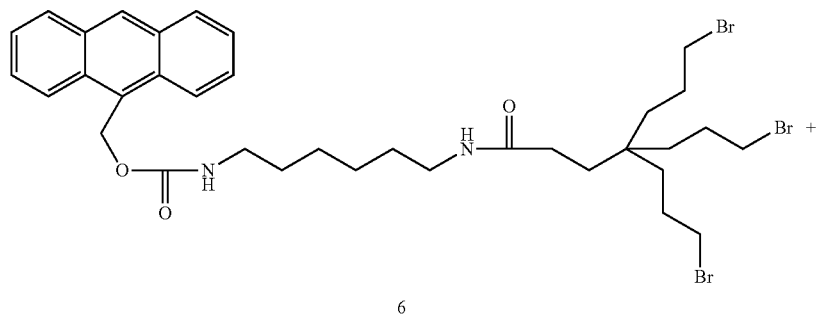

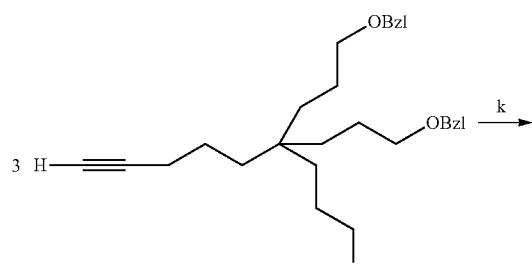

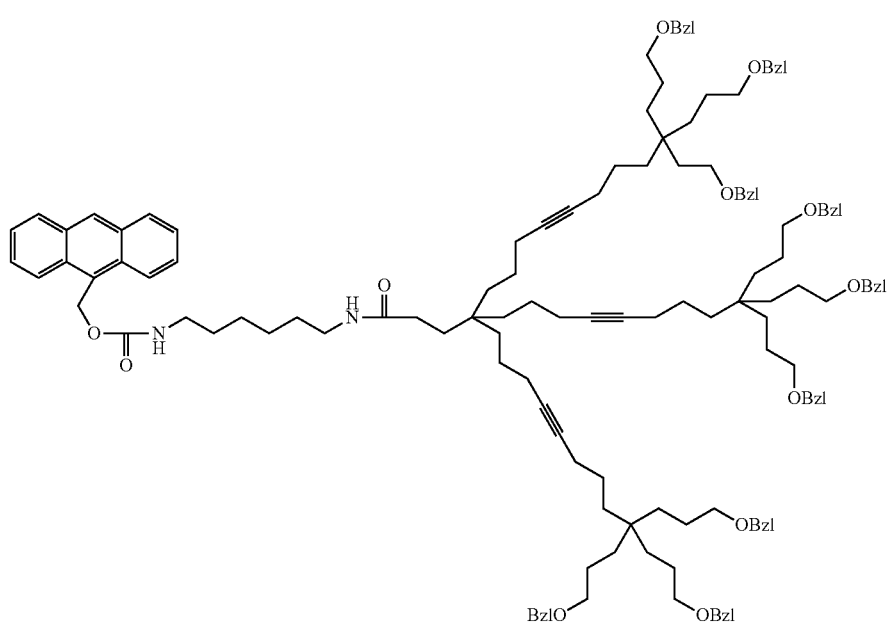

(k) The A-[3]-OBzl 6 was alkylated with 4 equivalents of terminal alkyne building block 13, hexamethylphosphoric rtriamide (HMPA), lithium diisopropylamide (LDA), and tetramethylethylenediamine (TMED) at 0-40° C. for 1.5 h.

Example 3.7
1. A-[9]-OH (15)
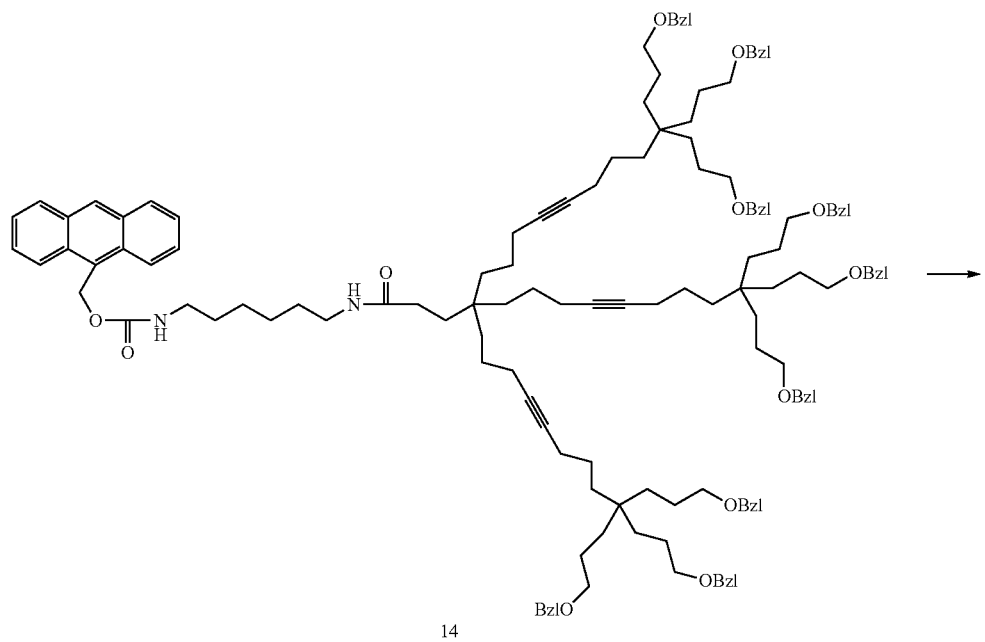
14
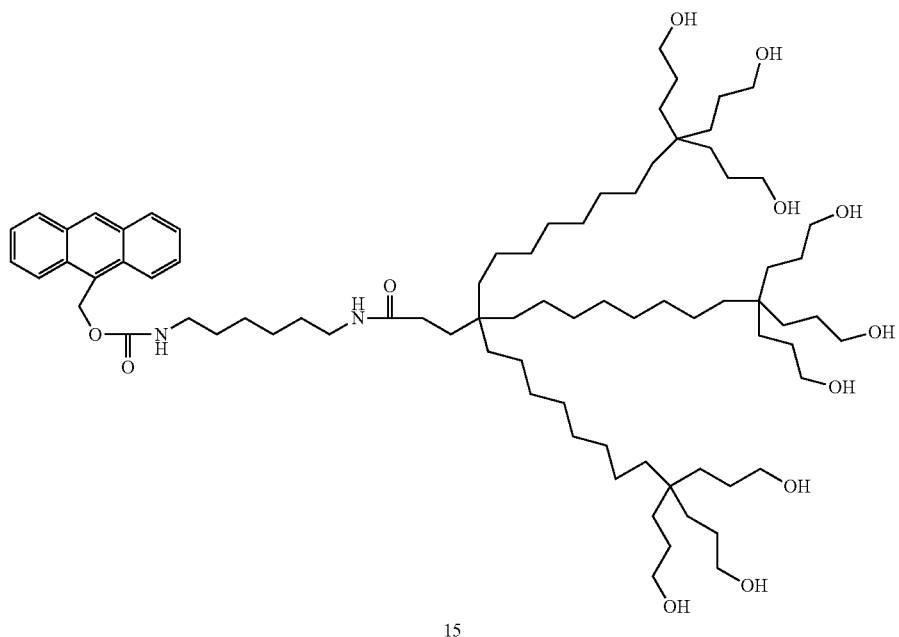
15
A-[3]-Alkyne-[9]-OBzl 14 was reduced and deprotected with Pd—C/H to produce A-[9]-OH 15 in EtOH and THF solution including 10% Pd—C/H at 60° C. for 4 d.
2. A-[27]-COOH (17)

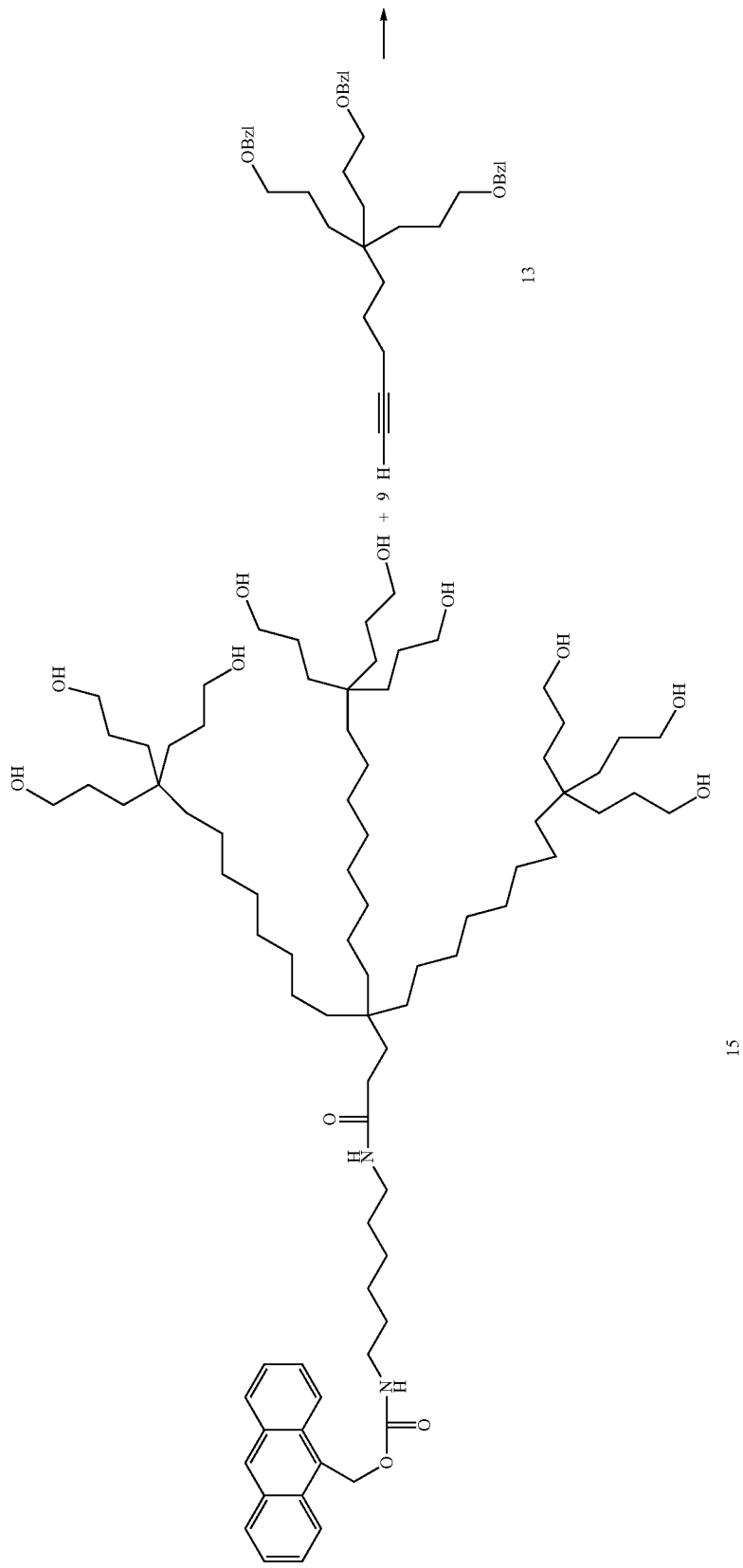

-continued
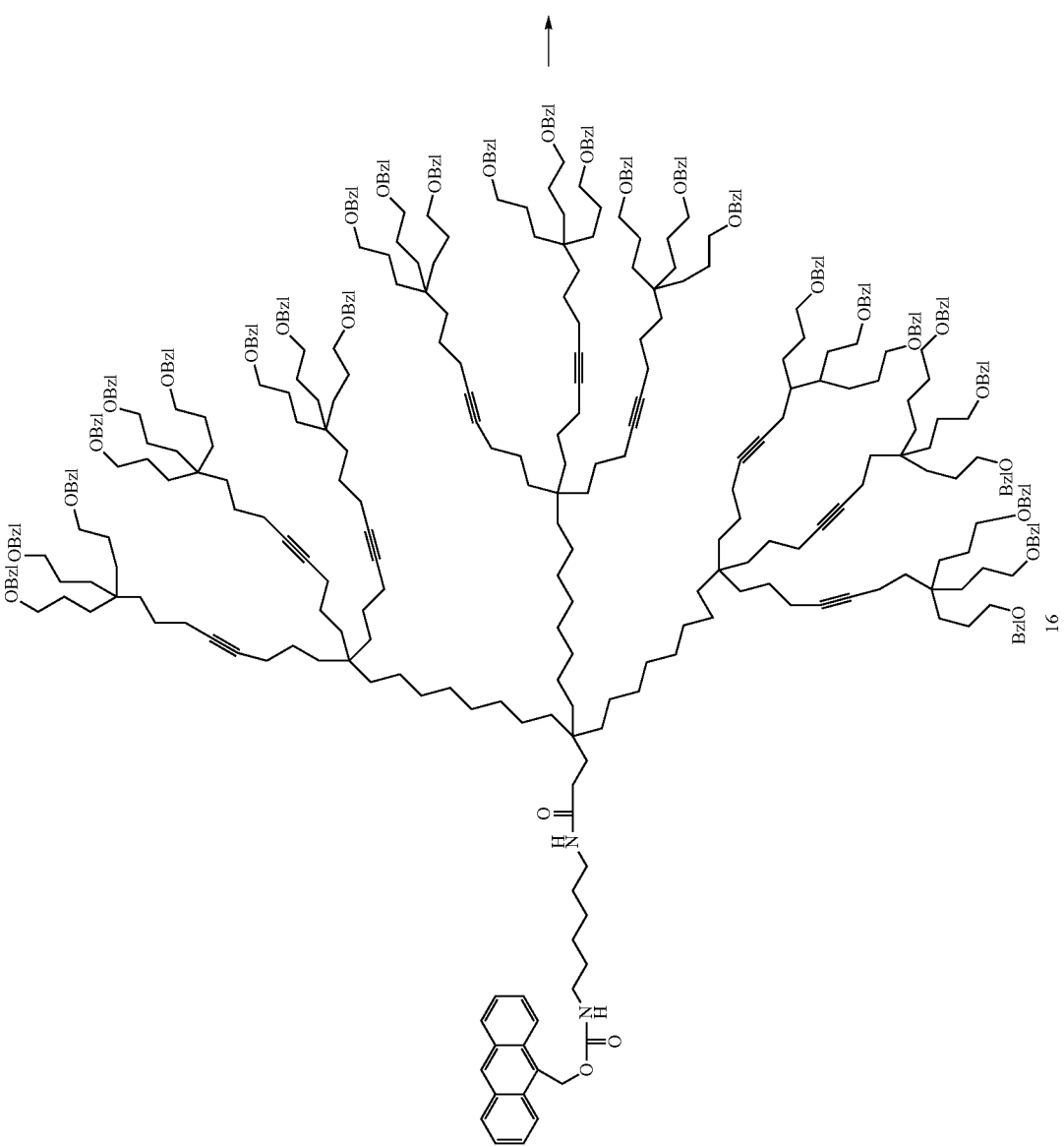
16

-continued
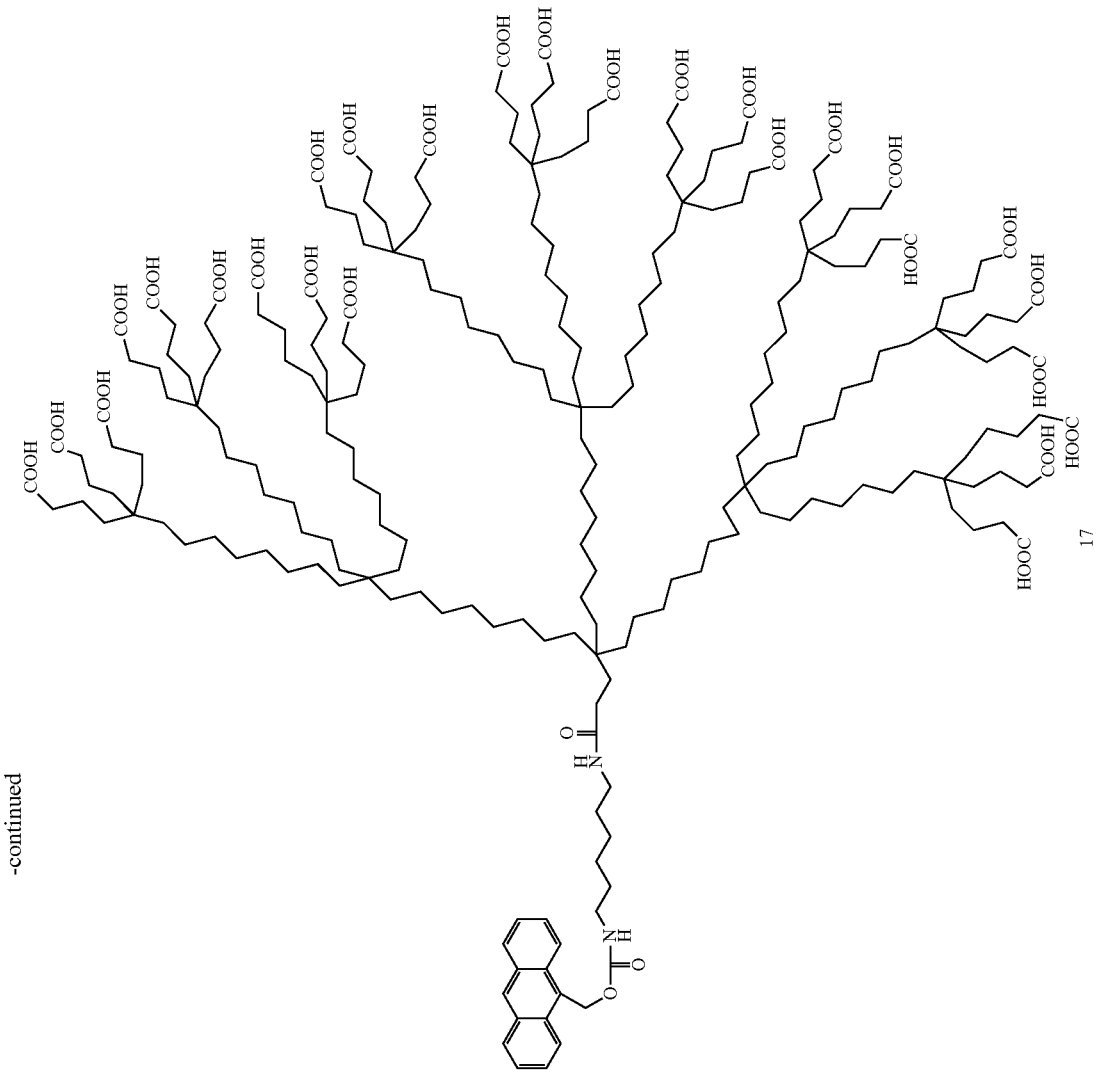
17

The alcohol was smoothly converted into the nonabromide employing SOBr₂ in CH₂Cl₂ at 40° C. for 12 h. And then the nonabromide compound was alkylated with 12 equivalents of [1]-Alkyne-[3]-OBzl 13 to give 49% of A-[9]-Alkyne-[27]-OBzl 16. A-[9]-Alkyne-[27]-OBzl 16 were reduced and deprotected in one step with Pd—C/H in EtOH and THF solution including 10% Pd—C/H at 60□ for 4 d yielding 89% of A-[27]-OH. A-[27]-OH was oxidized by RuO₄ treating with NH₄OH or (CH₃)₄NOH to achieve 85% of A-[27]-COOH 17.

Example 3.8

1) [G1]-(OMe)₂ (3)

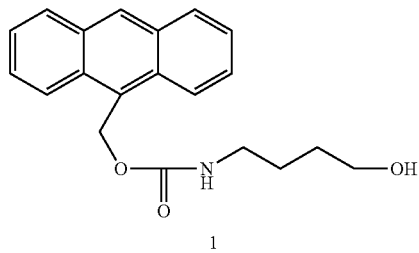

A mixture of compound 1 (1.05 mol equiv.), 3,5-dimethoxybenzyl bromide (1.00 mol equiv. 2), potassium carbonate (1.1 mol equiv.) and 18-c-6 (0.2 mol equiv.) in dry acetone was heated at reflux under nitrogen for 48 h. The mixture was cooled and evaporated to dryness, and the residue was partitioned between CH₂Cl₂ and water. The aqueous layer was extracted with CH₂Cl₂ (3×), and the combined organic layers were dried and evaporated to dryness. The crude product was purified by flash chromatography with EtOAc-CH₂Cl₂ as eluent to give compound 3.

2) [G1]-(OH)₂ (4)

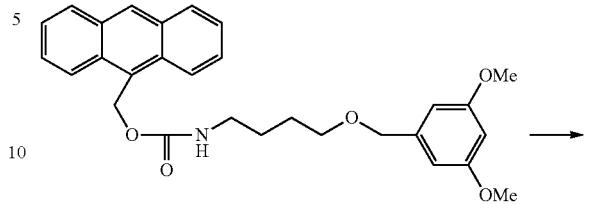

Methyl ether group of compound 3 was deprotected by BBr₃ in EtOAc solution for 1 h, and the crude product was purified by flash chromatography with MeOH-EtOAc as eluent to give compound 4.

3) [G2]-(OMe)₄ (5)

A mixture of [G1]-(OH)$_2$ (1.00 mol equiv. 4), 3,5-dimethoxybenzyl bromide (2.00 mol equiv. 2), potassium carbonate (2.1 mol equiv.) and 18-c-6 (0.2 mol equiv.) in dry acetone was heated at reflux under nitrogen for 48 h. The mixture was cooled and evaporated to dryness, and the residue was partitioned between CH$_2$Cl$_2$ and water. The aqueous layer was extracted with CH$_2$Cl$_2$ (3×), and the combined organic layers were dried and evaporated to dryness. The crude product was purified by flash chromatography with EtOAc-CH$_2$Cl$_2$ as eluent to give compound 5.

4) [G2]-(OH)$_4$ (6)

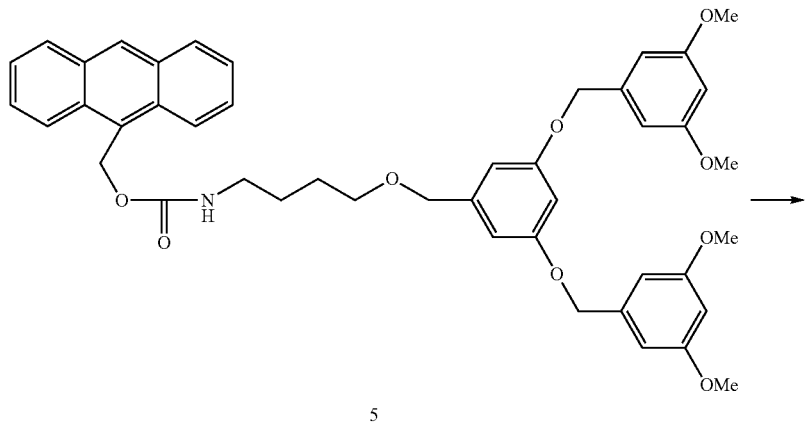

5

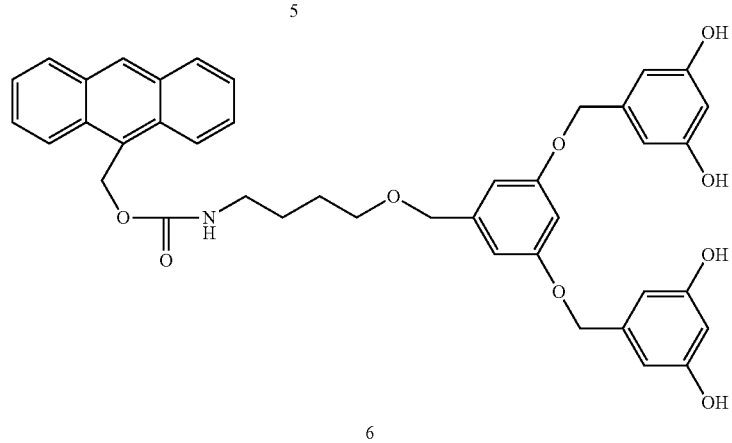

6

Methyl ether group of compound 5 was deprotected by BBr$_3$ in EtOAc solution for 1 h, and the crude product was purified by flash chromatography with MeOH-EtOAc as eluent to give compound 4.

5) [G3]-(OMe)$_8$ (7)

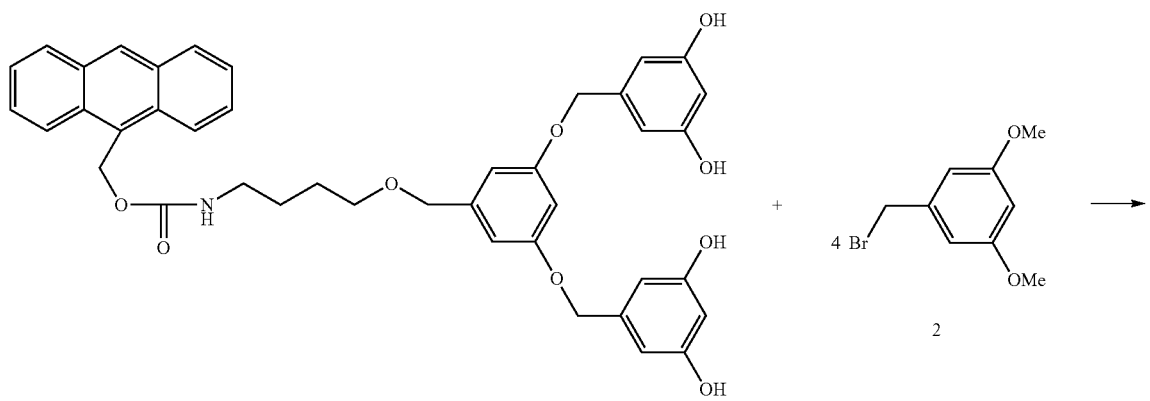

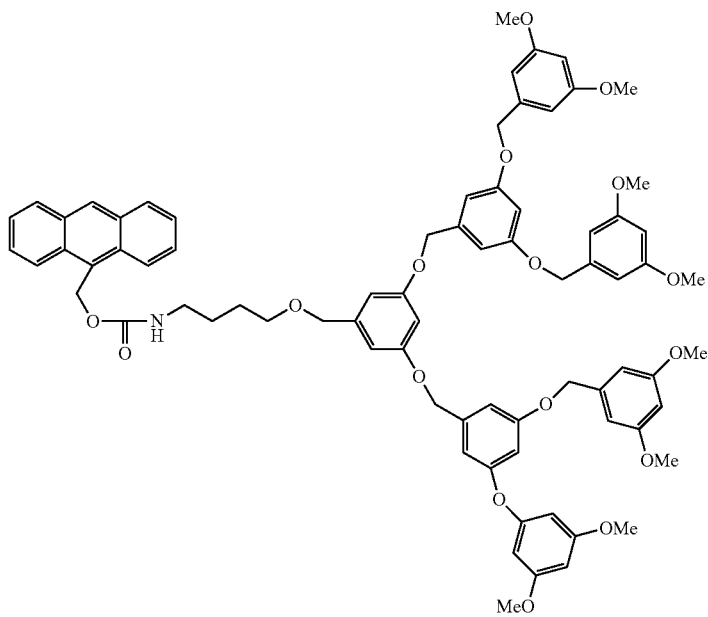

7

A mixture of [G2]-(OH)₄ (1.00 mol equiv. 6), 3,5-dimethoxybenzyl bromide (4.00 mol equiv. 2), potassium carbonate (4.1 mol equiv.) and 18-c-6 (0.2 mol equiv.) in dry acetone was heated at reflux under nitrogen for 48 h. The mixture was cooled and evaporated to dryness, and the residue was partitioned between CH₂Cl₂ and water. The aqueous layer was extracted with CH₂Cl₂ (3×), and the combined organic layers were dried and evaporated to dryness. The crude product was purified by flash chromatography with EtOAc-CH₂Cl₂ as eluent to give compound 7.

6) [G3]-(OH)₈ (8)

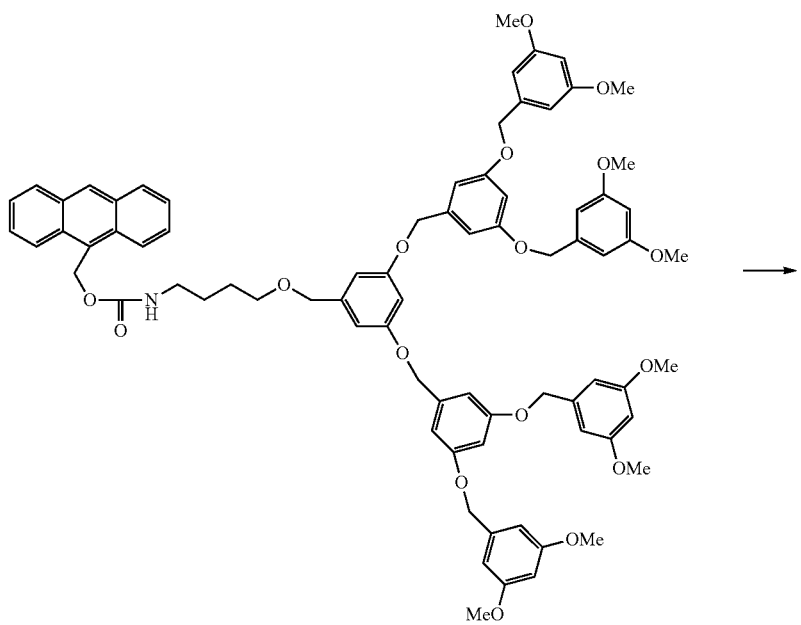

8

-continued

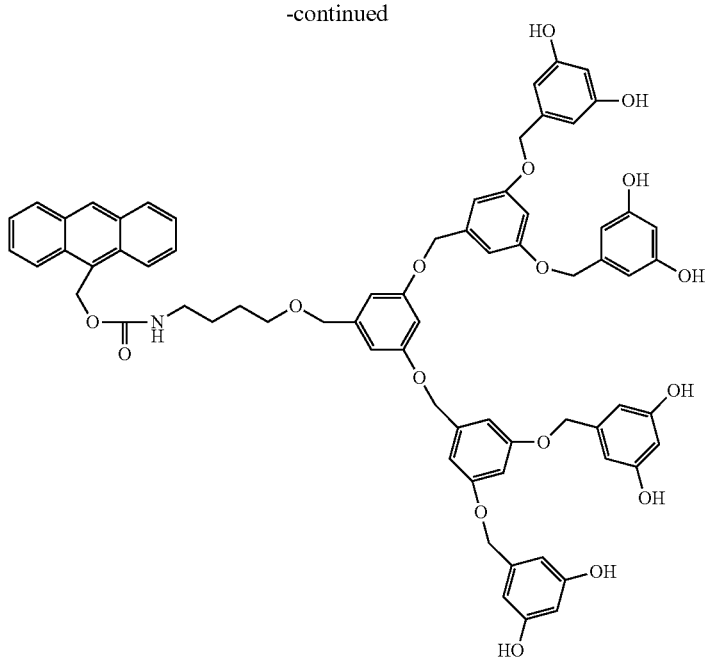

Methyl ether group of compound 7 was deprotected by BBr₃ in EtOAc solution for 1 h, and the crude product was purified by flash chromatography with MeOH-EtOAc as eluent to give compound 8.

Example 4

Assembly of the Dendron on a Substrate

TMAC (N-trimethoxysilylpropyl-N,N,N-trimethylammonium chloride) was self-assembled on oxide glass instead of APDES. The dendrimer layer on TMAC layer did not need to cap the residual amine.

Aminosilylation with TMAC.

Clean substrates (slide glass) were placed into a solution of TMAC (2 mL) and acetone (100 mL) for 5 h. After the self-assembly, the substrates were taken out of the flask, washed with acetone. The substrates were placed in an oven, and heated at 110° C. for 40 min. After immersion in acetone, the substrates were sonicated for 3 min. The washed substrate was placed in a Teflon vessel, and placed in a glass container with a big screw cap lined with an O-ring, and eventually the container was evacuated (30-40 mTorr) to dry the substrate.

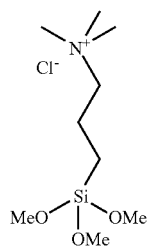

Structure of TMAC (N-trimethoxysilylpropyl-N,N,N-trimethylammonium chloride)

Self-assembly of the Fmoc-spacer-[9]acid was performed in same condition to the case of CBz-[9]acid with exception of capping of the residual amines by acetic anhydride Self-Assembly of the Fmoc-Spacer-[9]acid (5).

A certain amount of the Fmoc-spacer-[9]acid (5) was dissolved in a mixed solvent (DMF:deionized water=1:1 (v/v)) to make a solution of 20 mL. The solution was added into a Teflon vessel, and subsequently pieces of the above prepared aminosilylated slide glass were placed in the solution. While allowing the flask at room temperature to self-assemble, each piece of the substrate was taken out of the solution after 1 day. Right after being taken out, the plate was washed with a copious amount of deionized water. Each substrate was sonicated for 3 min in deionized water, a mixture of deionized water-methanol (1:1 (v/v)), and methanol in a sequential manner. After sonication, the substrates were placed in a Teflon vessel, and placed in a glass container with a big screw cap lined with an O-ring, and eventually the container was evacuated (30-40 mTorr) to dry the substrate.

Deprotection of Fmoc from the Self-Assembled Fmoc-Spacer-[9]acid (5).

Teflon vessels containing 5% piperidine in DMF were prepared. The self-assembled substrates were immersed in the vessels, and stirred for 20 min. Each substrate was sonicated for 3 min in acetone, and MeOH in a sequential manner and evacuated in a vacuum chamber (30-40 mTorr).

Example 5

Preparation of Dendron-Modified AFM Tip and Substrate

Materials

The silane coupling agent N-(3-(triethoxysilyl)propyl)-O-polyethyleneoxide urethane (TPU) was purchased from Gelest Inc. All other chemicals are of reagent grade from Sigma-Aldrich. The UV-grade fused silica plates were purchased from CVI Laser Co. The polished prime Si(100) wafers (dopant, phosphorus; resistivity, 1.5-2.1 Ω·cm) were purchased from MEMC Electronic Materials Inc. Deionized water (18 MΩ·cm) was obtained by passing distilled water through a Barnstead E-pure 3-Module system. Thickness was measured with a variable angle ellipsometer (Model M-44) from J. A. Woolam Co. UV-vis spectra were recorded with a Hewlett-Packard diode array 8453 spectrophotometer.

1) Cleaning the Substrates.

Fused silica plates and silicon wafers were sonicated in Piranha solution (concentrated $H_2SO_4$:30% $H_2O_2$=7:3 (v/v)) for 4 h (Caution: Piranha solution can oxidize organic materials explosively. Avoid contact with oxidizable materials.). The plates and the wafers were washed and rinsed thoroughly with deionized water after the sonication. Subsequently, the substrates were immersed in a mixture of deionized water, concentrated ammonia solution, and 30% hydrogen peroxide (5:1:1 (v/v/v)) contained in a Teflon beaker. The beaker was placed in a water bath and heated at 80° C. for 10 min. The substrates were taken out of the solution and rinsed thoroughly with deionized water. Again, the substrates were placed in a Teflon beaker containing a mixture of deionized water, concentrated hydrochloric acid, and 30 % hydrogen peroxide (6:1:1 (v/v/v)). The beaker was heated at 80° C. for 10 min. The substrates were taken out of the solution and washed and rinsed thoroughly with a copious amount of deionized water. The clean substrates were dried in a vacuum chamber (30-40 mTorr) for about 20 min and used immediately in the following steps.

2) Cleaning the Tip.

The standard V-shaped silicon nitride cantilevers (MLCT-AUNM) with pyramidal tips (Veeco Instrument; k=10 pN/nm) were first activated by dipping in 10% nitric acid and heating at 80° C. for 20 min. The cantilevers were taken out of the solution and washed and rinsed thoroughly with a copious amount of deionized water. The clean cantilevers were dried in a vacuum chamber (30-40 mTorr) for about 20 min and used immediately in the following steps.

3) Aminosilylation.

Clean fused silica, silicon wafer, and cantilevers were immersed into anhydrous toluene (20 mL) containing the coupling agent (0.20 mL) under nitrogen atmosphere, and placed in the solution for 6 h. After silylation, the substrates and cantilevers were washed with toluene, baked for 30 min at 110° C. The substrates were immersed in toluene, toluene-methanol (1:1 (v/v)), and methanol in a sequential manner, and they were sonicated for 3 min in each washing solution. The cantilevers rinsed thoroughly with toluene and methanol in a sequential manner. Finally the substrates and cantilevers were dried under vacuum (30-40 mTorr).

4) Preparation of Dendron Modified Surface.

The above hydroxylated substrates and cantilevers were immersed into a methylene chloride solution with a small amount of DMF dissolving the dendron (1.0 mM) and a coupling agent, 1,3-dicyclohexylcarbodiimide (DCC) (9.9 mM) in the presence of 4-dimethylaminopyridine (DMAP) (0.90 mM) for 12~24 h. The dendron (9-anthrylmethyl N-({[tris({2-[({tris[(2-carboxyethoxy)methyl]methyl}amino)carbonyl]ethoxy}methyl)methyl]amino}carbonyl)propylcarbamate) used in this work was prepared in this group. After reaction, the substrates were immersed in methylene chloride, methanol, and water in a sequential manner, and they were sonicated for 3 min at each washing step. The cantilevers were rinsed thoroughly with methylene chloride, methanol, and water in a sequential manner. Finally the substrates and cantilevers were washed with methanol, and dried under vacuum (30-40 mTorr).

Example 6

Immobilization of Oligonucleotides

1) Deprotection of Carboanthrylmethoxy Group from the Dendron Surface.

The dendron modified substrates and cantilevers were immersed into a methylene chloride solution with 1.0 M trifluoroacetic acid (TFA), and they were stirred for 3 h. After the reaction, they were soaked in a methylene chloride solution with 20% (v/v) diisopropylethylamine (DIPEA) for 10 min. The substrates were sonicated in methylene chloride and methanol each for 3 min and the cantilevers were rinsed thoroughly with methylene chloride and methanol in a sequential manner. The substrates and cantilevers were dried under vacuum (30-40 mTorr).

2) Preparing the NHS-Modified Substrates.

The above deprotected substrates and cantilevers were immersed into an acetonitrile solution with di(N-succinimidyl)carbonate (DSC) (25 mM) and DIPEA (1.0 mM) for 4 h under nitrogen atmosphere. After the reaction, the substrates and cantilevers were placed in stirred dimethylformamide for 30 min and washed with methanol. The substrates and cantilevers were dried under vacuum (30-40 mTorr).

3) Immobilization of Oligonucleotides on the Dendron Modified Substrates.

The above NHS-modified substrates and cantilevers were soaked in an oligonucleotide (20 μM) in 25 mM $NaHCO_3$ buffer (pH 8.5) with 5.0 mM $MgCl_2$ for 12 h. After the reaction, the substrates and cantilevers were stirred in a hybridization buffer solution (2×SSPE buffer (pH 7.4) containing 7.0 mM sodium dodecylsulfate) at 37° C. for 1 h and in boiling water for 5 min to remove non-specifically bound oligonucleotide. Finally the substrates and cantilevers were dried under vacuum (30-40 mTorr). The oligonucleotides to be immobilized are shown in Table 1.

Example 7

AFM Force Measurements 7-1: Sample Preparation

To understand effect of the spacing, the two types of the modification (9-acid/GPDES substrate and 9-acid/TPU substrate) were employed for the substrate by using the two silane agents such as GPDES and TPU, while spacing on AFM tip was fixed with use of 9-acid/TPU. The surface modification of the substrate was performed according to Examples 1. The oligonucleotides as shown in SEQ ID NOs: 1 to 4 were immobilized on the 9-acid/TPU substrate, respectively according to Example 2. The 30 bp complementary DNA as represented by SEQ ID NO: 2 was immobilized on the 9-acid/GPDES substrate. The oligonucleotides as shown in SEQ ID NOs: 5 to 20 were immobilized on the 9-acid/TPU type of AFM tip, respectively.

TABLE 2

| | Surface | Type of oligonucleotide | Immobilized nucleotide (SEQ ID NO) |
|---|---|---|---|
| AFM tip | 9-acid/TPU | Perfect match DNA | 5 to 8 |
| | 9-acid/TPU | 1 bp mismatch | 9 to 12 |
| | 9-acid/TPU | 2 bp mismatch | 13 to 16 |
| Substrate | 9-acid/GPDES | DNA | 1 to 4 |
| | 9-acid/TPU | DNA | 1 to 4 |
| | 27-acid/TPU | DNA | 1 to 4 |

In the example, 9-acid dedron is (9-anthrylmethyl N-({[tris({2-[({tris[(2-carboxyethoxy)methyl]methyl}amino)carbonyl]ethoxy}methyl)methyl]amino}carbonyl)propylcarbamate), and 27-acid dedron is described in Example 3.

7-2: AFM Force Measurement

All force measurements were performed with a NanoWizard AFM (JPK Instrument). The spring constant, $k_c$, of each individual AFM tip was calibrated in solution before each experiment by thermal fluctuation method available via a NanoWizard software. The spring constant varied between 12 and 15 pN/nm. All measurements were carried out in a fresh PBS buffer (pH 7.4) at room temperature. The loading rate of force measurements varied between 110 nm/s and 540 nm/s. At each experimental condition, force curves were recorded more than one hundred times at a spot, and at least more than 5 spots were examined. In these measurements, both binding and unbinding force curves were recorded. To calculate distance that the tip actually moved, the cantilever displacement was subtracted from the piezo displacement. The cantilever displacement was obtained by dividing the force by the cantilever spring constant.

7-3: Unbinding Force for 9-Acid/GPDES Substrate Immobilized by a Complementary 30-Base Pair DNA Using the oligonucleode as shown in SEQ ID NO: 2 immobilized on 9-acid/GPDES substrate, and the oligonucleode as shown in SEQ ID NO: 6 immobilized on 9-acid/TPU AFM tip, AFM force measurement was performed at various loading rate in the range between 110 nm/s and 540 nm/s according to AFM measurement of example 3-2 to obtain unbinding force distribution (FIG. 4A) at a retraction rate of 110 nm/s, and force distance curve (FIG. 4B) and unbinding force distribution (FIG. 4C) at a retraction rate of 540 nm/s.

Figure 4A:
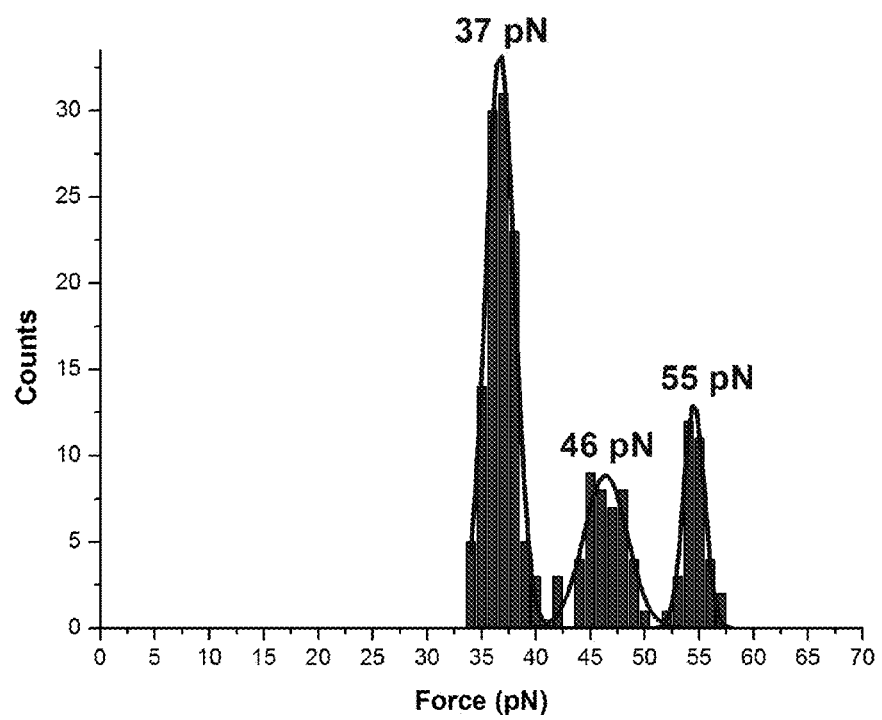
FIG. 4A is a histogram showing the force distribution for a complementary 30-base pair with relatively narrow spacing at a retraction velocity of 110 nm/s.
Figure 4B:
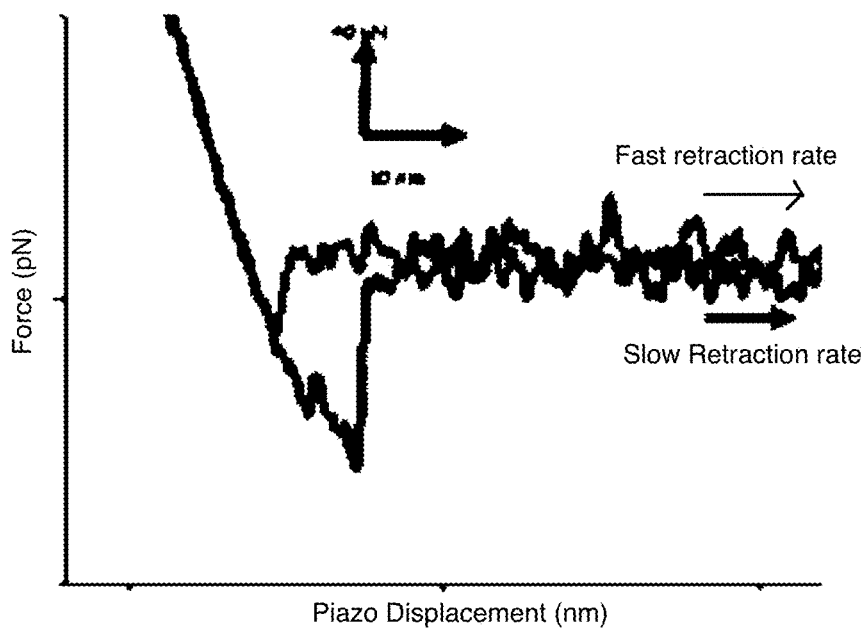
FIG. 4B to FIG. 4C are direct measurements of single unbinding force of complementary 30 base pairs with a retraction velocity of 540 nm/s.
Figure 4C:
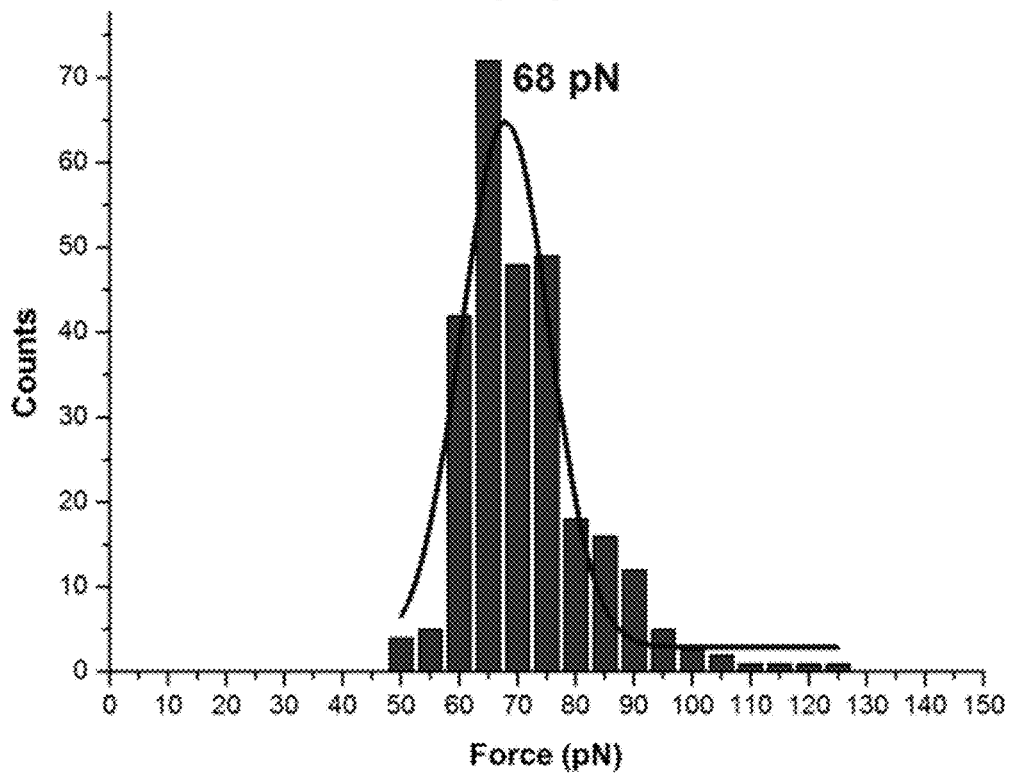

A large unbinding force, attributable to an interaction of multiple oligonucleotides, was observed at 540 nm/s retraction rate (FIG. 4B). Also, the histogram is rather broad (the maximum half-width is 15 pN.) and unresolved (FIG. 4C). However, at 110 nm/s refraction rate the histogram (FIG. 4A) was resolved into three peaks, and each peak was sharp (the maximum half-width is 3 pN for the first peak.). Exact interpretation of the behavior is not straightforward, but the first peak at 37 pN is very likely to be from single DNA-DNA interaction (vide infra) and the other two (46 pN and 55 pN) represent unbinding events with the secondary interaction in addition to the single one.

FIG. 4A is a histogram showing the force distribution of a complementary 30-base pair when relatively narrow spacing (realized with a dendron on the GPDES substrate). FIG. 4B is a direct measurement of single unbinding force of complementary 30 base pairs with a retraction velocity of 540 nm/s. FIG. 4B is a force versus distance curve measured between complementary 30 base pairs with a retraction velocity of 540 nm/s. Much larger force (blue curve), attributable to interactions of multiple oligonucleotides, can be observed at 540 nm/s retraction rate (For comparison, unbinding force (red curve) observed in 110 nm/s retraction rate is displayed.). FIG. 4C shows the probability distribution of unbinding force with a retraction velocity of 540 nm/s. The histogram shows the observed force distribution with relatively narrow spacing (realized with the dendron on the GPDES surface). The maximum of the distribution is found by a Gaussian fit to be 68±13 pN, and the distribution curve is not resolved to show single interaction.

Figure 5A:
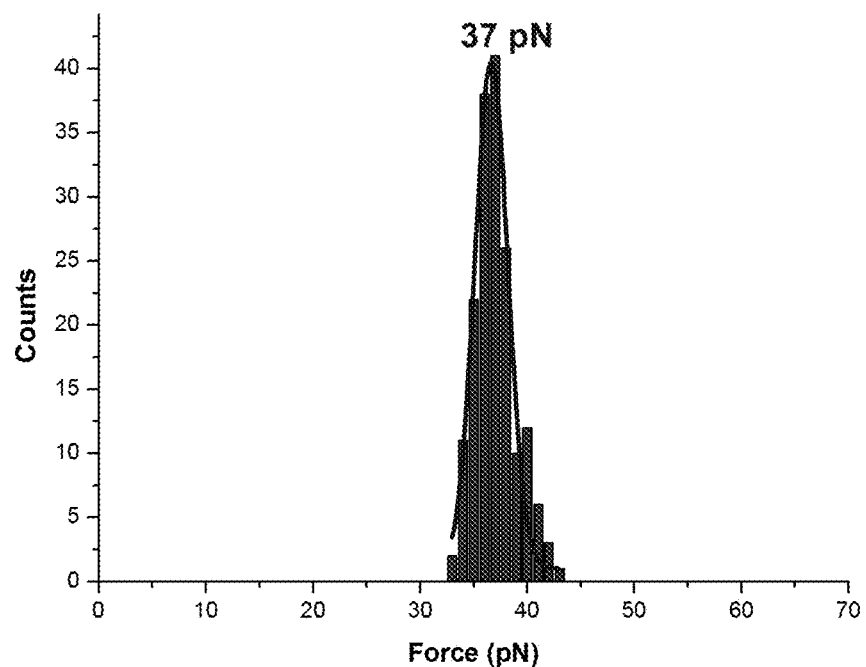
FIG. 5A is a histogram showing for a complementary 30-base pair with relatively broad spacing at a retraction velocity of 110 nm/s.

7-4: Binding Force and Unbinding for 9-Acid/TPU Substrate Immobilized by a Complementary 30-Base Pair DNA Using the oligonucleode as shown in SEQ ID NO: 2 immobilized on 9-acid/TPU substrate, and the oligonucleode as shown in SEQ ID NO: 6 immobilized on 9-acid/TPU AFM tip, AFM force measurement was performed at a retraction rate of 110 nm/s according to AFM measurement of example 3-2 to obtain unbinding force distribution (FIG. 5A), binding force vs distance curve (FIG. 5B), and binding force distribution curve (FIG. 5C).

When the DNA was immobilized on 9-acid/TPU surface, the unbinding force histogram (FIG. 5A) showed only one peak at 37±2 pN, and the narrowness of the peak was not tarnished. Disappearance of the minor peaks at 46 pN and 55 pN confirms that these peaks represent events associated with the secondary interaction. For analysis of the above two cases, only unusual curves were discarded, and more than 90% of measurements were included in the plot. While the curves are frequently indented for 9-acid/GPDES case, none of the curves for 9-acid/TPU showed any indentation. Thus, it is possible to measure single DNA-DNA interaction by modifying the substrate surface with TPU as a silane agent, because of the sufficient spacing.

Figure 5B:
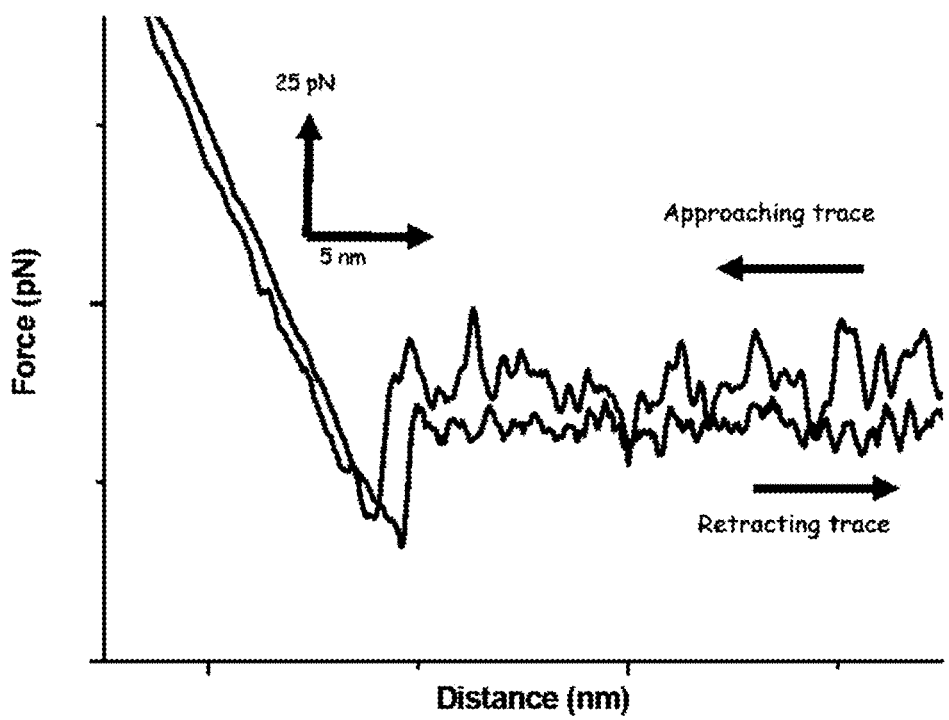
FIG. 5B to FIG. 5C are measurements of binding force of a complementary 30 base pair at a retract velocity of 110 nm/s.
Figure 5C:
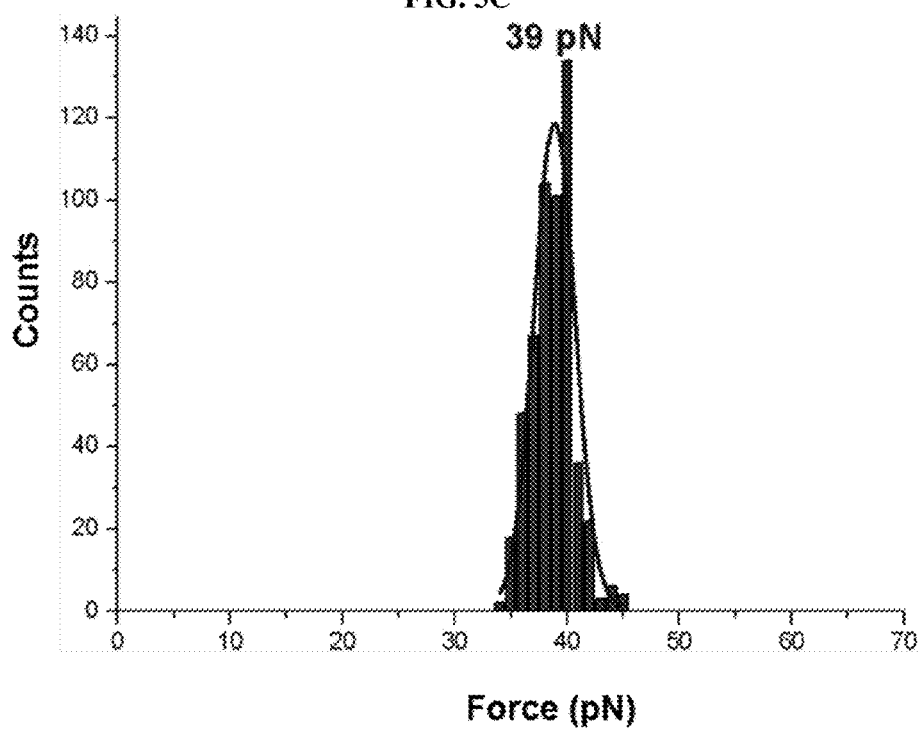

The binding force curves were observed every time when the tip approached the dendron-modified surface (FIG. 5B). In this particular process, again 9-acid/TPU-modified surface produced single dip force curves, while 9-acid/GPDES case frequently showed double- or multiple-dipped force curves. Because the behavior was so consistent and reproducible, not a single datum had to be discarded to generate the histogram. As in the histogram for the unbinding event, the peak is narrow (the maximum half-width is 3 pN.), and the value of 39 pN is pretty close to that of the unbinding case. It is intriguing to find that such unprecedented binding process can be observed when the spacing between DNAs was controlled properly.

Moreover, it was found that the binding force behavior is less dependent on the loading rate. In other word, the same histogram (FIG. 5C) was obtained at any loading rate between 70 nm/s and 540 nm/s. The particular experiment was repeated many times using different tips and samples, and the above binding behavior and the histogram were consistently reproduced.

7-5: Unbinding Force for 27-Acid and TPU Modified Substrate for Examining Single Strand Interaction Previously, unbinding force of 48 pN for other complementary 30-base DNA was recorded even at a slower retraction rate (T. Strunz, K. Oroszlan, R. Schäfer, H.-J. Güntherodt, Proc. Natl. Acad. Sci. U.S.A. 96, 11277, 1999). It is interesting to observe a smaller unbinding force even with DNA with the same GC content.

In order to examine whether these interactions are from a single strand or multiple strands, a higher generation dendron, 27-acid, was employed. The third generation dendron is expected to provide spacing around 10 nm. Spacing on the substrate was increased with a combination of 27-acid and TPU, while AFM tip was modified with 9-acid/TPU. It was interesting to note the histogram was exactly same as that of 9-acid/TPU case. The AFM tip was modified with 27-acid/TPU, and observed again the same histogram. The only difference is a reduced chance of observing the unbinding. For the last case, about 50% of the refraction events did not show the unbinding phenomenon at all. This change seems reasonable, because too big spacing between the oligonucleotides reduces chance of the hybridization. This behavior showed clearly spacing generated from 9-acid/TPU was already large enough for realization of single strand interaction.

7-6: Binding Force and Unbinding Force for Complementary DNA Duplexes

Prior to testing other oligonucleotides, the accuracy of the force measurement was tested in the above condition. Samples from different batches were prepared, and the cantilevers were calibrated. The inventors found that the variation was within 10-15%. The value suggests that reproducible and precise control of the surface allows minimal error: the value never goes beyond the error associated with spring constant calibration. With 9-acid/TPU-modified surface, binding and unbinding events of DNA duplexes of 20, 30, 40, and 50 base pairs (Table 1) were performed at the 110 nm/s loading rate. Force-distance curves were obtained on each duplex during the approach and retract cycles.

As previously mentioned above, binding and unbinding histograms were almost the same, and average force values were identical. The binding force histogram, and the unbinding force histogram of complementary DNA duplexes with 20, 30, 40 and 50 base pairs, were shown in FIG. 6A, and FIG. 6C, respectively.

Figure 6A:
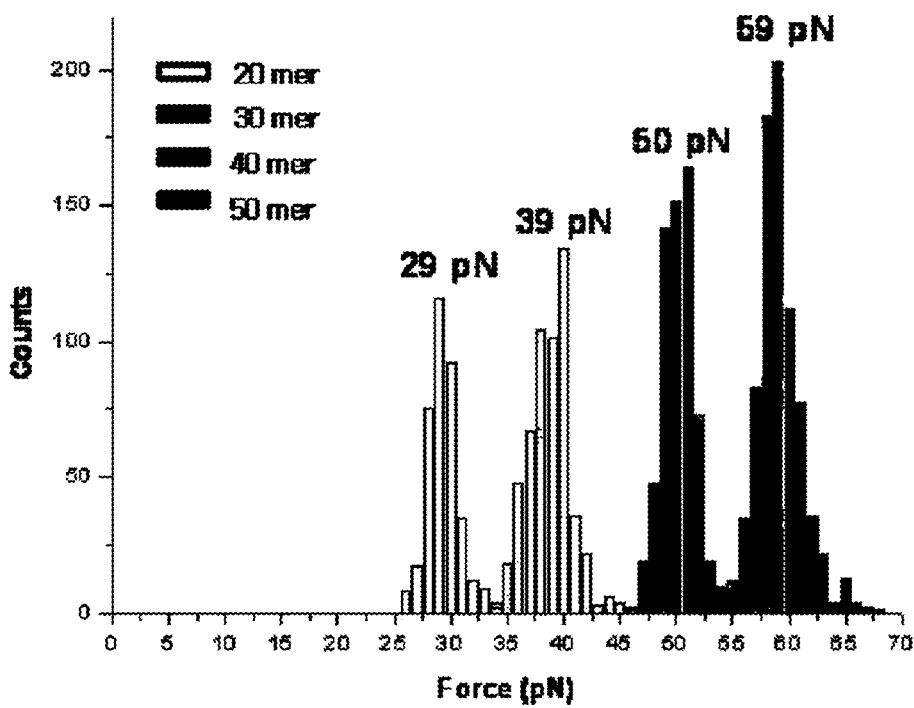
FIG. 6A and FIG. 6B are a histogram showing the binding force distributions on complementary DNA duplexes.

In the histogram as shown in FIG. 6A, non-overlapped peaks, and clear increment of the force with the length of DNA were seen. The values are 29 pN, 39 pN, 50 pN, and 59 pN for 20, 30, 40, and 50 base pairs. Coincidentally the increment of the force is roughly 10 pN at each increase of 10 DNA bases. For verification, the forces of non-complementary DNA strands were measured. In all cases, force curves were mostly not detected, and with a low probability, a tiny force of 10 pN was recorded.

Figure 6B:
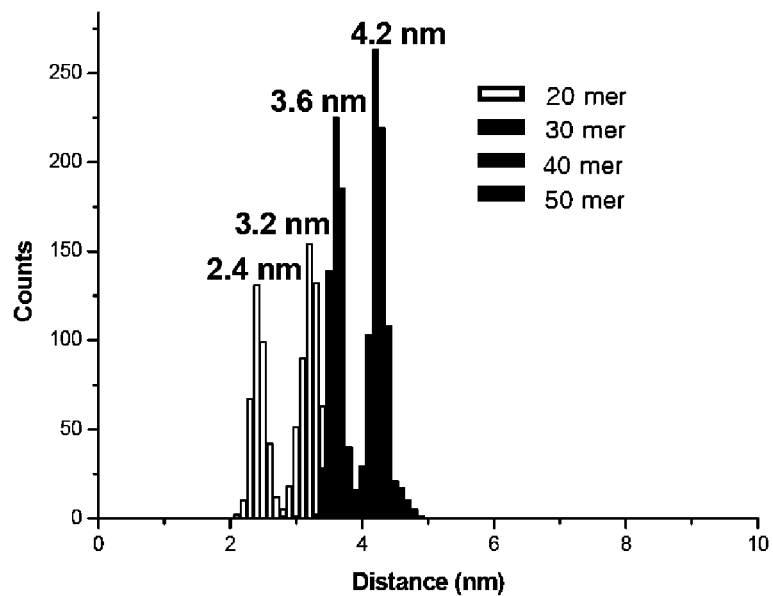
Figure 6C:
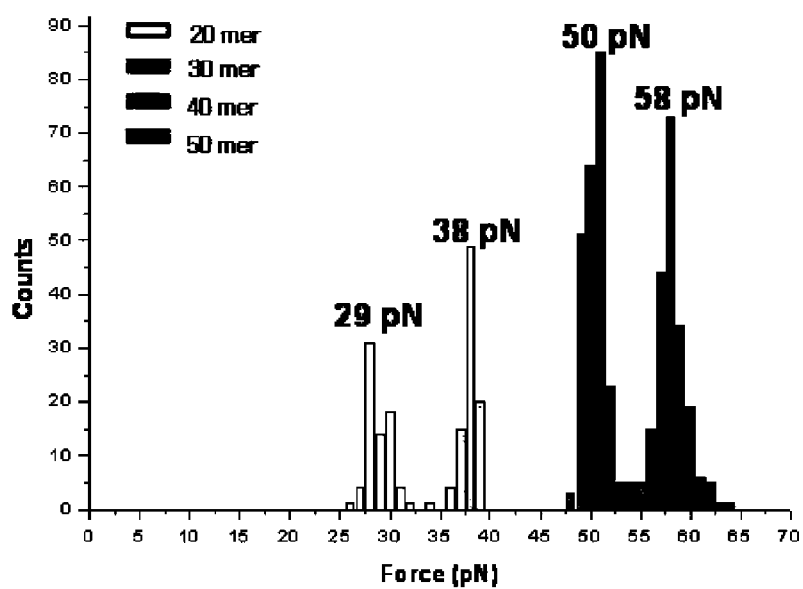
FIG. 6C is a histogram showing the unbinding force distributions on complementary DNA duplexes.

In FIG. 6B for force-piezo displacement curve of complementary DNA duplexes with 20, 30, 40 and 50 base pairs was obtained by calculating from the binding force distribution of FIG. 4. The observed distance that the tip moved towards the surface to relieve the strain upon the binding event was retrieved from the force-piezo displacement curve and the value was plotted. In the particular situation, distances of 2.4 nm, 3.2 nm, 3.6 nm, and 4.2 nm were recorded for 20-mer, 30-mer, 40-mer, and 50-mer cases. Because the peaks are quite narrow, and the distance increases almost linearly with the DNA length, the parameter should be diagnostic for analyzing the interaction DNA length in unknown samples.

7-7: Binding Force Distribution for Mismatched DNA Duplexes

Figure 7:
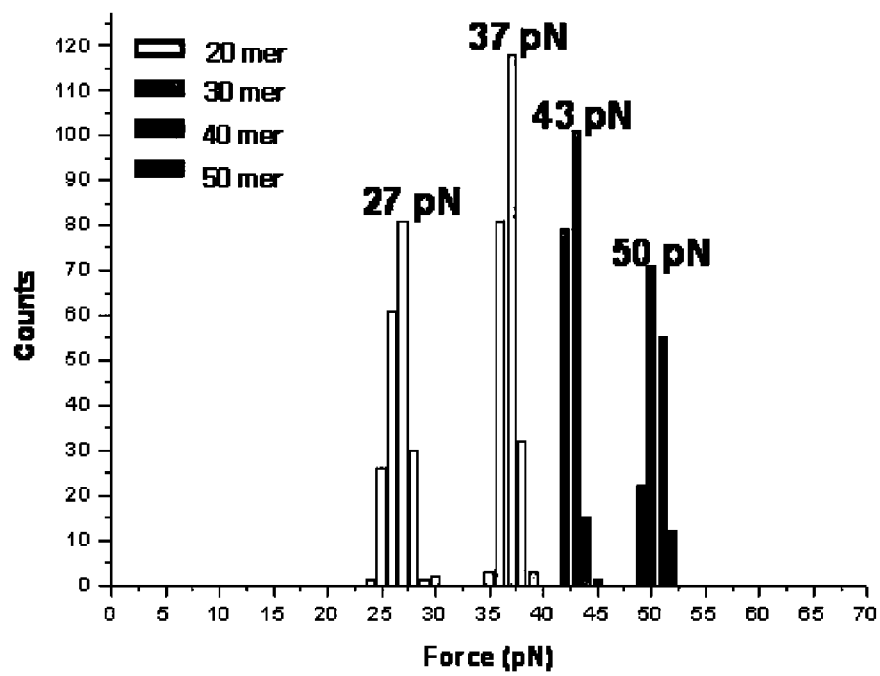
FIG. 7 is a histogram showing the binding force distributions for single base mismatched DNA duplexes.
Figure 8:
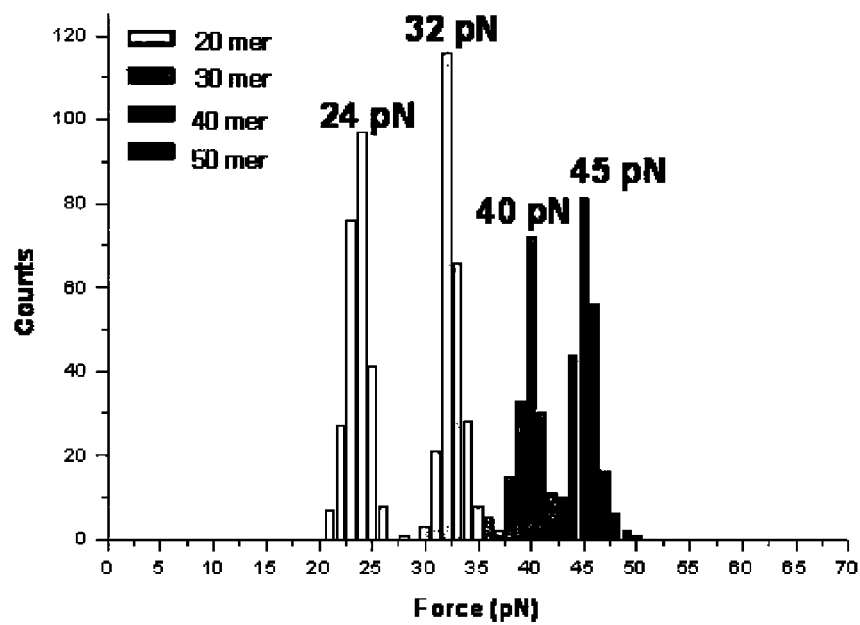
FIG. 8 is a histogram showing the binding force distributions on double base mismatched DNA duplexes.
Figure 9:
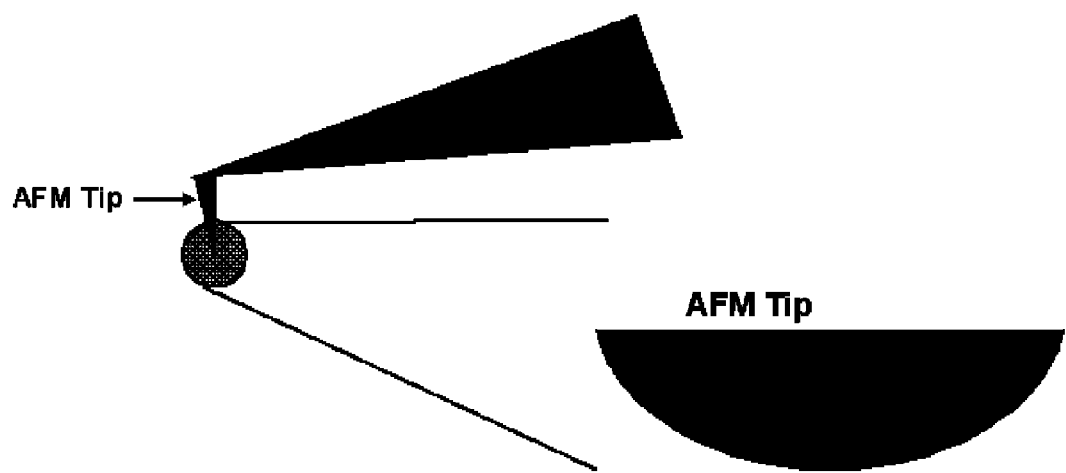
FIG. 9 shows a schematic drawing of a cantilever for an AFM and an enlarged view of a tip of an AFM cantilever.
Figure 10:
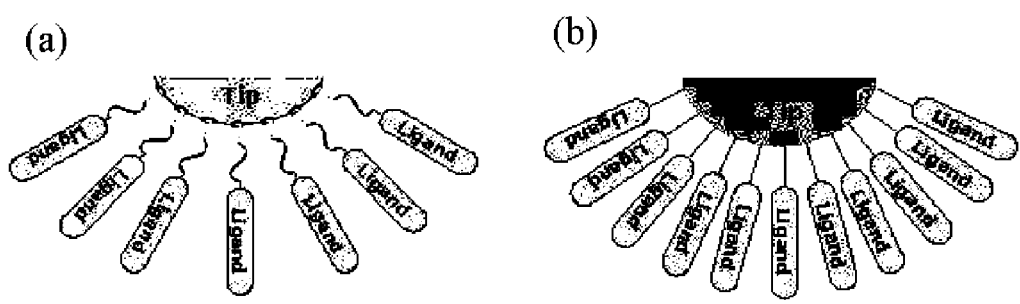
FIG. 10a shows the schematic view of the dendron-modified AFM tip tethered with ligands having enough spacing.
FIG. 10b shows the schematic view of the AFM tip tethered with the closely packed ligands.

To further probe this recognition phenomenon, interaction force curves were recorded for the single base and double base mismatched pairs (Table 1). Using the oligonucleodes as shown in SEQ ID NO: 5 to 8 immobilized on 9-acid/TPU substrate for single base mismatched DNA, the oligonucleodes as shown in SEQ ID NO: 9 to 12 immobilized on 9-acid/TPU substrate for double base mismatched DNA, and the oligonucleode as shown in SEQ ID NO:1 to 4 immobilized on 9-acid/TPU AFM tip, AFM force measurements were performed at a retraction rate of 110 nm/s according to AFM measurement of example 3-2 to obtain binding force distribution for single base mismatched DNA duplexs (FIG. 7), and binding force distribution for double base mismatched DNA duplexs (FIG. 8).

As expected, it was observed that the introduction of the mismatch decreased binding and unbinding forces. As shown in FIG. 7 for single base mismatched pairs, binding force of 27 pN, 37 pN, 43 pN, and 50 pN was observed for 20-mer, 30-mer, 40-mer, and 50-mer, respectively. As shown in FIG. 8 for double base mismatched pairs, binding force of 24 pN, 32 pN, 40 pN, and 45 pN was observed for 20-mer, 30-mer, 40-mer, and 50-mer, respectively.

As in the previous case for complementary DNA duplex, binding and unbinding forces were identical. However, for single base mismatch cases, there were only marginal decrease (2 pN) for both 20 mer and 30 mer. Meanwhile, substantial decrease (>7 pN) was observed for 40 mer and 50 mer. The result shows that use of DNA longer than 40 mer guarantees reliable detection of single point mutation. As expected, larger reduction of the force was observed for the double base mismatched pairs. For examples, decrease of 5 pN was observed for 20 mer, while 14 pN was observed for 50 mer. It is worthwhile to note the capability of picoforce AFM for detecting a single point mutation at the single molecular level.

Example 8

Biomolecular Interaction Between Signal Transducer Proteins

Figure 11:
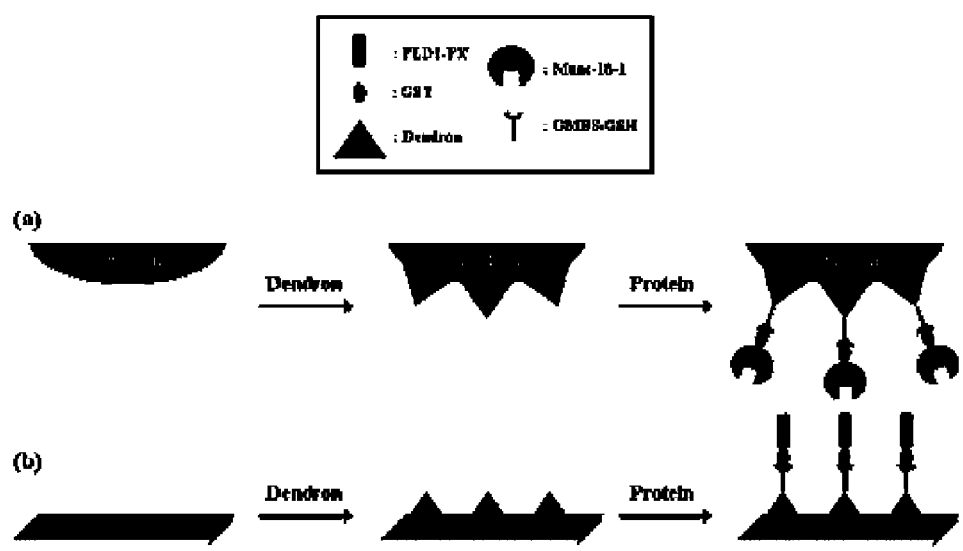
FIG. 11a shows the schematic drawing of the method of immobilizing a protein on the dendron-modified AFM tip.
FIG. 11b shows the schematic drawing of the method of immobilizing a protein on the dendron-modified substrate.

Previous studies showed that a dendron-modified surface can ensure enough spacing between biomolecules attached on surface by controlling the size of the dendron molecule. In this study, an AFM tip and a solid substrate such as a Si wafer were also functionalized with a dendron molecule, as described in the previous published paper (*Langmuir* 2005, 21, 4257) and U.S. patent application Ser. No. 10/917,601, to improve the recognition efficiency between proteins at the single molecular level (FIG. 11). The dendron molecule used here is the same as the previous one (*Langmuir* 2005, 21, 4257), but all dendron molecules referenced in U.S. patent application Ser. No. 10/917,601 can be utilized for this study.

After the deprotection of a protecting group, the dendron-modified substrate was incubated in a 50 mM NaHCO$_3$ buffer (pH 8.5) with a small amount of DMF dissolving N-succinimidyl-4-maleimidobutylate (GMBS) (16 mM). After 3 h incubation at room temperature, it was rinsed thoroughly with D.I. water. The GMBS-coated substrate was immersed in PBS buffer solution (10 mM phosphate buffer, 2.7 mM KCl, 137 mM NaCl, pH 7.4) with glutathione (GSH) (16 mM) for 12 h, and then was sonicated in D.I. water for 3 min. After being immersed in PBS buffer solution with 2-mercaptoethanol (1.6 M) for 2 h to quench the remained active GMBS functional groups, it was sonicated in D.I. water for 3 min. Next, the GSH-coated one was incubated in PBS buffer containing 0.43 µg/ml GST-tagged PLD1-PX at 4° C. for 30 min, and then was rinsed with PBST buffer (10 mM phosphate buffer, 2.7 mM KCl, 137 mM NaCl, 0.1% tween 20, pH 7.4). Finally, it was stored in PBS buffer at 4° C. for further study.

A silicon nitride ($Si_3N_4$) AFM tip was immersed in $HNO_3$: $H_2O$ (3:1 (v/v)) solution, and after being heated at 80° C. for 20 min, the tip was washed with D.I. water. The modification of the cleaned tip was the same as that of the Si wafer substrate except the introduction of GST-tagged Munc-18-1. The GSH-coated tip was incubated in PBS buffer solution with 0.97 µg/ml GST-tagged Munc-18-1 at 4° C. for 30 min. The final coated tip was rinsed with PBST buffer solution and stored at 4° C. for further study.

Both Munc-18-1 and PLD1-PX were signal transducer proteins and it has been known that Munc-18-1 in a cytoplasm of a brain cell forms a complex with phospholipase D1 (PLD1-PX) through PX domain of PLD1-PX in vivo.

Figure 12:
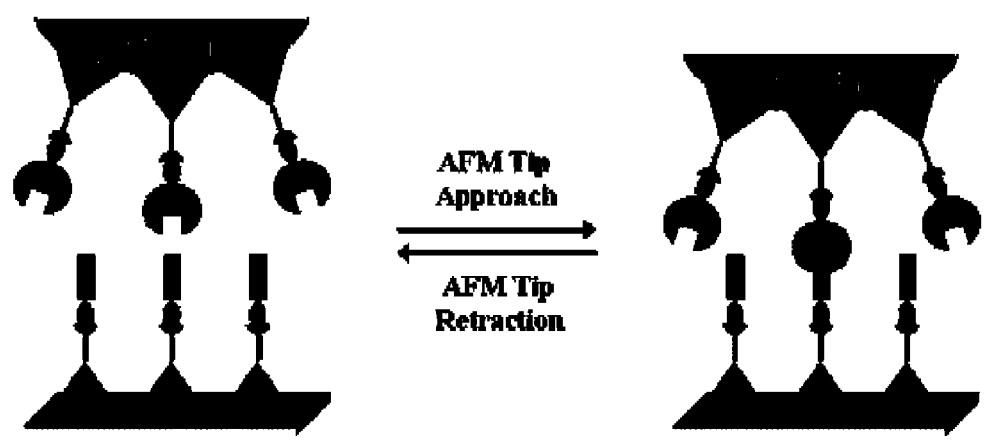
FIG. 12 shows the schematic view of the method of force measurement using an AFM
Figure 13:
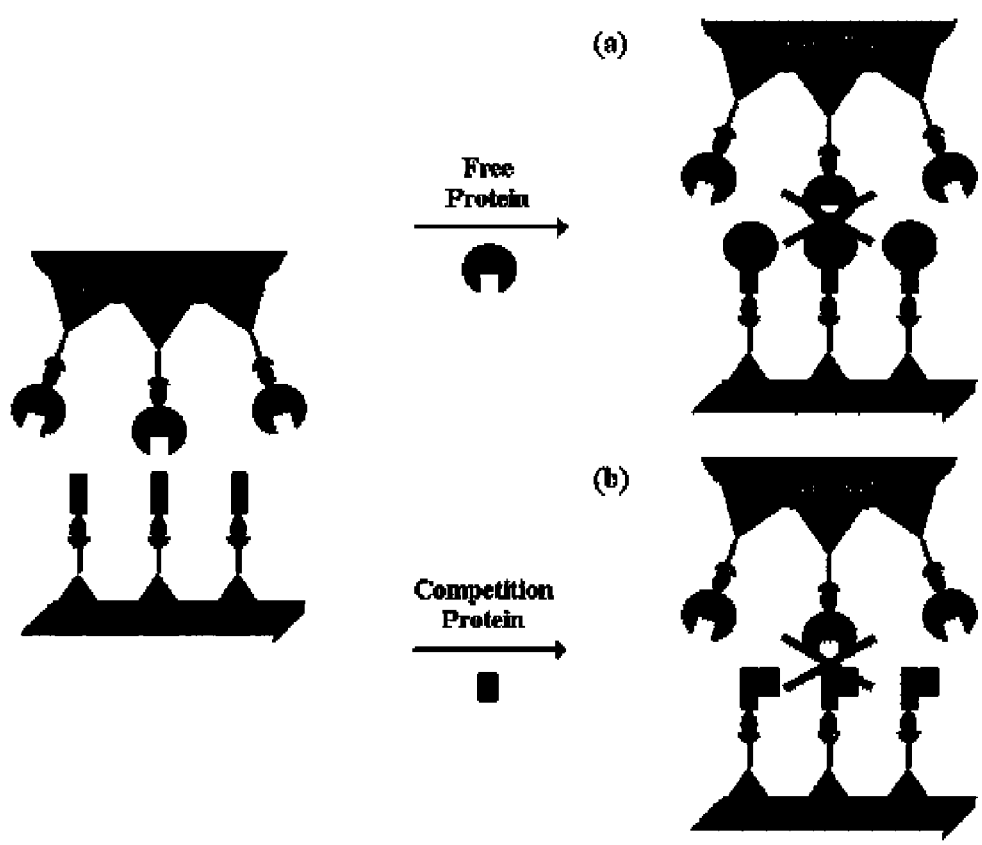
FIG. 13a shows a scheme for the force measurement with a blocking protein using an AFM.
FIG. 13b shows a scheme for the force measurement with a competitive protein using an AFM.
Figure 14:
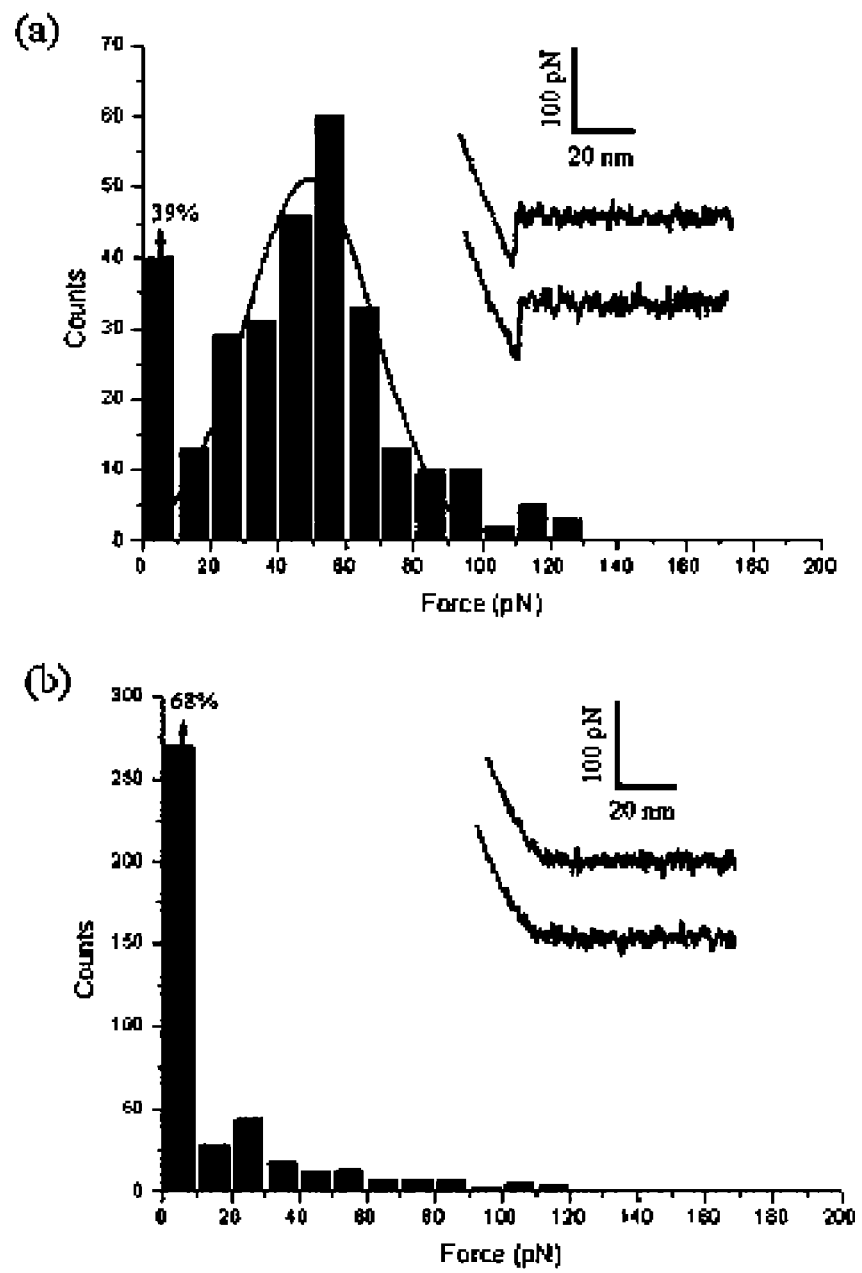
FIG. 14a is the histogram showing the force distribution for the interaction between Munc-18-1 and PLD1-PX.
FIG. 14b is the histogram showing the force distribution for the interaction between Munc-18-1 and PLD1-PX after adding excess amounts of free Munc-18-1 in solution.

When an AFM tip coated with Munc-18-1 approaches closely onto a substrate coated with PLD1-PX, and then retreats back, the binding force between both proteins can be measured (FIG. 12). The measured force is constant around 50 pN which means that one Munc-18-1 molecule interacted with one PLD1-PX in this study (FIG. 14(a)). Furthermore, when A-[27]-acid instead of A-[9]-acid was used as a dendron, it was observed that the ratio of single interaction to multiple one was enhanced from 1.5:1 to 3:1. This result implies that the bigger size of biomolecules need the larger spacing between them on surface for the specific single interaction, and this need can be easily satisfied by utilizing size-controllable dendron molecules. For additional study, in order to prove that the measured force results from the specific interaction between Munc-18-1 and PLD1-PX, not non-specific one, excess amounts of free Munc-18-1 in solution were added and blocked the binding site of PLD1-PX during the force measurement (FIG. 13(a)). As a result, the interaction force between Munc-18-1 on the tip and PLD1-PX on the substrate was not observed (FIG. 14(b)). Therefore, these above results shows that Munc-18-1 binds to PLD1-PX specifically with a constant force and a dendron-modified surface can control the spacing among biomolecules on surface resulting in the specific single biomolecular interaction.

Example 9

Biomolecular Interaction Among Three Different Biomolecules and its Application to a Drug Screening Some human diseases result from undesirable interaction between proteins in a body and several drug screening methods have been utilized to find the best drug candidates for those diseases. Recently, a Bio-AFM has also been applied to the drug screening assay. This method determines drug efficiency by measuring the interaction force between two different proteins before and after adding a drug candidate. In addition, it is possible to detect easily the optimal drug concentration for a medical treatment by controlling the drug concentration in situ. Here, we show that the dendron-modified surface can be applicable to a drug screening with a Bio-AFM.

Figure 15:
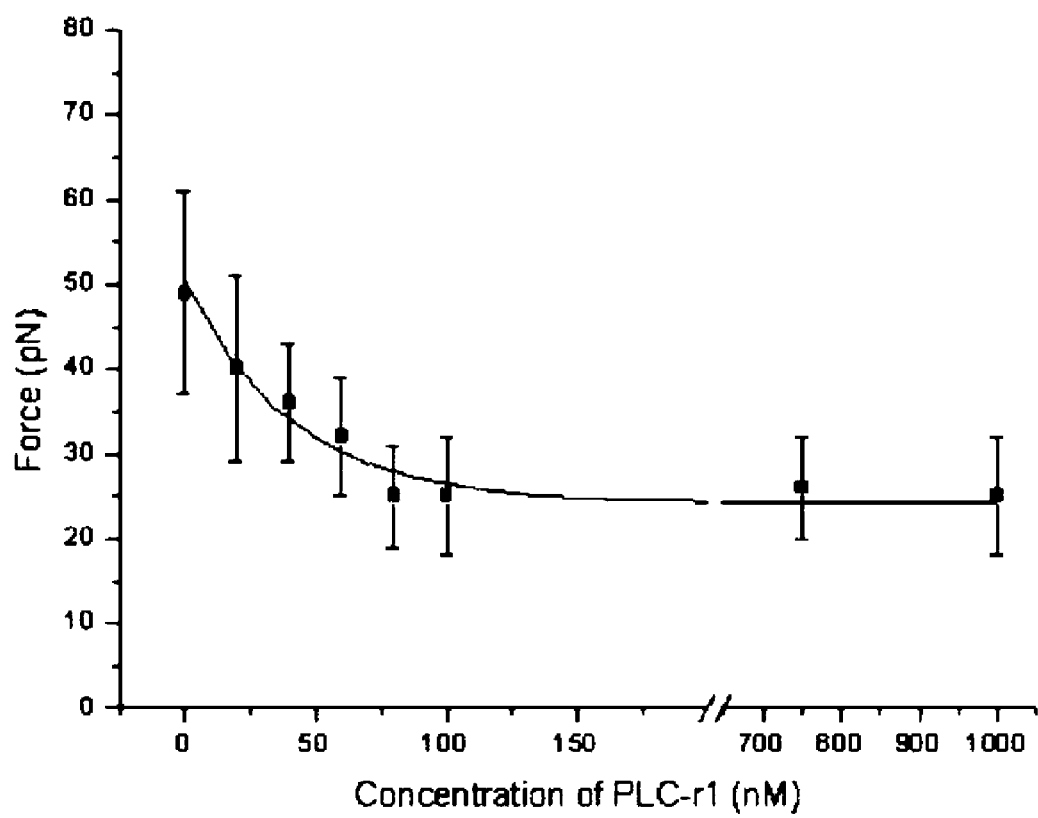
FIG. 15 is a graph showing the forces depending on the concentration of the competitive protein, PLC-γ1.

In this study, Munc-18-1 and PLD1-PX were introduced each onto an AFM tip and a substrate such as a Si wafer, as described in EXAMPLE 8. A drug candidate is PLC-γ1 which binds to PLD1-PX on the solid substrate and competes against Munc-18-1 on the tip (FIG. 13(b)). As testing with several different concentrations of PLC-γ1, high concentration of PLC-γ1 prevented PLD1-PX from binding to Munc-18-1 perfectly, but low concentration did not (FIG. 15). Consequently, this study suggests that PLC-γ1 is a competitor of Munc-18-1 and the interaction force between PLD1-PX and Munc-18-1 depends on the concentration of PLC-γ1. Therefore, this Bio-AFM assay can be extended to research for dug discovery and medical treatment.

Example 10

Biomolecular Interaction Between a Streptavidin and a Biotin

Streptavidin and a biotin have been used widely as a simple biomolecular interaction model. Here, this simple model was applied to a research field of force measurement with Bio-AFM. Because a streptavidin has two binding sites on its one side, it is difficult to prove that the measured force by a Bio-AFM result from the interaction between one streptavidin and one biotin. However, by controlling the spacing among biomolecules with a dendron molecule, we can observe one to one interaction force more easily.

An AFM tip and a solid substrate such as a Si wafer were functionalized with a dendron molecule, as described in EXAMPLE 8. A streptavidin was attached onto the substrate and a biotin onto the tip through DSC (di(N-succinimidyl) carbonate) linker molecule. The measured force is constant and almost similar to the published value which is believed to result from the interaction between one streptavidin and one biotin. This result suggests that a biotin molecule binds to a streptavidin molecule specifically through single interaction on the dendron-modified surface.

Moreover, it was observed that the ratio of single interaction to multiple one was higher on the surface coated with A-[9]-acid than A-[3]-acid. Namely, because of the small size of A-[3]-acid, the spacing between biomolecules on surface was not enough for one to one interaction. Consequently, because a dendron-modified surface can control the spacing among biomolecules on surface, it can ensure the specific single biomolecular interaction.

Example 11

Mapping of a Specific Ligand on a Cell Surface Through Biomolecular Interaction Between a Peptide and a Protein Although the interaction between a receptor on a cell surface and a ligand has been studied in depth using a confocal microscopy, this method has a unsolved problem that each receptor on a cell couldn't be defined with high resolution in nanometer scale. Recently, a Bio-AFM instrument has been made to overcome this limit. However, in spite of showing the possibility to define each receptor individually, this method also has an unsatisfied issue which is non-specific binding of an AFM tip to a cell surface and multiple binding between ligands on a tip and receptors on a cell. These problems can provide wrong information for receptor distribution on a cell. Previous studies showed that a dendron-modified surface has the characteristic of low non-specific binding with biomolecules and ensure the single biomolecular interaction by providing enough spacing between biomolecules attached on the surface. Therefore, the dendron-modified surface can easily help each receptor be detected separately with high resolution by a Bio-AFM.

RBL2H3 cell used in this study had an overexpressed FPR1 (Formyl Peptide Receptor 1) which is related to inflammation. After being cultivated in DMEM (10% FBS, 1% penicillin/streptomycin) under 5% $CO_2$ condition at 37° C. for 48 h, the cell with $5 \times 10^4$ cells/ml was attached onto a cover glass using 5% Matrigel solution. The ligand binding to FPR1 is the synthetic peptide consisting of six amino acids which cause inflammation and has a cysteine at its N terminal position for linking with GMBS linker molecule like the below. In addition, the peptide is neutralized in charge through acetylation at N terminal and amidation at C terminal.

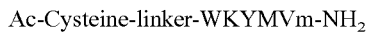

Ac-Cysteine-linker-WKYMVm-NH$_2$

An AFM tip was modified with a dendron molecule, as described in EXAMPLE 8. After being functionalized with GMBS and the peptide ligand, the tip scanned the cell surface measuring the force between a receptor and a ligand on a certain area of the cell (FIG. 16(a)). The experiment was performed in 1×PBS buffer solution (pH 7.4) at room temperature using The NanoWizard® Atomic Force Microscope (JPK Instruments, Inc) as a Bio-AFM.

FIG. 16 shows some of the measured force graphs where a blue line means the backward force curve as retracting a tip. From this curve, each force can be calculated and finally combined to make a force map to represent the distribution of the receptor on the cell surface. FIG. 17 shows the force map and force histogram for the interaction between FPR1 and its ligand peptide. A bright pixel means a strong force on the map, while a dark pixel does a weaker one (FIGS. 17 & 18). Two remarkable forces, 31 pN and 55 pN, were observed from the force histogram (FIG. 17). For a further study, an additional experiment was performed with a competitor, free WKYMVm in solution in order to prove that the measured force definitely came from the specific interaction between FPR1 and its ligand peptide (FIG. 18). As a result, it was found that the population of the force around 60 pN decreased significantly after incubation with the free peptide, WKYMVm (SEQ ID NO:17) for 1 h. This result suggests that the force around 60 pN results from the specific interaction between the receptor and the ligand, but the force around 30 pN is the background force due to the non-specific interaction.

Example 12

Biomolecular Interaction Between a Protein and a Glycolipid

Cholera toxin B has been known to bind selectively to one of glycolipids, ganglioside GM1 which exists on the surface of a human splanchnic epithelial cell and then to give rise to pain. Here we study the distribution of a ganglioside GM1 on a cell surface by measuring the force with its ligand, cholera toxin B.

A test cell is human epithelium with the overexpressed ganglioside GM1. After being cultivated in DMEM (10% FBS, 1% penicillin/streptomycin) under 5% CO$_2$ condition at 37° C. for 48 h, the cell with 5×10$^4$ cells/ml is attached onto a cover glass using 5% Matrigel solution. An AFM tip is modified with a dendron molecule followed by the deprotection of a protecting group, as described in EXAMPLE 8. After being functionalized with a linker molecule and cholera toxin B, the tip scans the cell surface measuring the force between a receptor and ligand on a certain area of the cell. The experiment is performed in 1×PBS buffer solution (pH 7.4) at room temperature using The NanoWizard® Atomic Force Microscope (JPK Instruments, Inc) as a Bio-AFM.

Example 13

Biomolecular Interaction Between a Lectin and a Glycoprotein

Concanavalin A, one of lectin proteins, has been used widely for studying the characteristics of a glycoprotein because it binds to a glycoprotein strongly. Here we investigate the distribution of a glycoprotein having a mannose at its terminal position, using concanavalin A as a ligand. The cell used in this experiment is a fibroblast with the glycoprotein on its surface.

After being cultivated in RPMI (10% FBS, 1% penicillin/streptomycin) under 5% CO$_2$ condition at 37° C. for 48 h, the cell with 5×10$^4$ cells/ml is attached onto a cover glass using 5% Matrigel solution. An AFM tip is modified with a dendron molecule followed by the deprotection of a protecting group, as described in EXAMPLE 8. After being functionalized with a linker molecule and Concanavalin A, the tip scans the surface of the cell attached on a cover glass measuring the force between a receptor and ligand on a certain area of the cell. The experiment is performed in 1×PBS buffer solution (pH 7.4) at room temperature using The NanoWizard® Atomic Force Microscope (JPK Instruments, Inc) as a Bio-AFM.

Example 14

Biomolecular Interaction Between a Carbohydrate and a Glycoprotein

*Mycobacterium tuberculosis* causes pulmonary tuberculosis because its surface has a HBHA (heparin-binding haemagglutinin adhesin) which binds to a heparin on an epithelial cell of a lung. Here we study the distribution of a HBHA on the surface of *Mycobacterium tuberculosis*, using a heparin as a ligand. The cell used in this experiment is a *mycobacterium bovis* BCG cell with a HBHA on its surface.

After being cultivated in Sauton medium under 5% CO$_2$ condition at 37° C. for 48 h, the cell with 5×10$^4$ cells/ml is attached onto a cover glass using 5% Matrigel solution. An AFM tip is modified with a dendron molecule followed by the deprotection of a protecting group, as described in EXAMPLE 8. After being functionalized with a linker molecule and a heparin, the tip scans the surface of the cell attached on a cover glass measuring the force between a receptor and ligand on a certain area of the cell. The experiment is performed in 1×PBS buffer solution (pH 7.4) at room temperature using The NanoWizard® Atomic Force Microscope (JPK Instruments, Inc) as a Bio-AFM.

Example 15

Biomolecular Interaction Between a Nerve Growth Factor (NGF) and a Tyrosine Kinase A NGF has been known to bind to a TrkA (tyrosine kinase A) on the surface of a nerve cell and control its survival function. In this study, we investigate the distribution of a TrkA expressed on the surface of a pheochromocytoma PC12 cell, using a NGF as a ligand.

After being cultivated in RPMI (5% FCS, 1% penicillin/streptomycin) under 5% CO$_2$ condition at 37° C. for 48 h, the cell with 5×10$^4$ cells/ml is attached onto a cover glass using 5% Matrigel solution. An AFM tip is modified with a dendron molecule followed by the deprotection of a protecting group, as described in EXAMPLE 8. After being functionalized with a linker molecule and the ligand, NGF, the tip scans the surface of the cell attached on a cover glass measuring the force between a receptor and ligand on a certain area of the cell. The experiment is performed in 1×PBS buffer solution (pH 7.4) at room temperature using The NanoWizard® Atomic Force Microscope (JPK Instruments, Inc) as a Bio-AFM.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A method for determining the presence of a mismatched nucleotide between a probe nucleotide and a target nucleotide, said method comprising:

comparing a control atomic force microscopy (AFM) binding force with a measured AFM binding force between a probe nucleotide and a target nucleotide to determine whether there is a mismatch between said probe nucleotide and said target nucleotide, wherein said AFM comprises a cantilever having a fixed end and a free end, wherein the free end of said cantilever comprises a tapered protrusion of surface region, and wherein said probe nucleotide is attached to said cantilever via a dendron comprising:

branched regions, and
a single linear region, and wherein a plurality of termini of said branched regions of dendron are covalently bound to the surface region of said cantilever, and said probe nucleotide is attached to the terminus of the single linear region of said dendron, wherein said dendrons are spaced at regular intervals between about 0.1 nm and about 100 nm.

2. The method of claim 1, wherein said control AFM finding force comprises a AFM binding force between said probe nucleotide and a perfectly matching oligomer, and wherein the presence of a difference in the control AFM binding force and the measured AFM binding force is an indication that a mismatched nucleotide is present between said probe nucleotide and said target nucleotide.

3. The method of claim 1, wherein the target nucleotide comprises a portion of a gene, and wherein the presence of mismatched nucleotide is an indication that a mutation is present in said gene.

4. The method of claim 1, wherein the control AFM binding force comprises AFM binding forces between said probe nucleotide and a plurality of mismatched oligonucleotides.

5. The method of claim 4, wherein said step of comparing the control AFM binding force with the measured AFM binding force comprises comparing the measured AFM binding force with AFM binding forces between said probe nucleotide and a plurality of mismatched oligonucleotides.

6. The method of claim 5, wherein said step of comparing the measured AFM binding force with the control AFM binding force is used to determine the number of mismatched nucleotides between said probe nucleotide and said target nucleotide.

7. The method of claim 1, wherein the presence of a mismatched nucleotide between said probe nucleotide and said target nucleotide is an indication of the presence of a disease.

8. The method of claim 1, wherein said method measures AFM binding force between a single target nucleotide and said probe nucleotide.

9. The method of claim 1, wherein said target nucleotide is bound to a substrate surface.

10. The method of claim 9, wherein said target nucleotide is bound to the substrate surface via a dendron comprising:
   branched regions, and
   a single linear region,
and wherein a plurality of termini of said branched regions of dendron are covalently bound to the surface of said cantilever, and said probe nucleotide is attached to the terminus of the single linear region of said dendron.

11. The method of claim 10, wherein said substrate comprises a plurality covalently bound dendrons that are spaced at regular intervals between about 0.1 nm and about 100 nm.

* * * * *

SEQUENCE LISTING

```
<160> NUMBER OF SEQ ID NOS: 17

<210> SEQ ID NO 1
<211> LENGTH: 20
<212> TYPE: DNA
<213> ORGANISM: Artificial Sequence
<220> FEATURE:
<223> OTHER INFORMATION: 20-bp oligomer on a substrate

<400> SEQUENCE: 1
ccatcgtggt tgctcctcag                                                20

<210> SEQ ID NO 2
<211> LENGTH: 30
<212> TYPE: DNA
<213> ORGANISM: Artificial Sequence
<220> FEATURE:
<223> OTHER INFORMATION: 30-bp oligomer on a subtrate

<400> SEQUENCE: 2
gctgctatgg agacacgccc tggaacgaag                                      30

<210> SEQ ID NO 3
<211> LENGTH: 40
<212> TYPE: DNA
<213> ORGANISM: Artificial Sequence
<220> FEATURE:
<223> OTHER INFORMATION: 40-bp oligomer on a substrate

<400> SEQUENCE: 3
tggatctggg gtgccattcc gctgtctcaa ggtgtgctcg                            40

<210> SEQ ID NO 4
<211> LENGTH: 50
<212> TYPE: DNA
<213> ORGANISM: Artificial Sequence
<220> FEATURE:
<223> OTHER INFORMATION: 50-bp oligomer on a substrate

<400> SEQUENCE: 4
gtctgacctg ttccaacgac ccgtatcact ccgctcctgc ctgctctcca                 50

<210> SEQ ID NO 5
<211> LENGTH: 20
<212> TYPE: DNA
<213> ORGANISM: Artificial Sequence
<220> FEATURE:
<223> OTHER INFORMATION: perfect matching 20-bp oligomer onto a tip

<400> SEQUENCE: 5
ctgaggagca accacgatgg                                                20

<210> SEQ ID NO 6
<211> LENGTH: 30
<212> TYPE: DNA
<213> ORGANISM: Artificial Sequence
<220> FEATURE:
<223> OTHER INFORMATION: perfect matching 30-bp oligomer onto a tip
```

<400> SEQUENCE: 6
cttcgttcca gggcgtgtct ccatagcagc                                           30

<210> SEQ ID NO 7
<211> LENGTH: 40
<212> TYPE: DNA
<213> ORGANISM: Artificial Sequence
<220> FEATURE:
<223> OTHER INFORMATION: perfect matching 40-bp oligomer on a tip

<400> SEQUENCE: 7
cgagcacacc ttgagacagc ggaatggcac cccagatcca                                40

<210> SEQ ID NO 8
<211> LENGTH: 50
<212> TYPE: DNA
<213> ORGANISM: Artificial Sequence
<220> FEATURE:
<223> OTHER INFORMATION: perfect mataching 50-bp oligomer on a tip

<400> SEQUENCE: 8
tggagagcag gcaggagcgg agtgatacgg gtcgttggaa caggtcagac                     50

<210> SEQ ID NO 9
<211> LENGTH: 20
<212> TYPE: DNA
<213> ORGANISM: Artificial Sequence
<220> FEATURE:
<223> OTHER INFORMATION: single base mismatching 20-bp oligomer onto a
      tip

<400> SEQUENCE: 9
ctgaggagct accacgatgg                                                      20

<210> SEQ ID NO 10
<211> LENGTH: 30
<212> TYPE: DNA
<213> ORGANISM: Artificial Sequence
<220> FEATURE:
<223> OTHER INFORMATION: single base mismatching 30-bp oligomer on a tip

<400> SEQUENCE: 10
cttcgttcca gggcgcgtct ccatagcagc                                           30

<210> SEQ ID NO 11
<211> LENGTH: 40
<212> TYPE: DNA
<213> ORGANISM: Artificial Sequence
<220> FEATURE:
<223> OTHER INFORMATION: single base pair mismatching 40-bp oligmer onto
      a tip

<400> SEQUENCE: 11
cgagcacacc ttgagacagc gtaatggcac cccagatcca                                40

<210> SEQ ID NO 12
<211> LENGTH: 50
<212> TYPE: DNA
<213> ORGANISM: Artificial Sequence
<220> FEATURE:
<223> OTHER INFORMATION: single base mismatching 50-bp oligmer onto a
      tip

<400> SEQUENCE: 12
tggagagcag gcaggagcgg agtgttacgg gtcgttggaa caggtcagac                     50

```
<210> SEQ ID NO 13
<211> LENGTH: 20
<212> TYPE: DNA
<213> ORGANISM: Artificial Sequence
<220> FEATURE:
<223> OTHER INFORMATION: double base mismatching 20-bp oligomer on a tip

<400> SEQUENCE: 13
ctgaggagct tccacgatgg                                               20

<210> SEQ ID NO 14
<211> LENGTH: 30
<212> TYPE: DNA
<213> ORGANISM: Artificial Sequence
<220> FEATURE:
<223> OTHER INFORMATION: double base mismatching 30-bp oligomer onto a
      tip

<400> SEQUENCE: 14
cttcgttcca gggctcgtct ccatagcagc                                    30

<210> SEQ ID NO 15
<211> LENGTH: 40
<212> TYPE: DNA
<213> ORGANISM: Artificial Sequence
<220> FEATURE:
<223> OTHER INFORMATION: double base mismatching 40-bp oligomer onto a
      tip

<400> SEQUENCE: 15
cgagcacacc ttgagacagc gtcatggcac cccagatcca                         40

<210> SEQ ID NO 16
<211> LENGTH: 50
<212> TYPE: DNA
<213> ORGANISM: Artificial Sequence
<220> FEATURE:
<223> OTHER INFORMATION: double base mismatching 50-bp oligomer onto a
      tip

<400> SEQUENCE: 16
tggagagcag gcaggagcgg agtgtaacgg gtcgttggaa caggtcagac              50

<210> SEQ ID NO 17
<211> LENGTH: 6
<212> TYPE: PRT
<213> ORGANISM: Artificial Sequence
<220> FEATURE:
<223> OTHER INFORMATION: free peptide
<220> FEATURE:
<221> NAME/KEY: VARIANT
<222> LOCATION: (6)..(6)
<223> OTHER INFORMATION: Met is D-Met

<400> SEQUENCE: 17

Trp Lys Tyr Met Val Met
1               5
```